United States Patent
Dales et al.

(10) Patent No.: US 8,501,746 B2
(45) Date of Patent: Aug. 6, 2013

(54) ORGANIC COMPOUNDS

(75) Inventors: Natalie Dales, Arlington, MA (US); Julia Fonarev, Richmond (CA); Jianmin Fu, Coquitlam (CA); Duanjie Hou, Burnaby (CA); Rajender Kamboj, Burnaby (CA); Vishnumurthy Kodumuru, Burnaby (CA); Natalia Pokrovskaia, New Westminster (CA); Vandna Raina, Burnaby (CA); Shaoyi Sun, Coquitlam (CA); Zaihui Zhang, Vancouver (CA)

(73) Assignees: Xenon Pharmaceuticals Inc., Burnaby, BC (CA); Novartis AG, Basel (CH)

( * ) Notice: Subject to any disclaimer, the term of this patent is extended or adjusted under 35 U.S.C. 154(b) by 715 days.

(21) Appl. No.: 12/303,490

(22) PCT Filed: Jun. 4, 2007

(86) PCT No.: PCT/US2007/070293
§ 371 (c)(1),
(2), (4) Date: Dec. 4, 2008

(87) PCT Pub. No.: WO2007/143597
PCT Pub. Date: Dec. 13, 2007

(65) Prior Publication Data
US 2009/0156615 A1  Jun. 18, 2009

Related U.S. Application Data

(60) Provisional application No. 60/810,915, filed on Jun. 5, 2006.

(51) Int. Cl.
*A61K 31/4965* (2006.01)
*A61K 31/47* (2006.01)
*A61K 31/44* (2006.01)

(52) U.S. Cl.
USPC ....... 514/255.05; 514/314; 514/333; 514/342

(58) Field of Classification Search
None
See application file for complete search history.

(56) References Cited

U.S. PATENT DOCUMENTS 3,575,991 A * 4/1971 Kim et al. ............... 546/270.4

FOREIGN PATENT DOCUMENTS

| WO | WO 94/26249 | * | 11/1994 |
| WO | 2005/018557 A | | 3/2005 |
| WO | WO 2005/018557 | * | 3/2005 |

OTHER PUBLICATIONS

STN Search Report (Accession No. 1971:436007)—containing summary of US 3,575,991.*

* cited by examiner

*Primary Examiner* — Craig Ricci
(74) *Attorney, Agent, or Firm* — Seed IP Law Group PLLC

(57) ABSTRACT

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

16 Claims, No Drawings

ORGANIC COMPOUNDS

FIELD OF THE INVENTION

The present invention relates generally to the field of inhibitors of stearoyl-CoA desaturase, such as heterocyclic derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome, dermatological disorders and the like.

BACKGROUND OF THE INVENTION

Acyl desaturase enzymes catalyze the formation of a double bond in fatty acids derived from either dietary sources or de novo synthesis in the liver. In mammals, at least three fatty acid desaturases exists, each with differing specificity: delta-9, delta-6, and delta-5, which introduce a double bond at the 9-10, 6-7, and 5-6 positions respectively.

Stearoyl-CoA desaturases (SCDs) act with cofactors (other agents) such as NADPH, cytochrome b5, cytochrome b5 reductase, Fe, and molecular $O_2$ to introduce a double bond into the C9-C10 position (delta 9) of saturated fatty acids, when conjugated to Coenzyme A (CoA). The preferred substrates are palmitoyl-CoA (16:0) and stearoyl-CoA (18:0), which are converted to palmitoleoyl-CoA (16:1) and oleyl-CoA (18:1), respectively. The resulting mono-unsaturated fatty acids are substrates for further metabolism by fatty acid elongases or incorporation into phospholipids, triglycerides, and cholesterol esters. A number of mammalian SCD genes have been cloned. For example, two genes have been identified in humans (hSCD1 and hSCD5) and four SCD genes have been isolated from mouse (SCD1, SCD2, SCD3, and SCD4). While the basic biochemical role of SCD has been known in rats and mice since the 1970's (Jeffcoat, R. et al., *Eur. J. Biochem.* (1979), Vol. 101, No. 2, pp. 439-445; de Antueno, R. et al., *Lipids* (1993), Vol. 28, No. 4, pp. 285-290), it has only recently been directly implicated in human disease processes.

The two human SCD genes have been previously described: hSCD1 by Brownlie et al., PCT published patent application, WO 01/62954, the disclosure of which is hereby incorporated by reference in its entirety and hSCD2, PCT published patent application, WO 02/26944, incorporated herein by reference in its entirety.

To date, the only small-molecule, drug-like compounds known that specifically inhibit or modulate SCD activity are found in the following PCT Published Patent Applications: WO 06/034338, WO 06/034446, WO 06/034441, WO 06/034440, WO 06/034341, WO 06/034315, WO 06/034312, WO 06/034279, WO 06/014168, WO 05/011657, WO 05/011656, WO 05/011655, WO 05/011654 and WO 05/011653. SCD inhibitors have also been described in by Zhao et al., *Biorganic and Medicinal Chemistry Letters*, 2007, and PCT Published Patent Applications WO 06/130986 and WO 07/009,236.

Before the discovery of the above compounds, only certain long-chain hydrocarbons, analogs of the substrate stearic acid, had been used to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA, while cis-9, trans-11 isomer of conjugated linoleic acid does not have this biological activity. Cyclopropenoid fatty acids, such as those found in stercula and cotton seeds, are also known to inhibit SCD activity. For example, sterculic acid (8-(2 octylcyclopropenyl)octanoic acid) and malvalic acid (7-(2-oclylcyclopropenyl)heptanoic acid) are C18 and C16 derivatives of sterculoyl and malvaloyl fatty acids, respectively, having cyclopropene rings at their C9-C10 position. These agents must be coupled to CoA to act as inhibitors and are believed to inhibit SCD enzymatic activity by direct interaction with the enzyme complex, thus inhibiting delta-9 desaturation. Other agents that may inhibit SCD activity include thia-fatty acids, such as 9-thiastearic acid (also called 8-nonylthiooctanoic acid) and other fatty acids with a thioester moiety.

There is a major unmet need for small molecule inhibitors of SCD enzyme activity because evidence is now compelling that SCD activity is directly implicated in common human disease processes: See e.g., Attie, A. D. et al., "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al., "Role for stearoyl-CoA desaturase-1 in leptin mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. U.S.A.* (2002), Vol. 99, No. 7, pp. 11482-6, Gutierrez-Juarez, R. et al. "Critical role of stearoyl CoA desaturase-1 (SCD1) in the onset of diet-induced hepatic insulin resistance", *J. Clin. Invest.* (2006), Vol 116, No. 6, pp. 1686-95, Dobrzyn A. and Dobrzyn P. "Stearoyl-CoA desaturase—a new player in skeletal muscle metabolism regulation", *J. Physiol Pharmacol.* (2006), Vol 57 Suppl 10, pp. 31-42, Sampath, H. et al., "Stearoyl-CoA Desaturase-1 mediates the pro-lipogenic effects of dietary saturated fat", *J. Biol. Chem.*, (2007), Vol. 282, No. 4, pp 2483-93, Xu H. et al., "Hepatic knockdown of stearoyl-CoA desaturase 1 via RNA interference in obese mice decreases lipid content and change sfatty acid composition", *Front. Biosci.* (2007), Vol. 12, pp 3781-94.

The present invention solves this problem by presenting new drug-like classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

SUMMARY OF THE INVENTION

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of Formula (I):

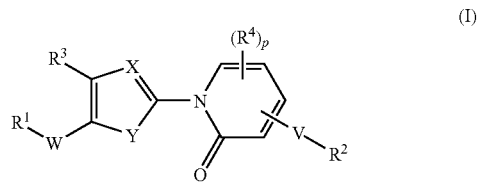

wherein,

V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_t$—, —S(O)$_t$N(R$^5$)—, —OS(O)$_2$—, —OS(O)$_2$N(R$^5$)—, —C(O)—, —OC(O)—, —C(O)O—, —N(R$^5$)C(=N(R$^{5a}$))NR$^5$—, —N(R$^5$)C(=S)NR$^5$—, —N(R$^5$)((R$^{5a}$)N=)C—, —C(=N(R$^{5a}$))N(R$^5$)—, alkylene, alkenylene, alkynylene, aryl, heteroaryl, a cycloalkyl, a heterocyclyl, or a direct bond;

W is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_t$—, —S(O)$_t$N(R$^5$)—, —OS(O)$_2$N(R$^5$)—, —C(O)—, —OC(O)—, —C(O)O—, —N(R$^5$)C(=N(R$^{5a}$))NR$^5$—, —N(R$^5$)((R$^{5a}$)N=)C—, —C(=N(R$^{5a}$))N(R$^5$)—, aryl, a heteroaryl, heterocyclyl, alkynylene, alkenylene, alkylene or a direct bond;

X is selected from C(H) or N;

Y is selected from S, O, N(H) or N(CH$_3$);

p is 0, 1, 2, or 3;

t is 1 or 2;

R$^1$ is selected from the group consisting of hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, and heteroarylalkyl;

or R$^1$ is a multi-ring structure having 2 to 4 rings wherein the rings are independently selected from the group consisting of cycloalkyl, heterocyclyl, aryl and heteroaryl and where some or all of the rings may be fused to each other;

R$^2$ is selected from the group consisting of hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl and heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of hydrogen, alkyl, alkenyl, alkoxy, hydroxyalkyl, alkoxyalkyl, cycloalkyl, cycloalkylalkyl, heterocyclyl, aryl, aralkyl, heteroaryl, halo, haloalkyl, trihaloalkoxyl, cyano and —N(R$^5$)$_2$;

R$^4$ is selected from the group consisting of alkyl, hydroxyalkyl, cycloalkylalkyl, aralkyl, halo, haloalkyl, —OCF$_3$, —OC(H)F$_2$, and cyano;

or two adjacent R$^4$ groups, together with the carbon atoms to which they are attached, may form a cycloalkyl, heterocyclyl, aryl or heteroaryl and the remaining R$^4$ groups, if present, are as described above;

R$^5$ is selected from the group consisting of hydrogen, aryl, alkyl, heteroaryl, heterocyclyl, haloalkyl, hydroxyalkyl, cycloalkylalkyl and aralkyl;

R$^{5a}$ is selected from the group consisting of hydrogen, alkyl, cycloalkylalkyl and cyano;

a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism and/or lipid homeostasis utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol. In another aspect, the invention provides the use of the compounds of the invention, as set forth above, in the preparation of a medicament for the treatment of SCD-mediated disease or condition in a mammal, preferably a human.

It is understood that the scope of the invention as it relates to compounds of Formula (I) is not intended to encompass compounds which are known, including, but not limited to, any specific compounds which are disclosed and/or claimed in the following publications:

PCT Published Patent Application, WO 00/25768;
PCT Published Patent Application, WO 99/47507;
PCT Published Patent Application, WO 01/60458;
PCT Published Patent Application, WO 01/60369;
PCT Published Patent Application, WO 94/26720;
European Published Patent Application, 0 438 230;
European Published Patent Application, 1 184 442;
CA 2,114,178; and U.S. Pat. No. 5,334,328;
U.S. Pat. No. 5,310,499; and
US Published Patent Application, 2003/0127627.

DETAILED DESCRIPTION OF THE INVENTION

Definitions

Certain chemical groups named herein are preceded by a shorthand notation indicating the total number of carbon atoms that are to be found in the indicated chemical group. For example, $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Cyano" refers to the —CN radical;
"Hydroxy" refers to the —OH radical;
"Nitro" refers to the —NO$_2$ radical;
"Amino" refers to the —NR$^{14}$ or NR$^{15}$ radical;
"Mercapto" refers to the —SR radical;
"Acid" refers to the —COOH radical;
"Trifluoromethyl" refers to the —CF$_3$ radical;

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl(iso-propyl), n-butyl, n-pentyl, 1,1-dimethylethyl(t-butyl), and the like. Unless stated otherwise specifically in the specification, an alkyl group may be optionally substituted by one or more of the following groups: alkyl, alkenyl, halo, cyano, aryl, cycloalkyl, heterocyclyl, heteroaryl, —Si(CH$_3$)$_2$C(CH$_3$)$_{3}$, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$, —S—, —S(O)$_t$OR$^{16}$, —S(O)$_t$R$^{16}$, and —S(O)$_t$N(R$^{14}$)$_2$ and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms or two to six carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$—N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$, —S—R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms, preferably two to eight carbon atoms or two to six carbon atoms and which is attached to the rest of the molecule by a single bond. Unless stated otherwise specifically in the specification, an alkynyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$—N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$, —S—, —S(O)$_t$OR$^{16}$, —S(O)$_t$R$^{16}$, and —S(O)$_t$N(R$^{14}$)$_2$ and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons or one to six carbon atoms, e.g., methylene, ethylene, propylene, n-butylene, and the like. The alkylene chain may be attached to the rest of the molecule and to the radical group through one carbon within the chain or through any two carbons within the chain. Unless stated otherwise specifically in the specification, an alkylene chain may be optionally substituted by one or more of the following groups: alkyl, alkenyl, halo, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$, —S—, —S(O)$_t$OR$^{16}$, —S(O)$_t$R$^{16}$, and —S(O)$_t$N(R$^{14}$)$_2$ and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms or two to six carbon atoms, e.g., ethenylene, propenylene, n-butenylene, and the like. Unless stated otherwise specifically in the specification, an alkenylene chain may be optionally substituted by one or more of the following groups: alkyl, alkenyl, halo, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$, —S—, —S(O)$_t$OR$^{16}$, —S(O)$_t$R$^{16}$, and —S(O)$_t$N(R$^{14}$)$_2$, and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl. "Alkynylene" and "Alkynylene chain" refer to a straight or branched divalent hydrocarbon chain linking the rest of the molecule to a radical group, consisting solely of carbon and hydrogen, containing at least one triple bond and having from two to twelve carbon atoms or two to six carbon atoms, e.g. propynylene, n butynylene, and the like. Unless stated otherwise specifically in the specification, an alkynylene chain may be optionally substituted by one or more of the following groups: alkyl, alkenyl, halo, cyano, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$, —S—, —S(O)$_t$OR$^{16}$, —S(O)$_t$R$^{16}$, and —S(O)$_t$N(R$^{14}$)$_2$, and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, cycloalkyl, cycloalkylalkyl, aryl, aralkyl, heterocyclyl, heterocyclylalkyl, heteroaryl or heteroarylalkyl.

"Alkoxy" refers to a radical of the formula —OR$_a$ where R$_a$ is an alkyl radical as generally defined above. The alkyl part of the alkoxy radical may be optionally substituted as defined above for an alkyl radical.

"Alkoxyalkyl" refers to a radical of the formula —R$_b$—O—R$_a$ where R$_b$ is an alkylene chain as defined above and R$_a$ is an alkyl radical as defined above. The oxygen atom may be bonded to any carbon in the alkylene chain and in the alkyl radical. The alkyl part of the alkoxyalkyl radical may be optionally substituted as defined above for an alkyl group. The alkylene chain part of the alkoxyalkyl radical may be optionally substituted as defined above for an alkylene chain.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially saturated. Aryl groups include, but are not limited to groups such as fluorenyl, phenyl, indenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)S(O)$_t$R$^{16}$, —S—, —R$^{15}$—S(O)$_t$R$^{16}$, —R$^{15}$—S(O)$_t$R$^{16}$, and —R$^{15}$—S(O)$_t$N(R$^{14}$)$_2$ and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —R$_a$R$_b$ where R$_a$ is an alkylene chain as defined above and R$_b$ is one or more aryl radicals as defined above, e.g., benzyl, diphenylmethyl and the like. The aryl part of the aralkyl radical may be optionally substituted as described above for an aryl group. The alkylene chain part of the aralkyl radical may be optionally substituted as defined above for an alkyl group.

"Aralkenyl" refers to a radical of the formula —R$_a$R$_b$ where R$_a$ is an alkenylene chain as defined above and R$_b$ is one or more aryl radicals as defined above, which may be optionally substituted as described above. The aryl part of the aralkenyl radical may be optionally substituted as described above for an aryl group. The alkenylene chain of the aralkenyl radical may be optionally substituted as defined above for an alkenyl group.

"Aryloxy" refers to a radical of the formula —OR$_b$ where R$_b$ is an aryl group as defined above. The aryl part of the aryloxy radical may be optionally substituted as defined above.

"Cycloalkyl" refers to a stable non-aromatic monocyclic or polycyclic hydrocarbon radical consisting solely of carbon and hydrogen atoms, having from three to fifteen carbon atoms, preferably having from three to twelve carbon atoms or from three to six atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, cyano, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, R$^{15}$—C(O)R$^{14}$, —R$^{15}$—C(O)OR$^{14}$, —R$^{15}$—C(O)N(R$^{14}$)$_2$, R$^{15}$—N(R$^{14}$)C(O)OR$^{16}$, —R$^{15}$—N(R$^{14}$)C(O)R$^{16}$, —R$^{15}$—N(R$^{14}$)S(O)$_t$R$^{16}$, —S—, —R$^{15}$—S(O)OR$^{16}$, —R$^{15}$—S(O)$_t$R$^{16}$, and —R$^{15}$—S(O)$_t$N(R$^{14}$)$_2$ and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —R$_a$R$_d$ where R$_a$ is an alkylene chain as defined above and R$_d$ is a cycloalkyl radical as defined above. The alkylene chain and the cycloalkyl radical may be optionally substituted as defined above.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally alkylated/substituted; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, cyano, oxo, thioxo, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)S(O)$_t$R$^{16}$, —S—, —R$^{15}$—S(O)OR$^{16}$, —R$^{15}$—S(O)$_t$R$^{16}$, and —R$^{15}$—S(O)$_t$N(R$^{14}$)$_2$ and each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Heterocyclylalkyl" refers to a radical of the formula —$R_aR_e$ where $R_a$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic or tricyclic ring system, which may include fused or bridged ring systems; and the nitrogen, carbon or sulfur atoms in the heteroaryl radical may be optionally oxidized; the nitrogen atom may be optionally alkylated/substituted. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, cyano, oxo, thioxo, nitro, aryl, aralkyl, cycloalkyl, cycloalkylalkyl, heterocyciyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$, —$S$—, —$R^{15}$—$S(O)OR^{16}$, —$R^{15}$—$S(O)_tR^{16}$, and —$R^{15}$—$S(O)_tN(R^{14})_2$ and each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Heteroarylalkyl" refers to a radical of the formula —$R_aR_f$ where $R_a$ is an alkylene chain as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Hydroxyalkyl" refers to a radical of the formula —$R_a$—OH where $R_a$ is an alkylene chain as defined above. The hydroxy group may be attached to the alkyl radical on any carbon within the alkyl radical. The alkyl part of the hydroxyalkyl group may be optionally substituted as defined above for an alkyl group. "Trihaloalkoxy" refers to a radical of the formula —$OR_g$ where $R_g$ is a haloalkyl group as defined above where three halo are substituted on an alkyl. The trihaloalkyl part of the trihaloalkoxy group may be optionally substituted as defined above for a haloalkyl group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to each other through direct bonds or some or all of the rings may be fused to each other.

A "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto or acid group is bonded to any group that, when the prodrug of the compound of the invention is administered to a mammalian subject, cleaves to form a free hydroxy, free amino or free mercapto or acid group, respectively. Examples of prodrugs include, but are not limited to, acetate, formate and benzoate derivatives of alcohol or amides of amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients thereof.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age and body weight of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, i.e., relieving the symptoms without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

Also within the scope of the invention are intermediate compounds of Formula (I) and all polymorphs of the aforementioned species and crystal habits thereof.

The chemical naming protocol and structure diagrams used herein employ and rely on the chemical naming features as utilized by ChemDraw Version 10.0 software program (available from Cambridgesoft® Corp., Cambridge, Mass.).

EMBODIMENTS OF THE INVENTION

One embodiment of the invention is the compounds of Formula (I):

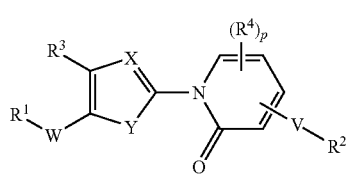

wherein,
V is selected from —N($R^5$)C(O)—, —C(O)N($R^5$)—, —OC(O)N($R^5$)—, —N($R^5$)C(O)O—, —N($R^5$)C(O)N($R^5$)—, —O—, —N($R^5$)—, —S—, —S(O)$_t$—, —N($R^5$)S(O)$_t$—, —S(O)$_t$N($R^5$)—, —OS(O)$_2$N($R^5$)—, —C(O)—, —OC(O)—, —C(O)O—, —N($R^5$)C(=N($R^{5a}$))N$R^5$—, —N($R^5$)C(=S)N$R^5$—, —N($R^5$)(($R^{5a}$)N=)C—, —C(=N($R^{5a}$))N($R^5$)—, alkylene, alkenylene, alkynylene, aryl, heteroaryl, cycloalkyl, heterocyclyl or a direct bond;

W is selected from —N($R^5$)C(O)—, —C(O)N($R^5$)—, —OC(O)N($R^5$)—, —N($R^5$)C(O)O—, —N($R^5$)C(O)N($R^5$)—, —O—, —N($R^5$)—, —S—, —S(O)$_t$—, —N($R^5$)S(O)$_t$—, —S(O)$_t$N($R^5$)—, —OS(O)$_2$N($R^5$)—, —C(O)—, —OC(O)—, —C(O)O—, —N($R^5$)C(=N($R^{5a}$))N$R^5$—, —N($R^5$)(($R^{5a}$)N=)C—, —C(=N($R^{5a}$))N($R^5$)—, aryl, heteroaryl, heterocyclyl, alkynylene, alkenylene, alkylene or a direct bond;

X is selected from C(H) or N;
Y is selected from S, O, N(H) or N($CH_3$);
p is 0, 1, 2, or 3;
t is 1 or 2;
$R^1$ is selected from the group consisting of hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, and heteroarylalkyl;
or $R^1$ is a multi-ring structure having 2 to 4 rings wherein the rings are independently selected from the group consisting of cycloalkyl, heterocyclyl, aryl and heteroaryl and where some or all of the rings may be fused to each other;
$R^2$ is selected from the group consisting of hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl and heteroarylalkyl;
or $R^2$ is a multi-ring structure having 2 to 4 rings wherein the rings are independently selected from the group consisting of cycloalkyl, heterocyclyl, aryl and heteroaryl and where some or all of the rings may be fused to each other;
$R^3$ is selected from the group consisting of hydrogen, alkyl, alkenyl, alkoxy, hydroxyalkyl, alkoxyalkyl, cycloalkyl, cycloalkylalkyl, heterocyclyl, aryl, aralkyl, heteroaryl, halo, haloalkyl, haloalkoxyl, cyano and —N($R^5$)$_2$;
$R^4$ is selected from the group consisting of alkyl, hydroxyalkyl, cycloalkyl, cycloalkylalkyl, aralkyl, halo, haloalkyl, —OCF$_3$, —OC(H)F$_2$, and cyano;
or two adjacent $R^4$ groups, together with the carbon atoms to which they attached, may form a cycloalkyl, heterocyclyl, aryl or heteroaryl and the remaining $R^4$ groups, if present, are as described above;
$R^5$ is selected from the group consisting of hydrogen, aryl, alkyl, heteroaryl, heterocyclyl, haloalkyl, hydroxyalkyl, cycloalkylalkyl and aralkyl;
$R^{5a}$ is selected from the group consisting of hydrogen, alkyl, cycloalkylalkyl and cyano;
a stereoisomer, enantiomer or tautomer thereof, a pharmaceutically acceptable salt thereof, a pharmaceutical composition thereof or a prodrug thereof.

Another embodiment is represented by Formula (I), wherein X is C(H) and Y is S;
V is selected from —O— or a direct bond;
W is selected from —N($R^5$)C(O)—, —C(O)N($R^5$)—, —C(O)O— or a direct bond;
p is 0, 1, 2, or 3;
$R^1$ is selected from the group consisting of hydrogen, alkyl, aryl, aralkyl, heterocyclyl, heterocyclylalkyl, heteroaryl, and heteroarylalkyl;
$R^2$ is selected from the group consisting of hydrogen, alkyl, alkynyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
or $R^2$ is a multi-ring structure having 2 to 4 rings wherein the rings are independently selected from the group consisting of cycloalkyl, heterocyclyl, aryl and heteroaryl and where some or all of the rings may be fused to each other;
$R^3$ is selected from the group consisting of hydrogen and alkyl;
$R^4$ is alkyl or haloalkyl; and
$R^5$ is selected from the group consisting of hydrogen or alkyl.

Another embodiment is represented by Formula (I), wherein X is N and Y is S;
V is selected from —O— or a direct bond;
W is selected from —N($R^5$)C(O)—, —C(O)N($R^5$)—, —C(O)O— or a direct bond;
p is 0, 1, 2, or 3;
$R^1$ is selected from the group consisting of hydrogen, alkyl, aryl, aralkyl, heterocyclyl, heterocyclylalkyl, heteroaryl, and heteroarylalkyl;
$R^2$ is selected from the group consisting of hydrogen, alkyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or $R^2$ is a multi-ring structure having 2 to 3 rings wherein the rings are independently selected from the group consisting of cycloalkyl, heterocyclyl, aryl and heteroaryl and where some or all of the rings may be fused to each other;
$R^3$ is selected from the group consisting of hydrogen and alkyl;
$R^4$ is alkyl or CF$_3$; and
$R^5$ is selected from the group consisting of hydrogen or alkyl.

Another embodiment is a compound of Formula (I), wherein X is N and Y is N—CH$_3$ or NH;
V is selected from —O— or a direct bond;
W is selected from —N($R^5$)C(O)—, —C(O)N($R^5$)—, —OC(O)—, —C(O)O— or a direct bond;
p is 0, 1, 2, or 3;

$R^1$ is selected from the group consisting of hydrogen, alkyl, aryl, aralkyl, heterocyclyl, heterocyclylalkyl, heteroaryl, and heteroarylalkyl;

$R^2$ is selected from the group consisting of hydrogen, alkyl, alkynyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of hydrogen and alkyl;

$R^4$ is alkyl, halo and haloalkyl; or two adjacent $R^4$ groups, together with the carbon atoms to which they attached, may form a cycloalkyl, heterocyclyl, aryl or heteroaryl and the remaining $R^4$ groups, if present, are as described above; and $R^5$ is selected from the group consisting of hydrogen or alkyl.

Another embodiment is represented by Formula (I), wherein

X is selected from CH or N;

Y is selected from S, O, N(H) or N(CH$_3$);

V is selected from —O— or a direct bond;

W is selected from —N(R$^5$)C(O)—, —C(O)N(R$^5$)—, —C(O)O— or a direct bond;

p is 0, 1, 2, or 3;

$R^1$ is selected from the group consisting of hydrogen, alkyl, aryl, aralkyl, alkoxy, heterocyclyl, heterocyclylalkyl, heteroaryl, and heteroarylalkyl;

$R^2$ is selected from the group consisting of hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl and heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of hydrogen and alkyl;

$R^4$ is alkyl or haloalkyl; and $R^5$ is selected from the group consisting of hydrogen or alkyl Another embodiment is a compound of Formula (I), wherein X is selected from CH or N;

Y is selected from S, O, N(H) or N(CH$_3$);

V is selected from —O— or a direct bond;

W is selected from —N(R$^5$)C(O)—, or —C(O)O—;

p is 0, 1, 2, or 3;

$R^1$ is selected from the group consisting of alkyl, aryl, aralkyl, heterocyclyl, heterocyclylalkyl, and heteroarylalkyl;

$R^2$ is selected from the group consisting of hydrogen, alkyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or $R^2$ is a multi-ring structure having 2 to 3 rings wherein the rings are independently selected from the group consisting of cycloalkyl, heterocyclyl, aryl and heteroaryl and where some or all of the rings may be fused to each other;

$R^3$ is selected from the group consisting of hydrogen and alkyl;

$R^4$ is haloalkyl, or alkyl; and $R^5$ is selected from the group consisting of hydrogen or alkyl.

Another embodiment is a compound of Formula (I), wherein

X is selected from CH or N;

Y is selected from S, O, N(H) or N(CH$_3$);

V is selected from —O— or a direct bond;

W is selected from —N(R$^5$)C(O)—, or —C(O)O—;

p is 0, 1, 2, or 3;

$R^1$ is selected from the group consisting of alkyl, aryl, aralkyl, heterocyclyl, heterocyclylalkyl, and heteroarylalkyl;

$R^2$ is selected from the group consisting of hydrogen, alkyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or $R^2$ is a multi-ring structure having 2 to 3 rings wherein the rings are independently selected from the group consisting of cycloalkyl, heterocyclyl, aryl and heteroaryl and where some or all of the rings may be fused to each other;

$R^3$ is selected from the group consisting of hydrogen and alkyl;

$R^4$ is haloalkyl, or alkyl; and $R^5$ is selected from the group consisting of hydrogen or alkyl.

Another embodiment is a compound of Formula (I), wherein

X is selected from CH or N;

Y is selected from S, O, NH or N—CH$_3$;

V is selected from —O— or a direct bond;

W is selected from —N(R$^5$)C(O)—, or —C(O)O—;

p is 0, 1, 2, or 3;

$R^1$ is selected from the group consisting of alkyl, aryl, aralkyl, heterocyclyl, heterocyclylalkyl, and heteroarylalkyl;

$R^2$ is selected from the group consisting of hydrogen, alkyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or $R^2$ is a multi-ring structure having 2 to 3 rings wherein the rings are independently selected from the group consisting of cycloalkyl, heterocyclyl, aryl and heteroaryl and where some or all of the rings may be fused to each other;

$R^3$ is selected from the group consisting of hydrogen and alkyl;

$R^4$ is alkyl or haloalkyl; and $R^5$ is selected from the group consisting of hydrogen or alkyl.

Another embodiment is a compound of Formula (I), wherein

V is selected from —O— or a direct bond;

W is selected from —N(R$^5$)C(O)—, or —C(O)O—;

p is 0, 1, 2, or 3;

$R^1$ is selected from the group consisting of alkyl, aryl, aralkyl, heterocyclyl, heterocyclylalkyl, and heteroarylalkyl;

$R^2$ is selected from the group consisting of hydrogen, alkyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or $R^2$ is a multi-ring structure having 2 to 3 rings wherein the rings are independently selected from the group consisting of cycloalkyl, heterocyclyl, aryl and heteroaryl and where some or all of the rings may be fused to each other;

$R^3$ is selected from the group consisting of hydrogen and alkyl;

$R^4$ is haloalkyl or alkyl; and $R^5$ is selected from the group consisting of hydrogen or alkyl.

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome, dermatological disorders and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome, dermatological disorders and the like, by administering to a patient in need of such treatment an effective amount of an SCD modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 28.

Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obesefa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)), and Sprague Dawley rats (Charles Rivers), as used in models for diet-induced obesity (Ghibaudi, L. et al., (2002), *Obes. Res.* Vol. 10, pp. 956-963). Similar models have also been developed for mice.

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition is defined as any disease or condition in which the activity of SCD is elevated and/or where inhibition of SCD activity can be demonstrated to bring about symptomatic improvements for the individual so treated. As defined herein, an SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In a preferred embodiment, compounds of the invention will be used to treat diabetes mellitus and/or obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a dermatological disorder, including but not limited to eczema, acne, psoriasis, keloid scar formation or prevention, diseases related to production or secretions from mucous membranes, such as monounsaturated fatty acids, wax esters, and the like. Preferably, the compounds of the invention inhibition of SCD activity can prevent or attenuate keloid scar formation by reduction of excessive sebum production that typically results in their formation. The investigation of the role of SCD inhibitors in the treatment of acne was advanced by the discovery that rodents lacking a functional SCD1 gene had changes to the condition of their eyes, skin, coat (Zheng Y., et al. "SCD1 is expressed in sebaceous glands and is disrupted in the asebia mouse", *Nat. Genet.* (1999) 23:268-270. Miyazaki, M., "Targeted Disruption of Stearoyl-CoA Desaturase1 Gene in Mice Causes Atrophy of Sebaceous and Meibomian Glands and Depletion of Wax Esters in the Eyelid", *J. Nutr.* (2001), Vol. 131, pp 2260-68., Binczek, E. et al., "Obesity resistance of the stearoyl-CoA desaturase-deficient mouse results from disruption of the epidermal lipid barrier and adaptive thermoregulation", *Biol. Chem.* (2007) Vol. 388 No. 4, pp 405-18).

An SCD-mediated disease or condition also includes inflammation, sinusitis, asthma, pancreatitis, osteoarthritis, rheumatoid arthritis, cystic fibrosis, and premenstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition that is, or is related to, neurological diseases, psychiatric disorders, multiple sclerosis, immune disorders and eye diseases, including but not limited to, disorders characterized by excessive or inappropriate lipid production by meiobium glands.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O' nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, 1Theus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POCYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA), which is accomplished by delta-9 desaturases, such as stearoyl-CoA desaturase 1 (SCD1). As such these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 20 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ ("Inhibitory Concentration of 50%") in a 15 minute microsomal assay of preferably less than 10 µM, less than 5 µM, less than 2.5 µM, less than 1 µM, less than 750 nM, less than 500 nM, less than 250 nM, less than 100 nM, less than 50 nM, and most preferably less than 20 nM. Compounds of the invention may show reversible inhibition (i.e., competitive inhibition) and preferably do not inhibit other iron binding proteins.

The identification of compounds of the invention as SCD inhibitors was readily accomplished using the SCD enzyme and microsomal assay procedure described in Shanklin J and Summerville C., *Proc. Natl. Acad. Sci. USA* (1991), Vol. 88, pp. 2510-2514. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain-groups tend to provide more potent inhibitory compounds. SAR analysis is one of the tools those skilled in the art may employ to identify preferred embodiments of the compounds of the invention for use as therapeutic agents. Other methods of testing the compounds disclosed herein are also readily available to those skilled in the art. Thus, in addition, the determination of the ability of a compound to inhibit SCD may be accomplished in vivo. In one such embodiment this is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (-TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase or other enzymes containing Fe at the active site.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available. Rabbits and hamsters are also useful as animal models, especially those expressing CETP (cholesterol ester transfer protein).

Another suitable method for determining the in vivo efficacy of the compounds of the invention is to indirectly measure their impact on inhibition of SCD enzyme by measuring a subject's Desaturation Index after administration of the compound.

"Desaturation Index" as employed in this specification means the ratio of the product over the substrate for the SCD enzyme as measured from a given tissue sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate).

Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, with a subsequent modulation of the activity of multiple enzymes present within the membrane, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented.

For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Alternatively, another format can be used to measure the effect of SCD inhibition on sebaceous gland function. In a typical study using ridnets, oral, intravenous or topical formulations of the SCD inhibitor are administered to a rodent for a period of 1 to 8 days. Skin samples are taken and prepared for histological assessment to determine sebaceous gland number, size, or lipid content. A reduction of sebaceous gland size, number or function would indicate that the SCD inhibitor would have a beneficial impact on acne vulgaris, (Clark, S. B. et al. "Pharmacological modulation of sebaceous gland activity: mechanisms and clinical applications", *Dermatol. Clin.* (2007) Vol. 25, No. 2, pp 137-46. Geiger, J. M., "Retinoids and sebaceous gland activity" *Dermatology* (1995), Vol. 191, No. 4, pp 305-10).

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and disorders contemplated herein.

Therapeutic doses are generally identified through a dose ranging study in humans based on preliminary evidence derived from animal studies. Doses must be sufficient to result in a desired therapeutic benefit without causing unwanted side effects for the patient. The preferred dosage range for an animal is 0.001 mg/Kg to 10,000 mg/Kg, including 0.5 mg/Kg, 1.0 mg/Kg, 2.0 mg/Kg 5.0 mg/Kg and 10 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, transdermal, topical, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

The pharmaceutical compositions according to the invention are those suitable for enteral, such as oral or rectal, transdermal, topical, and parenteral administration to mammals, including man, to inhibit stearoyl-CoA desaturase, and for the treatment of conditions associated with stearoyl desaturase activity. In general, the pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. For enteral or parenteral application, it is preferred to administer an effective amount of a pharmaceutical composition according to the invention as tablets or gelatin capsules. Such pharmaceutical compositions may comprise, for example, the active ingredient together with diluents (e.g., lactose, dextrose, sucrose, mannitol, sorbitol, cellulose and/or glycine), lubricants (e.g., silica, talcum, stearic acid, its magnesium or calcium salt and/or polyethyleneglycol), and for tablets also comprises binders (e.g., magnesium aluminum silicate, starch paste, gelatin, tragacanth, methylcellulose, sodium carboxymethylcellulose and/or polyvinylpyrrolidone) and disintegrants (e.g., starches, agar, alginic acid or its sodium salt) or effervescent mixtures and absorbents, colorants, flavors and sweeteners.

In another aspect of the present invention the compounds may be in the form of injectable compositions, e.g. preferably aqueous isotonic solutions or suspensions, and suppositories, which can be advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions may be prepared according to conventional mixing, granulating or coating methods, respectively, and contain about 0.1-75%, preferably about 1-50%, of the active ingredient.

Suitable formulations for transdermal and topical application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

The most suitable route will depend on the nature and severity of the condition being treated. Those skilled in the art are also familiar with determining administration methods, dosage forms, suitable pharmaceutical excipients and other matters relevant to the delivery of the compounds to a subject in need thereof.

The compounds of the invention may be usefully combined with one or more other therapeutic agents for the treatment of SCD-mediated diseases and conditions. Preferably, the other therapeutic agent is selected from antidiabetics, hypolipidemic agents, anti-obesity agents, anti-hypertensive agents or inotropic agents.

Thus, an additional aspect of the present invention concerns a pharmaceutical composition comprising a therapeutically effective amount of a compound of the invention in combination with one or more other therapeutic agents. For example, the composition can be formulated to comprise a therapeutically effective amount of a compound of the invention as defined above, in combination with another therapeutic agent, each at an effective therapeutic dose as reported in the art. Such therapeutic agents may, for example, include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARγ and/or PPARα (peroxisome proliferator-activated receptor) ligands such as MCC-555, MK767, L-165041, GW7282 or thiazolidinediones such as rosiglitazone, pioglitazone, troglitazone; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441, N,N-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237 (Vildagliptin) or MK-0431 (Stiagliptin); hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na—K-ATPase membrane pump, such as digoxin; neutral-endopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (Expert Opin Investig Drugs. (2003) April; 12(4):623-33) in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

In another aspect is the use of the pharmaceutical composition as described above for production of a medicament for the treatment of SCD-mediated disease or conditions.

In another aspect is the use of a pharmaceutical composition or combination as described above for the preparation of a medicament for the treatment of conditions associated with stearoyl-CoA desaturase activity.

A pharmaceutical composition as described above for the treatment of conditions associated with the inhibition of stearoyl-CoA desaturase.

Preparation of the Compounds of the Invention

The following Reaction Schemes illustrate methods to make compounds of the invention, i.e., compounds of Formula (I):

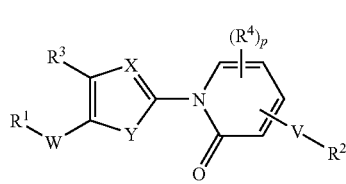

wherein p, V, W, X, Y, $R^1$, $R^2$, $R^3$ and $R^4$ are as defined above in the Summary of the Invention for compounds of Formula (I), as a stereoisomer, enantiomer or tautomer thereof, a pharmaceutically acceptable salt thereof, a pharmaceutical composition thereof or a prodrug thereof.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in Greene, T. W. and P. G. M. Wuts, *Protective Groups in Organic Synthesis* (2006), 4th Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry Reactions, Mechanisms, and Structure, 5th edition (Wiley, December 2000)) or prepared as described in this invention.

In general, the compounds of Formula (I) of this invention can be synthesized following the general procedure as described in Reaction Scheme 1 where W is —$N(R^5)C(O)$—, and p, $R^1$, $R^2$, $R^3$, $R^4$, $R^5$, W, V, X and Y are defined as in the Specification unless specifically defined otherwise. R' is a protecting group.

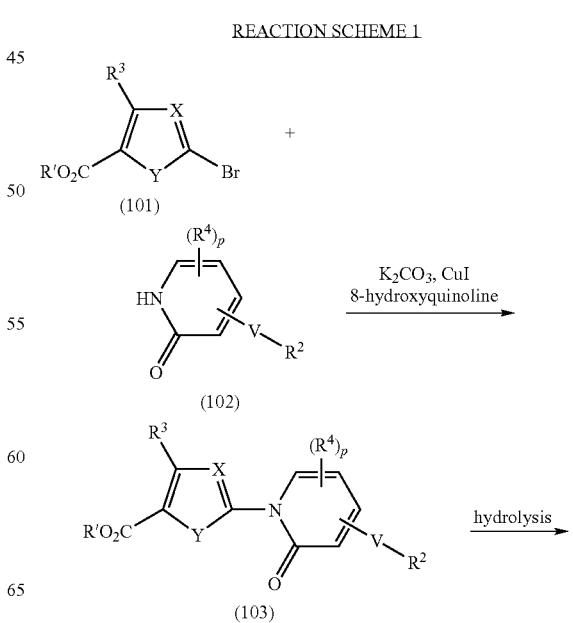

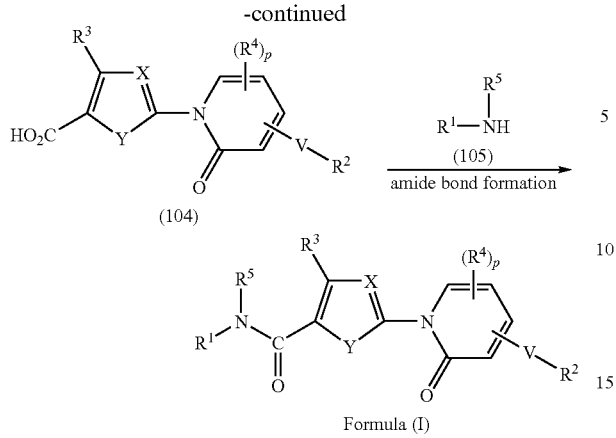

Formula (I)

The starting materials for the above reaction scheme are commercially available or can be prepared according to methods known to one skilled in the art or by methods disclosed herein. In general, the compounds of the invention are prepared in the above reaction scheme as follows:

Compound (101) is coupled with compound (102) under metal catalyzed reaction conditions to generate compound (103) which undergoes a standard hydrolysis procedure known to one skilled in the art to generate the carboxylic acid (104). Coupling between compounds (104) and (105) under standard amide bond formation conditions known to the one skilled in the art affords compounds of Formula (I) of the invention where W is —N($R^5$)C(O)—.

Alternatively, the compounds of Formula (I) of this invention can be synthesized following the general procedure as described in Reaction Scheme 2 where W is —N($R^5$)C(O)—, and p, X, Y, V, $R^1$, $R^2$, $R^3$, $R^4$ and $R^5$ are defined as in the Specification unless specifically defined otherwise.

REACTION SCHEME 2

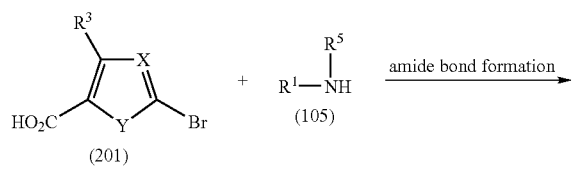

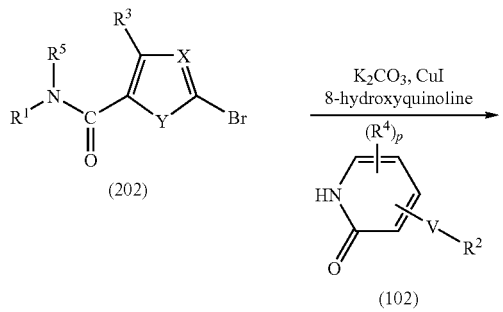

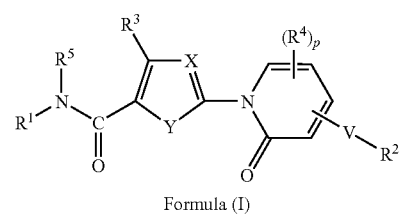

Formula (I)

The starting materials for the above reaction scheme are commercially available or can be prepared according to methods known to one skilled in the art or by methods disclosed herein. In general, the compounds of the invention are prepared in the above reaction scheme as follows:

The starting compound (201) undergoes coupling reaction with amine (105) under standard amide bond formation conditions known to one skilled in the art to afford compound (202). Compound (202) is then coupled with compound (102) under metal catalyzed reaction conditions to generate compounds of Formula (I) where W is —N($R^5$)C(O)—.

Alternatively, the compounds of Formula (I) of this invention can be synthesized following the general procedure as described in Reaction Scheme 3 where W is —N($R^5$)C(O)—, V is —O— or direct bond and p, X, Y, $R^1$, $R^2$, $R^3$, $R^4$ and $R^5$ are defined as in the Specification unless specifically defined otherwise. R' and R" are protecting groups.

REACTION SCHEME 3

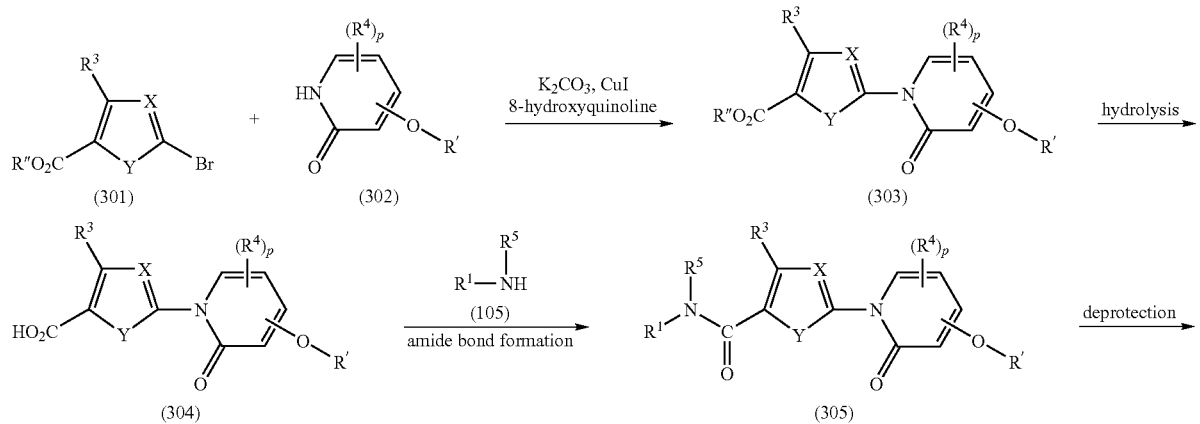

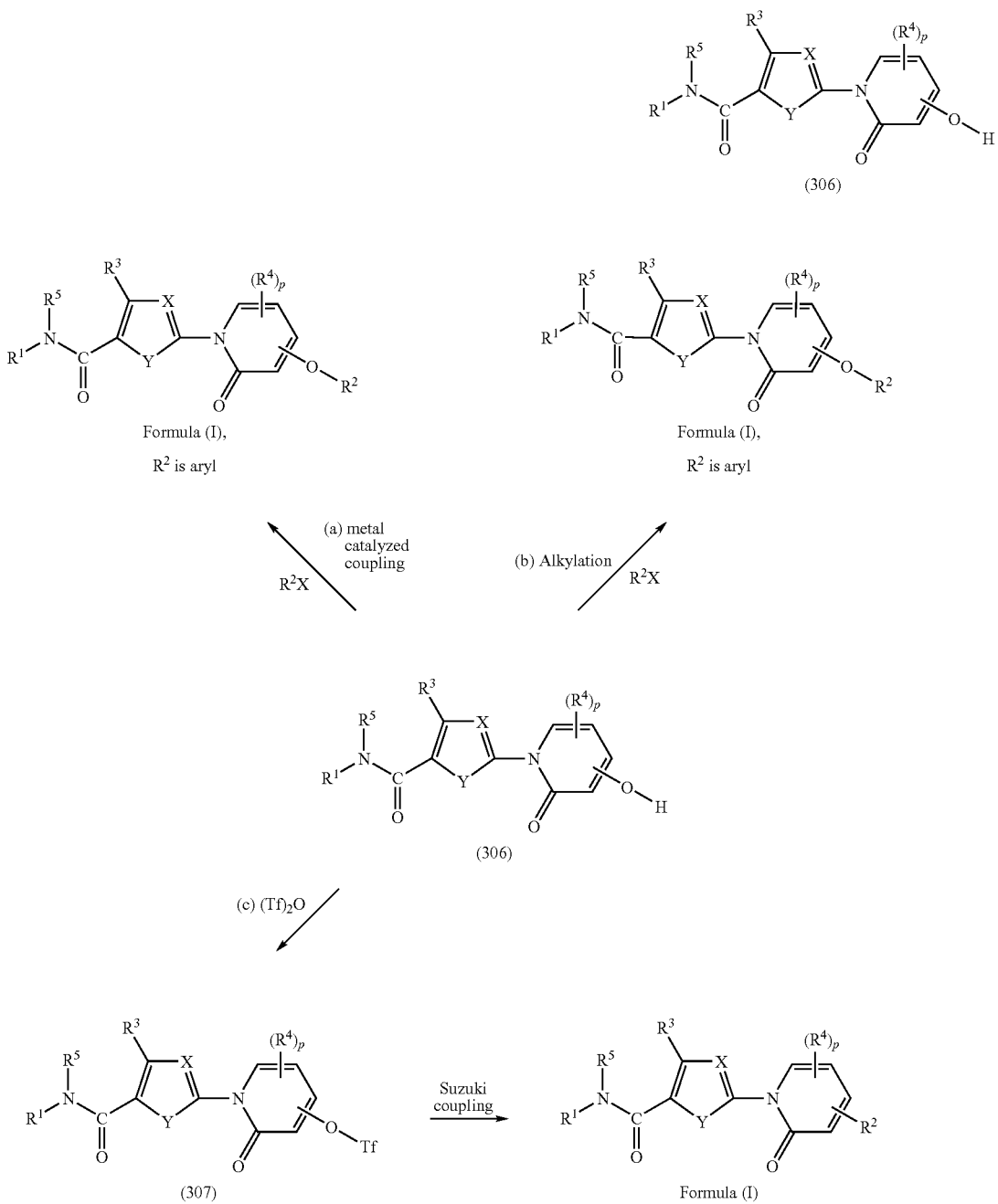

The starting materials for the above reaction scheme are commercially available or can be prepared according to methods known to one skilled in the art or by methods disclosed herein. In general, the compounds of the invention are prepared in the above reaction scheme as follows:

Compound (301) is coupled with compound (302) under metal catalyzed reaction conditions to generate compound (303) which undergoes a standard hydrolysis procedure known to one skilled in the art to generate the carboxylic acid (304). Coupling between compound (304) and amine (105) under standard amide bond formation conditions known to one skilled in the art affords the compound (305). Deprotection of the R' group (R'=benzyl) under palladium catalyzed hydrogenation conditions known to one skilled in the art affords compound (306). Compound (306) is used as a key intermediate to generate compounds of Formula (I) under the conditions of (a) metal catalyzed coupling reaction when $R^2$ is aryl, or (b) alkylation when $R^2$ is alkyl or (c) triflate formation to generate compound (307), followed by Suzuki coupling.

Alternatively, the compounds of Formula (I) of this invention can be synthesized following the general procedure as described in Reaction Scheme 4 where W is —N($R^5$)C(O)—, V is —N(H)C(O)— and p, X, Y, R', $R^2$, $R^3$, $R^4$ and $R^5$ are defined as in the Specification unless specifically defined otherwise. R" is a protecting group.

REACTION SCHEME 4

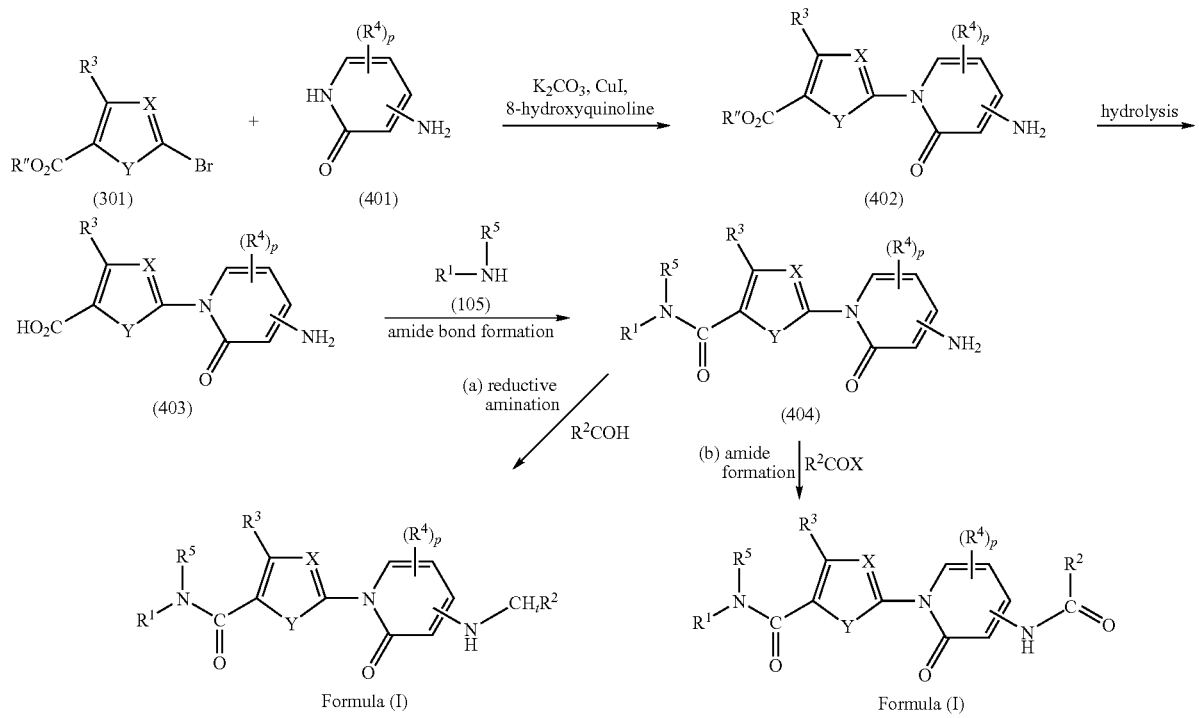

The starting materials for the above reaction scheme are commercially available or can be prepared according to methods known to one skilled in the art or by methods disclosed herein. In general, the compounds of the invention are prepared in the above reaction scheme as follows:

Compound (301) is coupled with compound (401) under metal catalyzed reaction conditions to generate compound (402) which undergoes a standard hydrolysis procedure known to one skilled in the art to generate the carboxylic acid (403). Coupling between compound (403) and amine (105) under standard amide bond formation conditions known to one skilled in the art affords the compound (404). Compound (404) is used as a key intermediate to generate compounds of Formula (I) under the conditions of (a) reductive amination or (b) amide bond formation.

Although anyone skilled in the art is capable of preparing the compounds of the invention according to the general techniques disclosed above, more specific details on synthetic techniques for compounds of the invention are provided elsewhere in this specification for convenience. Again, all reagents and reaction conditions employed in synthesis are known to those skilled in the art and are available from ordinary commercial sources.

Preparation 1

Preparation of 4-Phenylpyridin-2-ol

A solution of 4-phenylpyridine-1-oxide (2.00 g, 0.012 mol) in acetic anhydride (6 mL) was heated at reflux for 48 hours. The reaction mixture was cooled to ambient temperature, diluted with ethyl acetate (80 mL) and washed with saturated aqueous sodium bicarbonate (2×15 mL) and brine (15 mL). The organic layer was dried over anhydrous sodium sulfate, filtered and concentrated in vacuo. The residue was dissolved in methanol (20 mL) and potassium carbonate (0.32 g, 0.002 mol) was added to the solution. The reaction mixture was stirred at ambient temperature for 1 hour, then diluted with chloroform (100 mL) and filtered through Celite. The filtrate was concentrated in vacuo. The residue was dissolved in a mixture of methanol/chloroform 1/10 (30 mL). The title compound was precipitated with the addition of hexanes (30 mL) as a white solid which was collected by filtration (1.20 g, 60%): $^1$H NMR (300 MHz, DMSO-d$_6$) δ 7.66-7.62 (m, 2H), 7.48-7.37 (m, 4H), 6.51 (d, J=1.2 Hz, 1H), 6.44 (dd, J=6.7, 1.8 Hz, 1H); MS (ES+) m/z 172.5 (M+1).

Preparation 2

Preparation of N-Benzyl-2-bromo-4-methylthiazole-5-carboxamide

To a mixture of 2-bromo-4-methylthiazole-5-carboxylic acid (10.00 g, 45.03 mmol) and 1-(3-dimethyl)aminopropyl)-3-ethylcarbodiimide hydrochloride (12.09 g, 63.04 mmol) in tetrahydrofuran (170 mL) under nitrogen atmosphere was added diisopropylethylamine (17.46 g, 135.0 mmol). After the mixture was stirred at ambient temperature for 30 minutes, 1-hydroxybenzotriazole (8.52 g, 63.04 mmol) and benzylamine (6.76 g, 6.88 mL, 63.04 mmol) were added. The mixture was stirred at ambient temperature for 16 hours and then concentrated in vacuo. The residue was dissolved in dichloromethane (500 mL), washed with water (2×100 mL) and brine (2×100 mL). The organic layer was dried over anhydrous sodium sulfate and filtered. The filtrate was concentrated in vacuo. The residue was purified by column chromatography (ethyl acetate/petroleum ether, 2/1) to afford the title compound (11.91 g, 85%): $^1$H NMR (300 MHz, DMSO- $d_6$) δ 9.92 (t, J=6.0 Hz, 1H), 7.34-7.25 (m, 5H), 4.46 (d, J=6.0 Hz, 2H), 2.53 (s, 3H); MS (ES+) m/z 298.1 (M+1), 300.1 (M+1).

Preparation 3

Preparation of 3-(Benzyloxy)pyridin-2-ol

To a stirred solution of potassium hydroxide (2.52 g, 45.00 mmol) in methanol (30 mL), was added pyridine-2,3-diol (5.00 g, 45.0 mmol) in 3 portions and a clear red solution was obtained. To this clear red solution was added benzyl bromide (7.70 g, 5.35 mL, 45.00 mmol). The reaction mixture was kept stirring at ambient temperature for 30 minutes, then at 40° C. for 2 hours. The solvent was removed in vacuo and the residue was dissolved in dichloromethane (100 mL), and washed with water (100 mL). The organic layer was dried over anhydrous sodium sulfate and filtered. The filtrate was concentrated in vacuo. The residue was recrystallized from methanol (20 mL) to afford the title compound (4.60 g, 51%): $^1$H NMR (300 MHz, DMSO-$d_6$) δ 11.63 (s, 1H), 7.44-7.33 (m, 5H), 6.96-6.88 (m, 2H), 6.07 (t, J=6.0 Hz, 1H), 5.00 (s, 2H); MS (ES+) m/z 202.2 (M+1).

Preparation 4

Preparation of 5-(Benzyloxy)pyridin-2(1H)-one

To a solution of 5-hydroxypyridin-2(1H)-one (4.44 g, 40.0 mmol) in methanol (50 mL) was added potassium hydroxide (2.64 g, 40.0 mmol). The reaction mixture was stirred for 30 minutes at ambient temperature, followed by the addition of benzyl bromide (5.2 mL, 44 mmol). The reaction mixture was kept stirring at ambient temperature for 2 hours and then heated at 45-50° C. for 1 hour. The solvent was removed in vacuo, and the residue was washed with water, dichloromethane and then recrystallized from methanol to afford the title compound (5.39 g, 67%): $^1$H NMR (300 MHz, DMSO-$d_6$) δ 11.08 (s, 1H), 7.42-7.26 (m, 6H), 7.09 (d, J=3.0 Hz, 1H), 6.30 (d, J=9.6 Hz, 1H), 4.89 (s, 2H); MS (ES+) m/z 202.3 (M+1).

Preparation 5

Preparation of 5-(Benzyloxy)isoquinolin-1(2H)-one

5-Hydroxyisoquinolin-1(2H)-one (0.65 g, 4.04 mmol) was added in portions to a solution of potassium hydroxide (0.23 g, 4.04 mmol) in methanol (15 mL). The mixture was stirred at ambient temperature for 10 minutes, then benzyl bromide (0.69 g, 0.48 mL, 4.04 mmol) was added. The mixture was stirred at ambient temperature for 30 minutes and then at 40° C. for 2 hours. The solvent was removed in vacuo. The residue was dissolved in dichloromethane (100 mL) and washed with water (100 mL). The organic layer was dried over anhydrous sodium sulfate and filtered. The filtrate was concentrated in vacuo. The residue was recrystallized from methanol (10 mL) to afford the title compound (0.40 g, 40%): mp 165-168° C.; MS (ES+) m/z 252.1 (M+1).

Preparation 6

Preparation of 6-(Benzyloxy)quinolin-2(1H)-one

Following the synthetic procedure as described in Preparation 5, making variations only as required to use 6-hydroxyquinolin-2(1H)-one in place of 5-hydroxyisoquinolin-1 (2H)-one, the title compound was obtained (0.42 g, 42%): MS (ES+) m/z 252.2 (M+1).

Preparation 7

Preparation of N-Benzyl-5-bromothiophene-3-carboxamide

A. To a stirred solution of 3-thiophenecarboxylic acid (1.00 g, 7.80 mmol) in glacial acetic acid (9 mL) at ambient temperature under nitrogen atmosphere was slowly added bromine (0.39 mL, 7.53 mmol) in glacial acetic acid (6 mL). The reaction mixture was stirred for 15 minutes, then quenched with cold water (50 mL). The precipitate was filtered, washed with water and dried in vacuum oven at 50° C. to afford 5-bromo-3-thiophenecarboxylic acid as a colorless solid (0.78 g, 50%): mp 133-135° C.; $^1$H NMR (300 MHz, CDCl$_3$) δ 8.12 (d, J=1.5 Hz, 1H), 7.51 (d, J=1.5 Hz, 1H).

B. To a stirred solution of 5-bromo-3-thiophenecarboxylic acid (0.50 g, 2.42 mmol) in N,N-dimethylformamide (5 mL) was added N,N-diisopropylethylamine (1.30 mL, 7.46 mmol), 1-hydroxybenzotriazole (0.49 g, 3.61 mmol), and 1-ethyl-3-(3-dimethylaminopropyl)carbodiimide hydrochloride (0.69 g, 3.62 mmol). Benzylamine (0.26 mL, 2.41 mmol) was added 5 minutes later. The reaction mixture was stirred at ambient temperature for 16 h, then diluted with ethyl acetate (75 mL). The organic layer was washed with 10% aqueous hydrochloric acid (25 mL), saturated aqueous sodium bicarbonate (2×25 mL), dried over sodium sulfate and filtered. The filtrate was concentrated in vacuo to afford the title compound as a colorless solid (0.57 g, 80%): $^1$H NMR (300 MHz, CDCl$_3$) δ 7.77 (d, J=1.6 Hz, 1H), 7.37-7.31 (m, 6H), 6.14 (br s, 1H), 4.59 (d, J=5.7 Hz, 2H).

Preparation 8

Preparation of N-Benzyl-5-bromo-3-methylthiophene-2-carboxamide

To a stirred solution of N-benzyl-3-methylthiophene-2-carboxamide (0.74 g, 3.18 mmol) in acetonitrile (15 mL) was added N-bromosuccinimide (0.57 g, 3.18 mmol). The reaction mixture was stirred for 16 h, and then concentrated in vacuo. The residue was purified by column chromatography eluting with 5-35% ethyl acetate in hexane to afford the title compound as a colorless solid (0.69 g, 69%): $^1$H NMR (300 MHz, CDCl$_3$) δ 7.38-7.30 (m, 5H), 6.87 (s, 1H), 4.59 (d, J=5.6 Hz, 2H), 2.46 (s, 3H); MS (ES+) m/z 310.1 (M+1), 312.1 (M+1).

Preparation 9

Preparation of 2-Cyclopropylethyl 4-Methylbenzenesulfonate

To a stirred solution of 2-cyclopropylethanol (5.00 g, 58.05 mmol) in dichloromethane (20 mL) was added pyridine (7.03 mL, 86.92 mmol), followed by p-toluenesulfonyl chloride (10.50 g, 55.07 mmol). The reaction mixture was stirred for 16 h, and then partitioned between dichloromethane (100 mL) and water (50 mL). The organic layer was washed with 10% aqueous hydrochloric acid (50 mL), saturated aqueous sodium bicarbonate (50 mL) and brine (50 mL), dried over anhydrous sodium sulfate and filtered. The filtrate was concentrated in vacuo to afford 2-cyclopropylethyl 4-methylbenzenesulfonate as a colorless oil (11.90 g, 96%): $^1$H NMR (300

MHz, CDCl$_3$) δ 7.80 (d, J=8.3 Hz, 2H), 7.34 (d, J=8.3 Hz, 2H), 4.09 (t, J=6.6 Hz, 2H), 2.45 (s, 3H), 1.57-1.48 (m, 2H), 0.74-0.59 (m, 1H), 0.45-0.36 (m, 2H), 0.08-0.06 (m, 2H).

Preparation 10

Preparation of Phenethyl 4-Methylbenzenesulfonate

To a stirred solution of phenethyl alcohol (0.50 mL, 4.17 mmol) in pyridine (4 mL) at 0° C. was added p-toluenesulfonyl chloride (0.80 g, 4.18 mmol). The reaction mixture was stirred for 16 h, and then diluted with ethyl acetate (75 mL). The organic solution was washed with 10% aqueous hydrochloric acid (2×25 mL), saturated aqueous sodium bicarbonate (50 mL) and brine (25 mL), then dried over anhydrous sodium sulfate and filtered. The filtrate was concentrated in vacuo and the residue was purified by column chromatography eluting with 0-20% ethyl acetate in hexane to afford the title compound as a light yellow liquid (0.59 g, 51%): $^1$H NMR (300 MHz, CDCl$_3$) δ 7.69 (d, J=8.3 Hz, 2H), 7.31-7.20 (m, 5H), 7.11 (dd, J=7.4, 1.7 Hz, 2H), 4.21 (t, J=7.1 Hz, 2H), 2.96 (t, J=7.1 Hz, 2H), 2.43 (s, 3H); MS (ES+) m/z 299.2 (M+23).

Preparation 11

Preparation of 2-Hydroxy-N-phenylisonicotinamide

A. To a solution of 2-methoxyisonicotinic acid (2.00 g, 13.06 mmol) in anhydrous tetrahydrofuran (80 mL) was added 4-methyl morpholine (1.84 g, 18.28 mmol). After cooling to 0° C., isobutyl chloroformate (2.31 g, 16.98 mmol) was added to the reaction mixture. The reaction mixture was stirred at ambient temperature for 6 hours, followed by the addition of aniline (1.70 g, 18.28 mmol). The resulting mixture was stirred at ambient temperature for 16 hours. The solvent was removed in vacuo. The residue was dissolved in ethyl acetate (150 mL) and washed with saturated aqueous sodium bicarbonate (2×50 mL) and brine (50 mL). The organic layer was dried over anhydrous sodium sulfate, filtered and the filtrate was concentrated in vacuo to afford 2-methoxy-N-phenylisonicotinamide (2.50 g, 86%) as a colorless solid: $^1$H NMR (300 MHz, CDCl$_3$) δ 11.85 (s, 1H), 10.31 (s, 1H), 7.75-7.60 (m, 2H), 7.47 (d, J=4.6 Hz, 1H), 7.35-7.20 (m, 2H), 7.12-7.04 (m, 1H), 6.83-6.80 (m, 1H), 6.54-6.42 (m, 1H); MS (ES+) m/z 229.2 (M+1).

B. To a solution of 2-methoxy-N-phenylisonicotinamide (1.00 g, 4.38 mmol) in anhydrous chloroform (60 mL) was added iodotrimethylsilane (17.50 g, 87.50 mmol). The reaction mixture was stirred at reflux for 16 hours. After cooling to ambient temperature, methanol (10 mL) was added dropwise to quench the reaction. The solvent was removed in vacuo. The residue was dissolved in ethyl acetate (300 mL) and washed with saturated aqueous sodium bicarbonate solution (2×100 mL) and brine (150 mL). The organic layer was dried over anhydrous sodium sulfate, filtered and concentrate in vacuo. The brown crude product was recrystallised from ethyl acetate and methanol to afford the title compound as a colourless solid (0.35 g, 19%): $^1$H NMR (300 MHz, DMSO-d$_6$) δ 11.88 (br s, 1H), 10.31 (s, 1H), 7.73-7.68 (m, 2H), 7.47 (d, J=6.8 Hz, 1H), 7.31 (t, J=7.9 Hz, 2H), 7.10-7.05 (m, 1H), 6.81 (s, 1H), 6.49 (dd, J=6.8, 1.7 Hz, 1H); MS (ES+) m/z 215.2 (M+1).

Preparation 12

Preparation of 2-Oxo-N-phenyl-1,2-dihydropyridine-3-carboxamide

To a solution of 2-oxo-1,2-dihydropyridine-3-carboxylic acid (1.00 g, 7.18 mmol) in anhydrous tetrahydrofuran (40 mL) was added 4-methyl morpholine (1.01 g, 10.06 mmol). After cooling to 0° C., isobutyl chloroformate (1.27 g, 9.34 mmol) was added to the reaction mixture. The mixture was stirred at ambient temperature for 6 hours followed by the addition of aniline (0.87 g, 9.34 mmol). The resulting mixture was stirred at ambient temperature for 16 hours. The solvent was removed in vacuo. The residue was dissolved in ethyl acetate (100 mL), and washed with saturated aqueous sodium bicarbonate (2×50 mL) and brine (50 mL). The organic layer was dried over anhydrous sodium sulfate, filtered and concentrated in vacuo to afford the title compound as a colorless solid (1.50 g, 97%): $^1$H NMR (300 MHz, DMSO-d$_6$) δ 12.71 (br s, 1H), 12.14 (s, 1H), 8.46-8.38 (m, 1H), 7.80-7.52 (m, 1H), 7.65-7.62 (m, 2H), 7.35-7.29 (m, 2H), 7.10-6.95 (m, 1H), 6.58-6.45 (m, 1H); MS (ES+) m/z 215.2 (M+1).

Preparation 13

Preparation of Ethyl 2-Bromo-1,4-dimethyl-1H-imidazole-5-carboxylate and Ethyl 2-Bromo-1,5-dimethyl-1H-imidazole-4-carboxylate A. To a stirred suspension of ethyl 4-methyl-1H-imidazole-5-carboxylate (2.00 g, 13.0 mmol) in acetonitrile (25 mL) and chloroform (25 mL) was added N-bromosuccinimide (2.31 g, 13.0 mmol). The reaction mixture was stirred under nitrogen atmosphere for 20 h, then concentrated in vacuo. The residue was dissolved in ethyl acetate (100 mL) and washed with saturated aqueous sodium bicarbonate (50 mL). The organic layer was dried over sodium sulfate, filtered and concentrated in vacuo. The residue was purified by column chromatography eluting with 50% ethyl acetate in hexanes to afford ethyl 2-bromo-4-methyl-1H-imidazole-5-carboxylate as a light yellow solid (1.88 g, 62%): $^1$H NMR (300 MHz, CDCl$_3$) δ 4.35 (q, J=7.1 Hz, 2H), 2.51 (s, 3H), 1.37 (t, J=7.1 Hz, 3H); MS (ES+) m/z 233.1 (M+1), 235.1 (M+1).

B. To a stirred suspension of ethyl 2-bromo-4-methyl-1H-imidazole-5-carboxylate (0.90 g, 3.86 mmol) and potassium carbonate (1.07 g, 7.74 mmol) in N,N-dimethylformamide (15 mL) under nitrogen atmosphere was added iodomethane (0.73 mL, 11.6 mmol). The reaction mixture was stirred for 1.5 h, and diluted with ethyl acetate (75 mL). The organic layer was washed with water (25 mL) and brine (25 mL), dried over sodium sulfate, filtered and concentrated in vacuo. The residue was purified by column chromatography eluting with 10-60% ethyl acetate in hexanes to afford the title compounds. First fraction: ethyl 2-bromo-1,4-dimethyl-1H-imidazole-5-carboxylate (0.61 g, 64%): $^1$H NMR (300 MHz, CDCl$_3$) δ 4.33 (q, J=7.1 Hz, 2H), 3.86 (s, 3H), 2.46 (s, 3H), 1.38 (t, J=7.1 Hz, 3H); MS (ES+) m/z 247.1 (M+1). Second fraction: ethyl 2-bromo-1,5-dimethyl-1H-imidazole-4-carboxylate (0.30 g, 32%): $^1$H NMR (300 MHz, CDCl$_3$) δ 4.35 (q, J=7.1 Hz, 2H), 3.54 (s, 3H), 2.56 (s, 3H), 1.38 (t, J=7.1 Hz, 3H); MS (ES+) m/z 247.1 (M+1).

Preparation 14

Preparation of 2-Bromo-N-(4-fluorobenzyl)-4-methylthiazole-5-carboxamide

To a mixture of 2-bromo-4-methylthiazole-5-carboxylic acid (2.00 g, 9.00 mmol) in anhydrous tetrahydrofuran (40 mL) was added N,N-diisopropylethylamine (4.67 mL, 27.0 mmol) and 1-ethyl-3-(3-dimethylaminopropyl)carbodiimide hydrochloride (2.41 g, 12.6 mmol). The reaction mixture was stirred at ambient temperature for 30 minutes, followed by the addition of 1-hydroxybenzotriazole (1.70 g, 12.60 mmol) and (4-fluorophenyl)methanamine (2.50 g, 12.60 mmol). The reaction mixture was stirred at ambient temperature for 18 hours. The solvent was concentrated to half in vacuo. The residue was diluted with ethyl acetate (200 mL), washed sequentially with 10% aqueous hydrochloric acid (50 mL), saturated bicarbonate solution (50 mL) and brine (100 mL). The organic layer was dried over anhydrous sodium sulfate, filtered and concentrated in vacuo. The residue was recrystallized in ethyl acetate and hexane to afford the title compound as a colorless solid (2.38 g, 81%): $^1$H NMR (300 MHz, CDCl$_3$) δ 7.30-7.26 (m, 2H), 7.05-7.00 (m, 2H), 5.99-5.87 (m, 1H), 4.54 (d, J=5.7 Hz, 2H), 2.63 (s, 3H).

Preparation 14.1

Preparation of 2-Bromo-N-(3,4-difluorobenzyl)-4-methylthiazole-5-carboxamide

Following the procedure as described in Preparation 15, making variations only as requires to use (3,4-difluorophenyl)methanamine to replace (4-fluorophenyl)-methanamine to react with 2-bromo-4-methylthiazole-5-carboxylic acid, the title compound was obtained as a colorless solid in 50% yield: $^1$H NMR (300 MHz, CDCl$_3$) δ 7.16-7.01 (m, 3H), 6.08-5.94 (m, 1H), 4.52 (d, J=5.9 Hz, 2H), 2.64 (s, 3H); MS (ES+) m/z 347.2 (M+1), 349.2 (M+3).

Preparation 15

Preparation of 2-Bromo-4-methyl-N-(pyridin-3-ylmethyl)thiazole-5-carboxamide

To a solution of 2-bromo-4-methylthiazole-5-carboxylic acid (10.00 g, 45.00 mmol) and 4-methylmorpholine (6.5 mL, 59.0 mmol) in tetrahydrofuran (150 mL) was added isobutyl chloroformate (6.5 mL, 49.6 mmol) at 0° C. The resulting mixture was stirred at room temperature for 1 hour then 3-(aminomethyl)pyridine (5.2 mL, 51.4 mmol) was added. The reaction mixture was stirred at ambient temperature for 17 hours, then concentrated in vacuo. The residue was purified by column chromatography to afford 2-bromo-4-methyl-N-(pyridin-3-ylmethyl)thiazole-5-carboxamide in 52% yield (7.3 g): $^1$H NMR (300 MHz, CDCl$_3$) δ 8.39-8.80 (m, 2H), 7.80-7.72 (m, 1H), 7.40-7.35 (m, 1H), 6.47 (br s, 1H), 4.60 (d, J=6.0 Hz, 2H), 2.64 (s, 3H); MS (ES+) m/z 312.1, 314.1 (M+1).

Preparation 16

Preparation of 4-(Phenoxymethyl)pyridin-2(1H)-one

A. To a solution of tributylphosphine (4.57 g, 22.63 mmol) in anhydrous tetrahydrofuran (20 mL) was added diisopropyl azodicarboxylate (4.57 g, 22.63 mmol) at 0° C. The reaction mixture was stirred for 10 minutes at 0° C., then added to a solution of (2-chloropyridin-4-yl)methanol and phenol in anhydrous tetrahydrofuran (50 mL) at 0° C. The reaction mixture was stirred at 0° C. for 20 minutes then at ambient temperature for 16 hours. The reaction was quenched with saturated ammonium chloride solution (10 mL). The solvent was evaporated in vacuo. The residue was diluted with ethyl acetate (350 mL), washed with 1 N sodium hydroxide solution (3×40 mL), dried over anhydrous sodium sulfate, filtered and concentrated in vacuo. The residue was purified by column chromatography eluted with ethyl acetate/hexane (1/9) to afford 2-chloro-4-(phenoxymethyl)pyridine as a gummy solid in 61% yield (2.34 g): $^1$H NMR (300 MHz, CDCl$_3$) δ 8.36 (d, J=5.1 Hz, 1H), 7.40 (s, 1H), 7.32-7.24 (m, 3H), 7.01-6.91 (m, 3H), 5.05 (s, 2H); MS (ES+) m/z 220.2 (M+1).

B. To a solution of 2-chloro-4-(phenoxymethyl)pyridine (2.34 g, 10.68 mmol) in anhydrous methanol (30 mL) in a steel bomb was added sodium hydroxide (3.20 g, 80.11 mmol). The reaction mixture was stirred at 170° C. for 16 hours, cooled to 0° C. and neutralized with cold concentrated hydrochloric acid, followed by the addition of methanol (10 mL) and filtration. The filtrate was concentrated in vacuo and the residue was washed with methanol and hexane. The title compound was obtained as a colorless solid in 93% (2 g): $^1$H NMR (300 MHz, CDCl$_3$) δ 13.00 (br s, 1H), 7.35-7.25 (m, 3H), 6.99-6.90 (m, 3H), 6.64 (s, 1H), 6.34 (d, J=6.6 Hz, 1H), 4.93 (s, 2H); MS (ES+) m/z 202.2 (M+1).

Preparation 17

Preparation of N-Benzyl-3-methylfuran-2-carboxamide

To a mixture of 3-methylfuran-2-carboxylic acid (0.79 g, 6.28 mmol), 1-hydroxybenzotriazole (1.27 g, 9.42 mmol) and 1-ethyl-3-(3-dimethylaminopropyl)-carbodiimide hydrochloride (1.81 g, 9.42 mmol) in N,N-dimethylformamide (6 mL) was added N,N-diisopropylethylamine (3.30 mL, 18.94 mmol) and benzylamine (0.69 mL, 6.28 mmol). The reaction mixture was stirred for 16 hours, and then diluted with ethyl acetate (75 mL). The organic layer was washed with 10% aqueous hydrochloric acid (2×25 mL), saturated aqueous sodium bicarbonate (2×25 mL), dried over sodium sulfate, filtered and concentrated in vacuo to afford N-benzyl-3-methylfuran-2-carboxamide as a light brown solid (0.57 g, 80%): $^1$H NMR (300 MHz, CDCl$_3$) δ 7.37-7.28 (m, 5H), 7.27 (d, J=1.5 Hz, 1H), 6.61 (br s, 1H), 6.34 (d, J=1.5 Hz, 1H), 4.59 (d, J=5.9 Hz, 2H), 2.42 (s, 3H); MS (ES+) m/z 216.2 (M+1).

Preparation 17.1

Preparation of N-(4-Fluorobenzyl)-3-methylthiophene-2-carboxamide

Following the procedure as described in Preparation 18, making variations only as required to use 3-methylthiophene-2-carboxylic acid in place of 3-methylfuran-2-carboxylic acid to react with 4-fluorobenzylamine in place of benzylamine, N-(4-fluorobenzyl)-3-methylthiophene-2-carboxamide was obtained as a colorless solid in 94% yield: $^1$H NMR (300 MHz, CDCl$_3$) δ 7.37-7.26 (m, 3H), 7.08-7.00 (m, 2H), 6.90 (d, J=5.0 Hz, 1H), 6.09 (br s, 1H), 4.57 (d, J=5.8 Hz, 2H), 2.52 (s, 3H); MS (ES+) m/z 250.2 (M+1).

Preparation 17.2

Preparation of N-(3-Fluorobenzyl)-3-methylthiophene-2-carboxamide

Following the procedure as described in Preparation 18, making variations only as required to use 3-methylthiophene-2-carboxylic acid in place of 3-methylfuran-2-carboxylic acid to react with 3-fluorobenzylamine in place of benzylamine, N-(3-fluorobenzyl)-3-methylthiophene-2-carboxamide was obtained as a colorless solid in 96% yield: $^1$H NMR (300 MHz, CDCl$_3$) δ 7.35-7.25 (m, 2H), 7.15-6.94 (m, 3H), 6.90 (d, J=5.0 Hz, 1H), 6.14 (br s, 1H), 4.61 (d, J=5.9 Hz, 2H), 2.54 (s, 3H); MS (ES+) m/z 250.2 (M+1).

Preparation 17.3

Preparation of N-ethyl-3-methylthiophene-2-carboxamide

Following the procedure as described in Preparation 18, making variations only as required to use 3-methylthiophene-2-carboxylic acid in place of 3-methylfuran-2-carboxylic acid to react with ethylamine in place of benzylamine, N-ethyl-3-methylthiophene-2-carboxamide was obtained as a colorless liquid in 92% yield: $^1$H NMR (300 MHz, CDCl$_3$) δ 7.24 (d, J=5.0 Hz, 1H), 6.88 (d, J=5.0 Hz, 1H), 5.77 (br s, 1H), 3.51-3.40 (m, 2H), 2.51 (s, 3H), 1.24 (t, J=7.3 Hz, 3H); MS (ES+) m/z 170.2 (M+1).

Preparation 18

Preparation of N-Benzyl-5-bromo-3-methylfuran-2-carboxamide

To a stirred solution of N-benzyl-3-methylfuran-2-carboxamide (1.18 g, 5.49 mmol) in acetonitrile (25 mL) was added N-bromosuccinimide (0.98 g, 5.49 mmol). The reaction mixture was stirred for 16 hours, and then partitioned between ethyl acetate (100 mL) and water (75 mL). The organic layer was washed with 1 N sodium hydroxide solution (50 mL) and brine (50 mL), dried over sodium sulfate, filtered and concentrated in vacuo. The residue was purified by column chromatography eluted with 0-20% ethyl acetate in hexanes to afford N-benzyl-5-bromo-3-methylfuran-2-carboxamide as a colorless solid (0.18 g, 11%): $^1$H NMR (300 MHz, CDCl$_3$) δ 7.38-7.27 (m, 5H), 6.54 (br s, 1H), 6.28 (s, 1H), 4.58 (d, J=5.9 Hz, 2H), 2.40 (s, 3H); MS (ES+) m/z 294.1 (M+1), 296.1 (M+1).

Preparation 18.1

Preparation of 5-bromo-N-(4-fluorobenzyl)-3-methylthiophene-2-carboxamide

Following the procedure as described in Preparation 19, making variations only as required to use N-(4-fluorobenzyl)-3-methylthiophene-2-carboxamide) in place of N-benzyl-3-methylfuran-2-carboxamide to react with N-bromosuccinimide, 5-bromo-N-(4-fluorobenzyl)-3-methylthiophene-2-carboxamide was obtained as a colorless solid in 87% yield: $^1$H NMR (300 MHz, CD$_3$CN) δ 7.38-7.32 (m, 2H), 7.10-7.03 (m, 2H), 6.97 (s, 1H), 4.45 (d, J=6.1 Hz, 2H), 2.40 (s, 3H); MS (ES+) m/z 328.1 (M+1), 330.1 (M+1).

Preparation 18.2

Preparation of 5-Bromo-N-(3-fluorobenzyl)-3-methylthiophene-2-carboxamide

Following the procedure as described in Preparation 19, making variations only as required to use N-(3-fluorobenzyl)-3-methylthiophene-2-carboxamide) in place of N-benzyl-3-methylfuran-2-carboxamide to react with N-bromosuccinimide, 5-bromo-N-(3-fluorobenzyl)-3-methylthiophene-2-carboxamide was obtained as a colorless solid in 89% yield: $^1$H NMR (300 MHz, CD$_3$CN) δ 7.39-7.31 (m, 1H), 7.16 (d, J=7.6 Hz, 1H), 7.08 (d, J=10.2 Hz, 1H), 7.02 (dd, J=8.5, 2.5 Hz, 1H), 6.98 (s, 1H), 4.48 (d, J=6.1 Hz, 2H), 2.42 (s, 3H); MS (ES+) m/z 328.1 (M+1), 330.1 (M+1).

Preparation 18.3

Preparation of 5-bromo-N-ethyl-3-methylthiophene-2-carboxamide

Following the procedure as described in Preparation 19, making variations only as required to use N-ethyl-3-methylthiophene-2-carboxamide in place of N-benzyl-3-methylfuran-2-carboxamide to react with N-bromosuccinimide, 5-bromo-N-ethyl-3-methylthiophene-2-carboxamide was obtained as a colorless oil in 92% yield: $^1$H NMR (300 MHz, CDCl$_3$) δ 6.85 (s, 1H), 5.65 (br s, 1H), 3.48-3.38 (m, 2H), 2.45 (s, 3H), 1.22 (t, J=7.3 Hz, 3H); MS (ES+) m/z 248.1 (M+1), 250.1 (M+1).

Preparation 19

Preparation of ethyl 5-bromo-3-methylthiophene-2-carboxylate

A. To a stirred solution of 3-methylthiophene-2-carboxylic acid (1.84 g, 12.9 mmol) in ethanol (20 mL) was added thionyl chloride (0.94 mL, 12.9 mmol). The resulting reaction mixture was stirred at reflux for 20 h, and then allowed to cool to ambient temperature and concentrated in vacuo. The residue was taken up in ethyl acetate (200 mL) and washed with saturated aqueous sodium bicarbonate (2×100 mL). The organic layer was dried over sodium sulfate, filtered and concentrated in vacuo to afford ethyl 3-methylthiophene-2-carboxylate as light yellow liquid (1.89 g, 86%): $^1$H NMR (300 MHz, CDCl$_3$) δ 7.37 (d, J=5.0 Hz, 1H), 6.90 (d, J=5.0 Hz, 1H), 4.32 (q, J=7.1 Hz, 2H), 2.55 (s, 3H), 1.37 (t, J=7.1 Hz, 3H).

B. To a stirred solution of ethyl 3-methylthiophene-2-carboxylate (1.89 g, 11.10 mmol) in acetonitrile (20 mL) was added N-bromosuccinimide (1.98 g, 11.12 mml). The reaction mixture was stirred for 20 h, and then concentrated in vacuo. The residue was purified by column chromatography eluted with 0-5% ethyl acetate in hexanes to afford a mixture of ethyl 5-bromo-3-methylthiophene-2-carboxylate and ethyl 4-bromo-3-methylthiophene-2-carboxylate as colorless liquid (2.04 g, 72%): $^1$H NMR (300 MHz, CDCl$_3$) δ 6.89 (s, 1H), 4.39-4.26 (m, 2H), 2.55 (s, 3H), 1.43-1.31 (m, 3H).

Although anyone skilled in the art is capable of preparing the compounds of the invention according to the general techniques disclosed above, more specific details on synthetic techniques for compounds of the invention are provided elsewhere in this specification for convenience. Again, all reagents and reaction conditions employed in synthesis are known to those skilled in the art and are available from ordinary commercial sources.

The syntheses of compounds of this invention are illustrated by, but not limited to the following examples.

Example 1

Synthesis of N-benzyl-4-methyl-2-(2-oxo-4-phenylpyridin-1(2H)-yl)thiazole-5-carboxamide

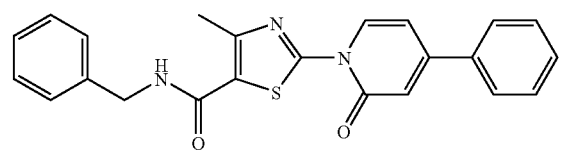 [SMILES: Cc1nc(-n2ccc(-c3ccccc3)cc2=O)sc1C(=O)NCc1ccccc1]

To a solution of 4-methyl-2-(2-oxo-4-phenylpyridin-1(2H)-yl)thiazole-5-carboxylic acid (0.20 g, 0.64 mmol) in anhydrous N,N-dimethylformamide (3 mL) was added 1-hydroxybenzotriazole (0.23 g, 1.67 mmol), N-(3-dimethylaminopropyl)-N'-ethylcarbodiimide (0.15 g, 0.77 mmol), N,N-diisopropylethylamine (0.11 g, 0.83 mmol), and benzylamine (0.084 mL, 0.77 mmol). The reaction mixture was stirred at ambient temperature for 5 hours and N,N-dimethylformamide was removed in vacuo. The residue was dissolved in ethyl acetate (15 mL) and washed with saturated aqueous sodium bicarbonate (2×5 mL) and brine (5 mL). The organic layer was dried over anhydrous sodium sulfate, filtered and concentrated in vacuo to afford the title compound as a white solid (0.12 g, 47%): mp 235-237° C. (ethyl acetate); $^1$H NMR (300 MHz, DMSO-d$_6$) δ 8.83 (t, J=5.8 Hz, 1H), 8.77 (d, J=7.6 Hz, 1H), 7.87-7.77 (m, 2H), 7.52-7.49 (m, 3H), 7.34-7.18 (m, 5H), 7.08-7.00 (m, 2H), 4.40 (d, J=5.8 Hz, 2H), 2.59 (s, 3H); $^{13}$C NMR (75 MHz, DMSO-d$_6$) δ 161.9, 160.4, 153.7, 151.4, 150.6, 139.9, 135.9, 131.6, 130.9, 129.7, 128.8, 127.8, 127.5, 127.3, 124.5, 43.2, 17.6; MS (ES+) m/z 402.5 (M+1).

Example 1.1

Synthesis of N-Benzyl-2-(4-(cyclopropylmethoxy)-2-oxopyridin-1(2H)-yl)-4-methylthiazole-5-carboxamide

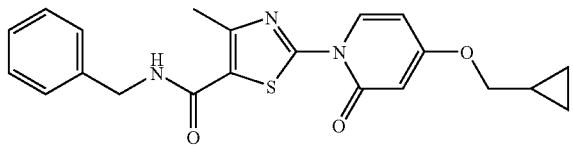 [SMILES: Cc1nc(-n2ccc(OCC3CC3)cc2=O)sc1C(=O)NCc1ccccc1]

Following the procedure as described in Example 1, making variations only as required to use 2-(4-(cyclopropylmethoxy)-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with benzylamine, the title compound was obtained as a white solid in 58% yield: mp 218-220° C. (hexane/ethyl acetate); $^1$H NMR (300 MHz, DMSO-d$_6$) δ 8.77 (t, J=5.9 Hz, 1H), 8.58 (d, J=8.1 Hz, 1H), 7.35-7.18 (m, 5H), 6.34 (dd, J=8.1, 2.7 Hz, 1H), 6.05 (d, J=2.7 Hz, 1H), 4.38 (d, J=5.9 Hz, 2H), 3.88 (d, J=7.2 Hz, 2H), 2.53 (s, 3H), 1.26-1.10 (m, 1H), 0.52-0.50 (m, 2H), 0.32-0.27 (m, 2H); $^{13}$C NMR (75 MHz, DMSO-d$_6$) δ 167.8, 161.9, 161.6, 153.8, 150.3, 139.9, 131.9, 128.7, 127.7, 127.2, 123.6, 104.4, 96.8, 73.9, 43.1, 17.5, 9.9, 3.6; MS (ES+) m/z 396.2 (M+1).

Example 1.2

Synthesis of N-Benzyl-2-(4-methoxy-2-oxopyridin-1(2H)-yl)-4-methylthiazole-5-carboxamide

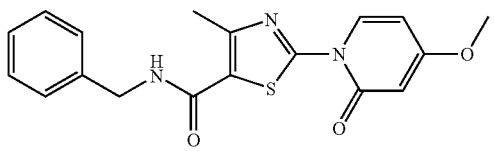 [SMILES: COc1ccn(-c2nc(C)c(C(=O)NCc3ccccc3)s2)c(=O)c1]

Following the procedure as described in Example 1, making variations only as required to use 2-(4-methoxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with benzylamine, the title compound was obtained as a colorless solid in 17% yield: mp 205-208° C. (hexane/ethyl acetate); $^1$H NMR (300 MHz, DMSO-d$_6$) δ 8.78 (t, J=6.0 Hz, 1H), 8.59 (d, J=8.1 Hz, 1H), 7.35-7.17 (m, 5H), 6.33 (dd, J=8.1, 2.7 Hz, 1H), 6.11 (d, J=2.7 Hz, 1H), 4.38 (d, J=6.0 Hz, 2H), 3.81 (s, 3H), 2.54 (s, 3H); $^{13}$C NMR (75 MHz, DMSO-d$_6$) δ 168.6, 161.9, 161.6, 153.9, 150.3, 139.9, 132.0, 128.7, 127.2, 123.7, 104.2, 86.5, 56.8, 43.1, 17.5; MS (ES+) m/z 356.2 (M+1).

Example 1.3

Synthesis of N-Benzyl-2-(4-(2-cyclopropylethoxy)-2-oxopyridin-1(2H)-yl)-4-methylthiazole-5-carboxamide

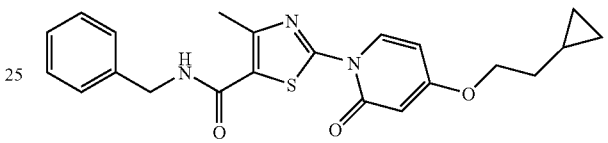 [SMILES: Cc1nc(-n2ccc(OCCC3CC3)cc2=O)sc1C(=O)NCc1ccc(F)cc1]

Following the procedure as described in Example 1, making variations only as required to use 2-(4-(2-cyclopropylethoxy)-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with benzylamine, the title compound was obtained as a colorless solid in 17% yield: mp 172-174° C. (hexane/ethyl acetate); $^1$H NMR (300 MHz, CDCl$_3$) δ 8.64 (d, J=8.1 Hz, 1H), 7.37-7.26 (m, 5H), 6.16 (dd, J=8.1, 2.5 Hz, 1H), 6.09 (t, J=5.6 Hz, 1H), 5.97 (d, J=2.5 Hz, 1H), 4.58 (d, J=5.6 Hz, 2H), 4.03 (t, J=6.6 Hz, 2H), 2.68 (s, 3H), 1.68 (q, J=6.6 Hz, 2H), 0.89-0.72 (m, 1H), 0.52-0.46 (m, 2H), 0.13-0.08 (m, 2H); $^{13}$C NMR (75 MHz, CDCl$_3$) δ 167.8, 162.2, 162.1, 153.6, 152.1, 137.7, 131.3, 128.8, 127.9, 127.7, 122.2, 104.1, 96.6, 69.1, 44.1, 33.6, 17.3, 7.5, 4.2; MS (ES+) m/z 410.2 (M+1).

Example 1.4

Synthesis of 2-(4-(2-Cyclopropylethoxy)-2-oxopyridin-1(2H)-yl)-N-(4-fluorobenzyl)-4-methylthiazole-5-carboxamide

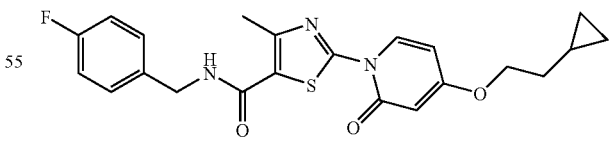

Following the procedure as described in Example 1, making variations only as required to use 4-fluorobenzylamine in place of benzylamine to react with 2-(4-(2-cyclopropylethoxy)-2-oxopyridin-1(2H)-yl)-4-methylthiazole-5-carboxylic acid, the title compound was obtained as a colorless solid in 30% yield: mp 172-174° C. (ethyl acetate); $^1$H NMR (300 MHz, CDCl$_3$) δ 8.64 (d, J=8.1 Hz, 1H), 8.32-8.27 (m, 2H), 7.05-7.00 (m, 2H), 6.17-6.08 (m, 2H), 5.97 (t, J=2.5 Hz, 1H), 4.54 (d, J=5.7 Hz, 2H), 4.03 (t, J=6.6 Hz, 2H), 2.67 (s, 3H), 1.68 (q, J=6.6 Hz, 2H), 0.87-0.93 (m, 1H), 0.54-0.46 (m, 2H), 0.13-0.08 (m, 2H); $^{13}$C NMR (75 MHz, CDCl$_3$) δ 167.9, 163.9, 162.2, 160.6, 153.6, 152.4, 133.6, 131.3, 129.6, 122.0, 115.8, 104.2, 96.6, 69.1, 43.3, 33.6, 17.3, 7.5, 4.2; MS (ES+) m/z 428.2 (M+1).

Example 1.5

Synthesis of 2-(4-(2-Cyclopropylethoxy)-2-oxopyridin-1(2H)-yl)-4-methyl-N-(pyridin-3-ylmethyl)thiazole-5-carboxamide

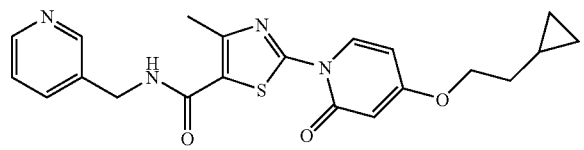 [SMILES: Cc1nc(-n2ccc(OCCC3CC3)cc2=O)sc1C(=O)NCc1cccnc1]

Following the procedure as described in Example 1, making variations only as required to use pyridin-3-ylmethanamine in place of benzylamine to react with 2-(4-(2-cyclopropylethoxy)-2-oxopyridin-1(2H)-yl)-4-methylthiazole-5-carboxylic acid, the title compound was obtained as a colorless solid in 47% yield: mp 170-172° C. (ethyl acetate); $^1$H NMR (300 MHz, CDCl$_3$) δ 8.63 (d, J=8.1 Hz, 2H), 8.55 (s, 1H), 7.77 (d, J=7.8 Hz, 1H), 7.37-7.27 (m, 1H), 6.43 (t, J=5.7 Hz, 1H), 6.16 (dd, J=8.1, 2.6 Hz, 1H), 5.96 (d, J=2.6 Hz, 1H), 4.62 (d, J=5.7 Hz, 2H), 4.03 (t, J=6.6 Hz, 2H), 2.67 (s, 3H), 1.68 (q, J=6.6 Hz, 2H), 0.86-0.74 (m, 1H), 0.52-0.46 (m, 2H), 0.13-0.08 (m, 2H); $^{13}$C NMR (75 MHz, CDCl$_3$) δ 167.9, 162.5, 162.1, 153.7, 152.6, 148.6, 148.3, 136.3, 131.3, 121.7, 104.2, 96.6, 69.1, 41.4, 33.6, 17.3, 7.56, 4.2; MS (ES+) m/z 411.2 (M+1).

Example 1.6

Synthesis of N-(4-Fluorobenzyl)-2-(4-hydroxy-2-oxopyridin-1(2H)-yl)-4-methylthiazole-5-carboxamide

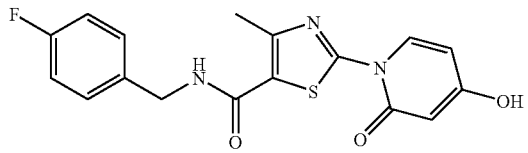 [SMILES: Cc1nc(-n2ccc(O)cc2=O)sc1C(=O)NCc1ccc(F)cc1]

Following the procedure as described in Example 1, making variations only as required to use 4-fluorobenzylamine in place of benzylamine to react with 2-(4-hydroxy-2-oxopyridin-1(2H)-yl)-4-methylthiazole-5-carboxylic acid, the title compound was obtained as a colorless solid in 37% yield: mp 280-282° C. (methanol/ethyl acetate); $^1$H NMR (300 MHz, DMSO-d$_6$) δ 8.74 (t, J=5.9 Hz, 1H), 8.56 (d, J=8.0 Hz, 1H), 7.34-7.29 (m, 2H), 7.12 (t, J=8.9 Hz, 2H), 6.22 (dd, J=8.0, 2.5 Hz, 1H), 5.75 (d, J=2.5 Hz, 1H), 4.35 (d, J=5.8 Hz, 2H), 2.52 (s, 3H); $^{13}$C NMR (75 MHz, DMSO-d$_6$) δ 167.9, 162.0, 161.6, 154.1, 150.2, 139.9, 132.6, 128.7, 127.7, 127.2, 123.6, 104.4, 98.0, 43.1, 17.5; MS (ES+) m/z 360.1 (M+1).

Example 1.7

Synthesis of N-Benzyl-2-(4-(benzyloxy)-2-oxopyridin-1(2H)-yl)-4-methyl-1H-imidazole-5-carboxamide

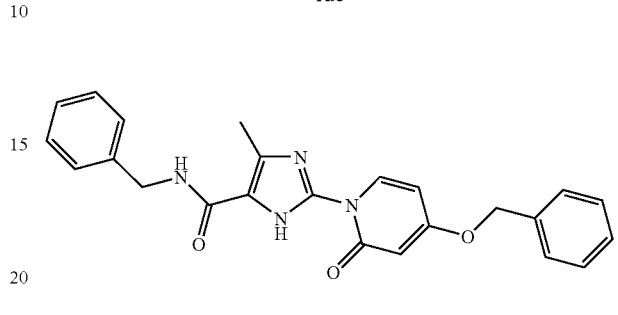

Following the procedure as described in Example 1, making variations only as required to use 2-(4-(benzyloxy)-2-oxopyridin-1(2H)-yl)-4-methyl-1H-imidazole-5-carboxylic acid in place of 4-methyl-2-(2-oxo-4-phenylpyridin-1(2H)-yl)thiazole-5-carboxylic acid to react with benzylamine, the title compound was obtained as a colorless solid in 59% yield: mp 183-184° C.; $^1$H NMR (300 MHz, CDCl$_3$) δ 11.86 (br s, 1H), 8.42 (d, J=8.0 Hz, 1H), 7.43-7.26 (m, 10H), 6.18 (dd, J=8.0, 2.6 Hz, 1H), 6.04 (d, J=2.6 Hz, 1H), 5.05 (s, 2H), 4.61 (d, J=6.0 Hz, 2H), 2.65 (s, 3H); $^{13}$C NMR (75 MHz, CDCl$_3$) δ 167.4, 163.6, 163.4, 138.8, 134.6, 132.2, 129.5, 128.8, 128.7, 128.6, 127.8, 127.8, 127.3, 126.9, 103.5, 98.4, 70.7, 42.7, 11.0; MS (ES+) m/z 415.2 (M+1).

Example 1.8

Synthesis of 2-(4-(Benzyloxy)-2-oxopyridin-1(2H)-yl)-4-methyl-N-(pyridin-3-ylmethyl)-1H-imidazole-5-carboxamide

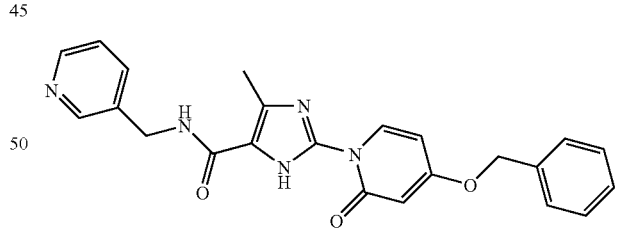

Following the procedure as described in Example 1, making variations only as required to use 2-(4-(benzyloxy)-2-oxopyridin-1(2H)-yl)-4-methyl-1H-imidazole-5-carboxylic acid in place of 4-methyl-2-(2-oxo-4-phenylpyridin-1(2H)-yl)thiazole-5-carboxylic acid to react with 3-(aminomethyl)pyridine, the title compound was obtained as a colorless solid in 63% yield: mp 203-204° C.; $^1$H NMR (300 MHz, DMSO-d$_6$) δ 12.70 (br s, 1H), 8.58-8.51 (m, 2H), 8.43 (d, J=3.9 Hz, 1H), 8.01 (d, J=7.8 Hz, 1H), 7.70 (d, J=7.8 Hz, 1H), 7.50-7.29 (m, 6H), 6.23 (dd, J=7.8, 2.6 Hz, 1H), 6.07 (d, J=2.6 Hz, 1H), 5.16 (s, 2H), 4.40 (d, J=6.3 Hz, 2H), 2.47 (s, 3H); $^{13}$C NMR (75 MHz, DMSO-d$_6$) δ 167.2, 162.9, 162.0, 148.8, 147.8, 137.3, 135.9, 135.6, 135.4, 135.1, 130.8, 128.5, 128.2, 128.0, 127.4, 123.3, 101.6, 97.5, 70.0, 10.5; MS (ES+) m/z 416.3 (M+1).

Example 1.9

Synthesis of N-Benzyl-2-(4-(benzyloxy)-2-oxopyridin-1(2H)-yl)-1,4-dimethyl-1H-imidazole-5-carboxamide

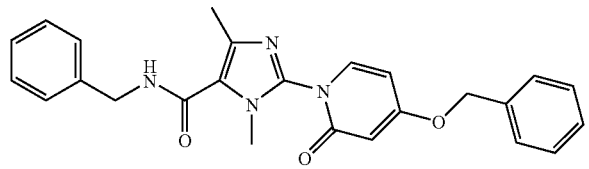 [SMILES: Cc1nc(-n2ccc(OCc3ccccc3)cc2=O)n(C)c1C(=O)NCc1ccccc1]

Following the procedure as described in Example 1, making variations only as required to use 2-(4-(benzyloxy)-2-oxopyridin-1(2H)-yl)-1,4-dimethyl-1H-imidazole-5-carboxylic acid in place of 4-methyl-2-(2-oxo-4-phenylpyridin-1(2H)-yl)thiazole-5-carboxylic acid to react with benzylamine, the title compound was obtained as a colorless solid in 62% yield: mp 232-233° C.; $^1$H NMR (300 MHz, CDCl$_3$) δ 7.43-7.29 (m, 10H), 7.19 (d, J=7.7 Hz, 1H), 6.17 (t, J=5.6 Hz, 1H), 6.09 (dd, J=7.7, 2.5 Hz, 1H), 5.96 (d, J=2.5 Hz, 1H), 5.02 (s, 2H), 4.62 (d, J=5.6 Hz, 2H), 3.67 (s, 3H), 2.39 (s, 3H); $^{13}$C NMR (75 MHz, CDCl$_3$) δ 168.3, 163.3, 160.9, 141.5, 138.0, 137.8, 136.8, 134.7, 128.84, 128.8, 128.6, 127.7, 127.7, 127.6, 123.5, 102.8, 97.8, 70.6, 43.6, 32.7, 15.2; MS (ES+) m/z 429.3 (M+1).

Example 1.10

Synthesis of N-Benzyl-2-(4-(benzyloxy)-2-oxopyridin-1(2H)-yl)-1,5-dimethyl-1H-imidazole-4-carboxamide [Not covered by Formula (I)]

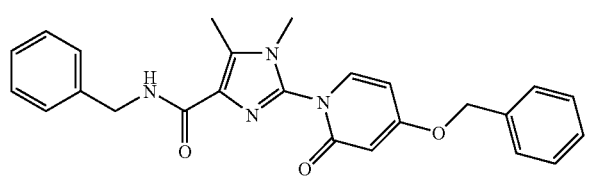 [SMILES: Cc1c(C(=O)NCc2ccccc2)nc(-n2ccc(OCc3ccccc3)cc2=O)n1C]

Following the procedure as described in Example 1, making variations only as required to use 2-(4-(benzyloxy)-2-oxopyridin-1(2H)-yl)-1,5-dimethyl-1H-imidazole-4-carboxylic acid in place of 4-methyl-2-(2-oxo-4-phenylpyridin-1(2H)-yl)thiazole-5-carboxylic acid to react with benzylamine, the title compound was obtained as a colorless solid in 76% yield: mp 190-191° C.; $^1$H NMR (300 MHz, CDCl$_3$) δ 7.43-7.29 (m, 10H), 7.21 (d, J=7.7 Hz, 1H), 6.08 (dd, J=7.7, 2.5 Hz, 1H), 5.98 (d, J=2.5 Hz, 1H), 5.04 (s, 2H), 4.56 (d, J=6.1 Hz, 2H), 3.39 (s, 3H), 2.63 (s, 3H); $^{13}$C NMR (75 MHz, CDCl$_3$) δ 168.3, 163.4, 163.1, 138.6, 138.4, 137.1, 134.7, 133.5, 129.1, 128.8, 128.7, 128.5, 127.8, 127.7, 127.2, 102.7, 97.8, 70.6, 42.7, 30.6, 10.0; MS (ES+) m/z 429.3 (M+1).

Example 1.11

Synthesis of 2-(4-Methoxy-2-oxopyridin-1(2H)-yl)-4-methyl-N-(pyridin-3-ylmethyl)thiazole-5-carboxamide

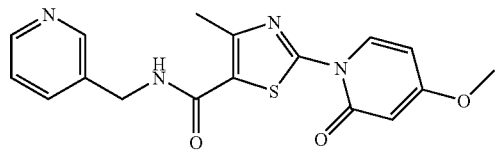 [SMILES: COc1ccn(-c2nc(C)c(C(=O)NCc3cccnc3)s2)c(=O)c1]

Following the procedure as described in Example 1, making variations only as required to use 2-(4-methoxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with pyridin-3-ylmethanamine, the title compound was obtained as a colorless solid in 58% yield: mp 200-202° C. (dichloromethane/methanol); $^1$H NMR (300 MHz, CDCl$_3$) δ 8.64 (d, J=8.1 Hz, 1H), 8.60-8.59 (m, 1H), 8.52-8.51 (m, 1H), 7.51-7.68 (m, 1H), 7.29-7.24 (m, 1H), 6.30 (t, J=5.8 Hz, 1H), 6.17 (dd, J=8.1, 2.6 Hz, 1H), 5.96 (d, J=2.6 Hz, 1H), 4.61 (d, J=5.8 Hz, 2H), 3.82 (s, 3H), 2.67 (s, 3H); $^{13}$C NMR (75 MHz, CDCl$_3$) δ 168.4, 162.4, 162.1, 153.6, 152.6, 149.2, 149.0, 135.7, 133.7, 131.4, 123.6, 121.8, 103.9, 96.2, 56.0, 41.4, 17.3; MS (ES+) m/z 357.2 (M+1).

Example 1.12

Synthesis of 4-Methyl-2-(2-oxo-4-((5-(trifluoromethyl)furan-2-yl)methoxy)pyridin-1(2H)-yl)-N-(pyridin-3-ylmethyl)thiazole-5-carboxamide

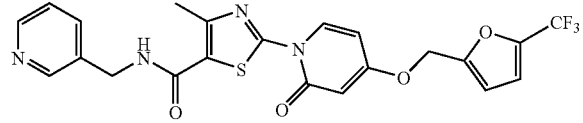 [SMILES: Cc1nc(-n2ccc(OCc3ccc(C(F)(F)F)o3)cc2=O)sc1C(=O)NCc1cccnc1]

Following the procedure as described in Example 1, making variations only as required to use 4-methyl-2-(2-oxo-4-(5-(trifluoromethyl)furan-2-yl)methoxy)pyridin-1(2H)-yl)thiazole-5-carboxylic acid in place of 4-methyl-2-(2-oxo-4-phenylpyridin-1(2H)-yl)thiazole-5-carboxylic acid to react with pyridin-3-ylmethanamine, the title compound was obtained as a colorless solid in 90% yield: mp 240-242° C. (dichloromethane/methanol); $^1$H NMR (300 MHz, CDCl$_3$) δ 8.69 (d, J=8.1 Hz, 1H), 8.60 (s, 1H), 8.52 (d, J=5.8 Hz, 1H), 7.70 (d, J=7.7 Hz, 1H), 7.28-7.26 (m, 1H), 6.81-6.79 (m, 1H), 6.57-6.56 (m, 1H), 6.38 (br s, 1H), 6.25-6.18 (m, 1H), 6.05 (br s, 1H), 5.00 (s, 2H), 4.61 (d, J=5.8 Hz, 2H), 2.67 (s, 3H); $^{13}$C NMR (75 MHz, CDCl$_3$) δ 166.6, 162.3, 161.7, 153.4, 152.5, 150.5, 149.3, 149.1, 135.6, 133.6, 131.8, 123.6, 122.1, 112.4, 111.7, 103.7, 97.1, 62.1, 41.5, 17.3; MS (ES+) m/z 491.3 (M+1).

Example 1.13

Synthesis of 2-(4-(4-Fluorobenzyloxy)-2-oxopyridin-1(2H)-yl)-4-methyl-N-(pyridin-3-ylmethyl)thiazole-5-carboxamide

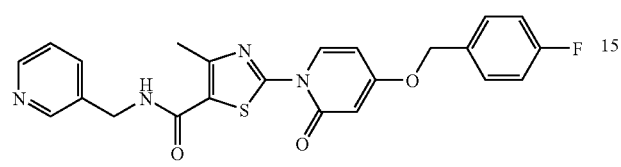

Following the procedure as described in Example 1, making variations only as required to use 2-(4-(4-fluorobenzyloxy)-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with pyridin-3-ylmethanamine, the title compound was obtained as a colorless solid in 52% yield: mp 231-233° C. (dichloromethane/methanol); $^1$H NMR (300 MHz, DMSO-d$_6$) δ 8.83 (t, J=5.6 Hz, 1H), 8.60 (d, J=8.1 Hz, 1H), 8.50 (s, 1H), 8.43 (d, J=4.2 Hz, 1H), 7.69 (d, J=7.9 Hz, 1H), 7.51-7.47 (m, 2H), 7.37-7.29 (m, 1H), 7.22 (t, J=8.8 Hz, 2H), 6.41-6.35 (m, 1H), 6.23 (s, 1H), 5.13 (s, 2H) 4.40 (d, J=4.2 Hz, 2H), 2.53 (s, 3H); $^{13}$C NMR (75 MHz, DMSO-d$_6$) δ 167.4, 164.1, 162.0, 161.6, 160.9, 154.0, 150.6, 149.3, 148.5, 135.6, 132.1, 131.0, 130.9, 123.9, 116.0, 115.7, 104.4, 97.5, 70.1, 42.2, 17.5; MS (ES+) m/z 451.3 (M+1).

Example 1.14

Synthesis of N-(4-Fluorobenzyl)-2-(4-(4-fluorobenzyloxy)-2-oxopyridin-1(2H)-yl)-4-methylthiazole-5-carboxamide

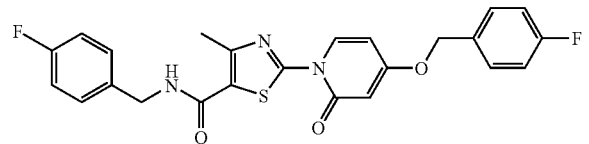 [SMILES: Cc1nc(-n2ccc(OCc3ccc(F)cc3)cc2=O)sc1C(=O)NCc1ccc(F)cc1]

Following the procedure as described in Example 1, making variations only as required to use 2-(4-(4-fluorobenzyloxy)-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with (4-fluorophenyl)methanamine, the title compound was obtained as a colorless solid in 34% yield: mp 249-251° C. (hexanes/ethyl acetate); $^1$H NMR (300 MHz, DMSO-d$_6$) δ 8.78 (t, J=5.9 Hz, 1H), 8.60 (d, J=8.1 Hz, 1H), 7.51-7.47 (m, 2H), 7.34-7.29 (m, 2H), 7.25-7.08 (m, 4H), 6.37 (dd, J=8.1, 2.7 Hz, 1H), 6.23 (d, J=2.7 Hz, 1H), 5.14 (s, 2H), 4.35 (d, J=5.9 Hz, 2H), 2.53 (s, 3H); $^{13}$C NMR (75 MHz, DMSO-d$_6$) δ 167.4, 164.1, 163.2, 161.9, 160.9, 153.9, 150.4, 136.1, 132.1, 131.0, 130.9, 129.8, 123.6, 116.0, 115.7, 104.3, 97.5, 70.1, 42.4, 17.5; MS (ES+) m/z 468.3 (M+1).

Example 1.15

Synthesis of N-(3-Fluorobenzyl)-2-(4-hydroxy-2-oxopyridin-1(2H)-yl)-4-methylthiazole-5-carboxamide

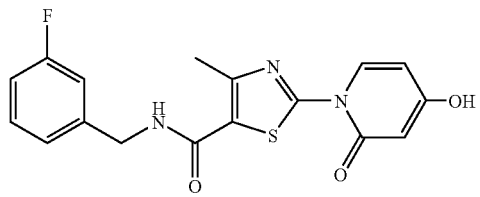 [SMILES: Cc1nc(-n2ccc(O)cc2=O)sc1C(=O)NCc1cccc(F)c1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with (3-fluorophenyl)methanamine, the title compound was obtained as a colorless solid in 44% yield: mp 250-252° C. (ethyl acetate/hexanes); $^1$H NMR (300 MHz, DMSO-d$_6$) δ 11.50 (br s, 1H), 8.78 (t, J=6.0 Hz, 1H), 8.59 (d, J=8.0 Hz, 1H), 7.39-7.30 (m, 1H), 7.13-7.00 (m, 3H), 6.26 (dd, J=8.0, 2.5 Hz, 1H), 5.82 (d, J=2.5 Hz, 1H), 4.39 (d, J=5.9 Hz, 2H), 2.53 (s, 3H); $^{13}$C NMR (75 MHz, DMSO-d$_6$) δ 167.9, 164.2, 162.1, 161.6, 154.2, 142.9, 142.8, 132.6, 130.7, 123.7, 123.4, 114.5, 114.1, 104.4, 98.0, 42.6, 17.5; MS (ES+) m/z: 360.2 (M+1).

Example 1.16

Synthesis of N-(Cyclopropylmethyl)-2-(4-hydroxy-2-oxopyridin-1(2H)-yl)-4-methylthiazole-5-carboxamide

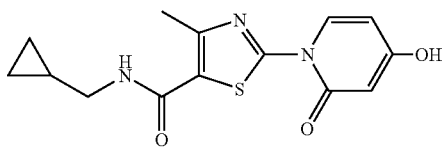 [SMILES: Cc1nc(-n2ccc(O)cc2=O)sc1C(=O)NCC1CC1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with cyclopropylethanamine, the title compound was obtained as a colorless solid in 76% yield: mp 240-242° C. (ethyl acetate/hexanes); $^1$H NMR (300 MHz, DMSO-d$_6$) δ 11.56 (br s, 1H), 8.58 (d, J=8.0 Hz, 1H), 8.26 (t, J=5.6 Hz, 1H), 6.25 (dd, J=8.0, 2.5 Hz, 1H), 5.81 (d, J=2.5 Hz, 1H), 3.05 (m, 2H), 2.51 (s, 3H), 1.05-0.92 (m, 1H), 0.43-0.36 (m, 2H), 0.20-0.15 (m, 2H); $^{13}$C NMR (75 MHz, DMSO-d$_6$) δ 167.9, 161.8, 161.6, 153.9, 149.7, 132.6, 124.0, 104.3, 98.0, 43.9, 17.4, 11.4, 3.7; MS (ES+) m/z: 306.2 (M+1).

Example 1.17

Synthesis of N-(2-Cyclopropylethyl)-2-(4-hydroxy-2-oxopyridin-1(2H)-yl)-4-methylthiazole-5-carboxamide

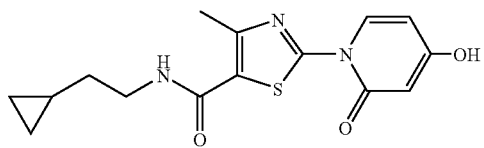 [SMILES: Cc1nc(-n2ccc(O)cc2=O)sc1C(=O)NCCC1CC1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with 2-cyclopropylethanamine, the title compound was obtained as a colorless solid in 64% yield: mp 234-236° C. (ethyl acetate/hexanes); $^1$H NMR (300 MHz, DMSO-$d_6$) δ 11.47 (s, 1H), 8.58 (d, J=8.0 Hz, 1H), 8.16 (t, J=5.6 Hz, 1H), 6.25 (dd, J=8.0, 2.6 Hz, 1H), 5.81 (d, J=2.5 Hz, 1H), 3.26-3.20 (m, 2H), 2.50 (s, 3H), 1.40-1.34 (m, 2H), 0.76-0.59 (m, 1H), 0.39-0.33 (m, 2H), 0.03-0.01 (m, 2H); $^{13}$C NMR (75 MHz, DMSO-$d_6$) δ 167.8, 161.8, 161.6, 153.9, 149.4, 132.6, 124.2, 104.3, 98.0, 39.9, 34.4, 17.4, 9.0, 4.6; MS (ES+) m/z 320.2 (M+1).

Example 1.18

Synthesis of N-(4-Fluorophenethyl)-2-(4-hydroxy-2-oxopyridin-1(2H)-yl)-4-methylthiazole-5-carboxamide

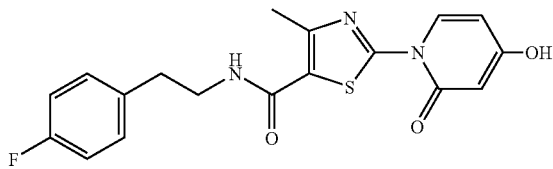 [SMILES: Cc1nc(-n2ccc(O)cc2=O)sc1C(=O)NCCc1ccc(F)cc1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with 2-(4-fluorophenyl)ethanamine, the title compound was obtained as a colorless solid in 69% yield: mp 225-227° C. (ethyl acetate/hexanes); $^1$H NMR (300 MHz, DMSO-$d_6$) δ 11.47 (s, 1H), 8.57 (d, J=8.0 Hz, 1H), 8.23 (t, J=5.5 Hz, 1H), 7.25-7.18 (m, 2H), 7.12-7.04 (m, 2H), 6.25 (dd, J=8.0, 2.6 Hz, 1H), 5.81 (d, J=2.5 Hz, 1H), 3.42-3.35 (m, 2H), 2.78 (t, J=7.2 Hz, 2H), 2.50 (s, 3H); $^{13}$C NMR (75 MHz, DMSO-$d_6$) δ 167.8, 161.9, 161.6, 159.6, 154.1, 149.6, 136.0, 132.6, 130.9, 124.0, 115.5, 104.3, 98.0, 41.2, 34.5, 17.3; MS (ES+) m/z 374.2 (M+1).

Example 1.19

Synthesis of N-(3,4-Difluorobenzyl)-2-(4-hydroxy-2-oxopyridin-1(2H)-yl)-4-methylthiazole-5-carboxamide

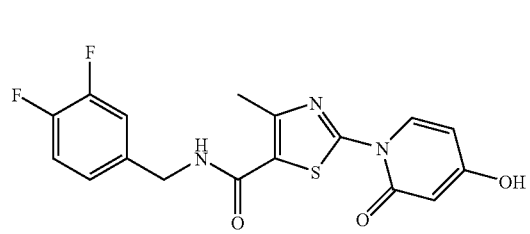 [SMILES: Cc1nc(-n2ccc(O)cc2=O)sc1C(=O)NCc1ccc(F)c(F)c1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with (3,4-difluorophenyl)methanamine, the title compound was obtained as a colorless solid in 88% yield: mp 294-296° C. (ethyl acetate/hexanes); $^1$H NMR (300 MHz, DMSO-$d_6$) δ 11.50 (br s, 1H), 8.77 (t, J=5.8 Hz, 1H), 8.59 (d, J=8.0 Hz, 1H), 7.40-7.28 (m, 2H), 7.15-7.10 (m, 1H), 6.26 (dd, J=8.0, 2.6 Hz, 1H), 5.82 (d, J=2.6 Hz, 1H), 4.35 (d, J=5.8 Hz, 2H), 2.53 (s, 3H); $^{13}$C NMR (75 MHz, DMSO-$d_6$) δ 167.9, 162.1, 161.6, 154.2, 150.5, 137.7, 132.6, 124.5, 123.3, 117.8, 117.6, 116.8, 116.6, 104.4, 98.0, 42.2, 17.5; MS (ES+) m/z 378.2 (M+1).

Example 1.20

Synthesis of 2-(4-Hydroxy-2-oxopyridin-1(2H)-yl)-4-methyl-N-(pyridin-4-ylmethyl)thiazole-5-carboxamide

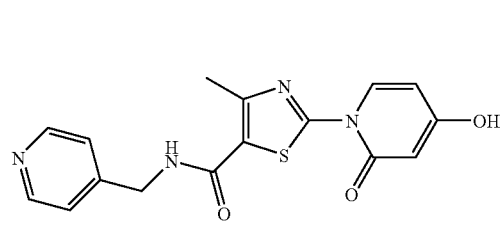 [SMILES: Cc1nc(-n2ccc(O)cc2=O)sc1C(=O)NCc1ccncc1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with pyridin-4-ylmethanamine, the title compound was obtained as a colorless solid in 46% yield: mp 275-278° C. (dichloromethane/methanol); $^1$H NMR (300 MHz, DMSO-$d_6$) δ 11.59 (br s, 1H), 8.88-8.78 (m, 1H), 8.58 (t, J=8.9 Hz, 1H), 8.47-8.44 (m, 2H), 7.26-7.23 (m, 2H), 6.27-6.22 (m, 1H), 5.85-5.80 (m, 1H), 4.44-4.30 (m, 2H), 2.56 (s, 3H); $^{13}$C NMR (75 MHz, DMSO-$d_6$) δ 167.9, 162.2, 161.6, 154.2, 150.6, 149.9, 148.8, 132.6, 123.2, 122.6, 104.4, 98.0, 42.2, 17.5; MS (ES+) m/z 343.2 (M+1).

Example 1.21

Synthesis of 2-(4-Hydroxy-2-oxopyridin-1(2H)-yl)-4-methyl-N-((5-methylpyrazin-2-yl)methyl)thiazole-5-carboxamide

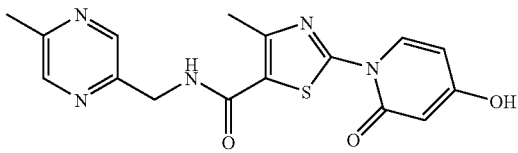 [SMILES: Cc1cnc(CNC(=O)c2sc(-n3ccc(O)cc3=O)nc2C)cn1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with (5-methylpyrazin-2-yl)methanamine, the title compound was obtained as a colorless solid in 14% yield: $^1$H NMR (300 MHz, DMSO-$d_6$) δ 11.49 (s, 1H), 8.80 (t, J=5.2 Hz, 1H), 8.59 (d, J=7.8 Hz 1H), 8.44 (s, 2H), 6.26 (d, J=7.8 Hz, 1H), 5.81 (s, 1H), 4.47 (d, J=5.2 Hz, 2H), 2.52 (s, 3H), 2.43 (s, 3H); MS (ES+) m/z 358.1 (M+1).

Example 1.22

Synthesis of 2-(4-Hydroxy-2-oxopyridin-1(2H)-yl)-4-methyl-N-(oxazol-2-ylmethyl)thiazole-5-carboxamide

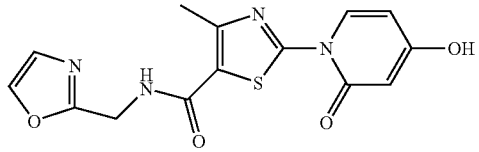 [SMILES: Cc1nc(-n2ccc(O)cc2=O)sc1C(=O)NCc1ncco1]

Following the procedure as described in Example 1, making variations only as required to use 2-(4-hydroxy-2-oxopyridin-1(2H)-yl)-4-methylthiazole-5-carboxylic acid in place of 4-methyl-2-(2-oxo-4-phenylpyridin-1(2H)-yl)thiazole-5-carboxylic acid to react with oxazol-2-ylmethanamine, the title compound was obtained as a colorless solid in 25% yield: $^1$H NMR (300 MHz, DMSO-$d_6$) δ 11.51 (s, 1H), 8.84 (t, J=5.7 Hz, 1H), 8.59 (d, J=8.0 Hz, 1H), 8.02 (s, 1H), 7.12 (s, 1H), 6.26 (dd, J=8.0, 2.5 Hz, 1H), 5.82 (d, J=2.5 Hz, 1H), 4.48 (d, J=5.7 Hz, 2H), 2.53 (s, 3H); MS (ES+) m/z 333.2 (M+1).

Example 1.23

Synthesis of 5-(4-(Benzyloxy)-2-oxopyridin-1(2H)-yl)-3-methyl-N-(pyridin-3-ylmethyl)thiophene-2-carboxamide

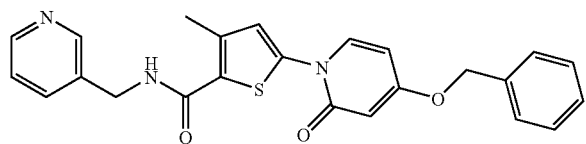 [SMILES: Cc1cc(-n2ccc(OCc3ccccc3)cc2=O)sc1C(=O)NCc1cccnc1]

Following the procedure as described in Example 1, making variations only as required to use 5-(4-(benzyloxy)-2-oxopyridin-1(2H)-yl)-3-methylthiophene-2-carboxylic acid in place of 4-methyl-2-(2-oxo-4-phenylpyridin-1(2H)-yl) thiazole-5-carboxylic acid to react with 3-(aminomethyl)pyridine, the title compound was obtained as a colorless solid in 39% yield: mp 165-167° C.; $^1$H NMR (300 MHz, CDCl$_3$) δ 8.61 (d, J=1.5 Hz, 1H), 8.54 (dd, J=4.7, 1.5 Hz, 1H), 7.71 (dt, J=7.8, 1.5 Hz, 1H), 7.57 (d, J=7.8 Hz, 1H), 7.43-7.27 (m, 6H), 6.85 (s, 1H), 6.30 (t, J=5.8 Hz, 1H), 6.15 (dd, J=7.8, 2.7 Hz, 1H), 6.06 (d, J=2.7 Hz, 1H), 5.04 (s, 2H), 4.61 (d, J=5.8 Hz, 2H), 2.54 (s, 3H); $^{13}$C NMR (75 MHz, DMSO-$d_6$) δ 166.2, 162.6, 160.9, 138.8, 137.5, 135.4, 135.0, 128.5, 128.2, 128.0, 126.9, 120.5, 102.6, 97.3, 70.0, 15.5; MS (ES+) m/z 432.2 (M+1).

Example 1.24

Synthesis of N-Benzyl-2-(4-(4-fluorobenzyloxy)-2-oxopyridin-1(2H)-yl)-4-methylthiazole-5-carboxamide

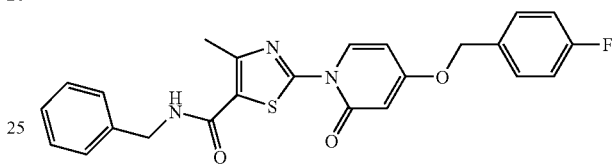

Following the procedure as described in Example 1, making variations only as required to use 4-methyl-2-(2-oxo-4-(4-(trifluoromethyl)benzyloxy)pyridin-1(2H)-yl)thiazole-5-carboxylic acid in place of 4-methyl-2-(2-oxo-4-phenylpyridin-1(2H)-yl)thiazole-5-carboxylic acid to react with benzylamine, the title compound was obtained as a colorless solid in 8% yield: mp 243-245° C.; $^1$H NMR (300 MHz, CDCl$_3$) δ 8.7 (d, J=8.1 Hz, 1H), 7.59-7.06 (m, 9H), 6.23-6.05 (m, 3H), 5.28 (s, 2H), 4.60 (d, J=5.4 Hz, 2H), 2.68 (s, 3H); $^{13}$C NMR (75 MHz, CDCl$_3$) δ 192.8, 167.2, 162.3, 162.2, 153.5, 152.1, 137.7, 131.7, 130.4, 129.9, 129.7, 128.9, 127.9, 127.7, 122.4, 116.0, 115.7, 104.0, 97.4, 70.1, 44.1, 17.3; MS (ES+) m/z 450.3 (M+1).

Example 2

Synthesis of N-Benzyl-2-(4-(benzyloxy)-2-oxopyridin-1(2H)-yl)-4-methylthiazole-5-carboxamide

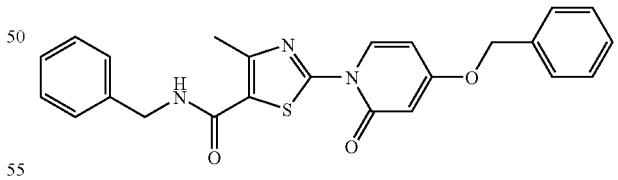

To a solution of 4-methyl-2-(4-(benzyloxy)-2-oxopyridin-1(2H)-yl)thiazole-5-carboxylic acid (0.10 g, 0.29 mmol) and 4-methylmorpholine (0.032 mL, 0.29 mmol) in anhydrous dichloromethane (6 mL) was added isobutylchloroformate (0.044 mL, 0.34 mmol) dropwise at 0° C. After stirring at ambient temperature for 2 hours, the reaction mixture was cooled to 0° C. and benzylamine (0.032 mL, 0.29 mmol) was added dropwise. Stirring at ambient temperature was continued for 18 hours, then the reaction mixture was diluted with ethyl acetate (30 mL) and washed with saturated aqueous sodium bicarbonate (10 mL) and brine (10 mL). The organic layer was dried over anhydrous sodium sulfate, filtered and concentrated in vacuo. The residue was triturated with a mixture of ethyl acetate/dichloromethane 1/1 (10 mL) to afford the title compound as a white solid (0.055 g, 44%): mp 219-220° C. (ethyl acetate/dichloromethane); $^1$H NMR (300 MHz, CDCl$_3$) δ 8.67 (d, J=8.1 Hz, 1H), 7.47-7.15 (m, 10H), 6.22 (dd, J=8.1, 2.6 Hz, 1H), 6.14 (t, J=5.6 Hz, 1H), 6.05 (d, J=2.6 Hz, 1H), 5.03 (s, 2H), 4.58 (d, J=5.6 Hz, 2H), 2.68 (s, 3H); $^{13}$C NMR (75 MHz, CDCl$_3$) δ 167.4, 162.3, 162.0, 153.5, 152.2, 137.8, 134.6, 131.6, 128.9, 128.8, 127.9, 127.8, 127.7, 122.4, 104.1, 97.4, 70.8, 44.1, 17.3; (ES+) m/z 432.2 (M+1).

Example 3

Synthesis of 2-(4-Amino-2-oxopyridin-1(2H)-yl)-N-benzyl-4-methylthiazole-5-carboxamide

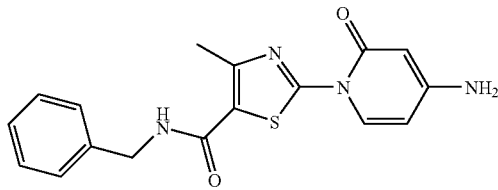 [SMILES: Cc1nc(-n2ccc(N)cc2=O)sc1C(=O)NCc1ccccc1]

To a degassed solution of N-benzyl-2-bromo-4-methylthiazole-5-carboxamide (1.58 g, 5.00 mmol), 4-aminopyridin-2(1H)-one (0.72 g, 6.50 mmol), potassium carbonate (2.00 g, 14.40 mmol) and 8-hydroxyquinoline (0.08 g, 0.50 mmol) in dimethyl sulfoxide (30 mL) was added copper(I) iodide (0.10 g, 0.50 mmol). The reaction mixture was heated at 75-80 C. for 16 hours, then cooled to ambient temperature. Water (300 mL) was added to the mixture and the crude product was precipitated and collected by filtration. The crude product was subjected to column chromatography to afford the title compound as a white solid (0.84 g, 49%): mp 171-172° C.; $^1$H NMR (300 MHz, DMSO-d$_6$) δ 8.68 (t, J=5.7 Hz, 1H), 8.40 (d, J=7.8 Hz, 1H), 7.32-7.19 (m, 5H), 6.80 (s, 2H), 6.07 (dd, J=7.8, 1.8, Hz, 1H), 5.38 (d, J=1.8 Hz, 1H), 4.37 (d, J=5.7 Hz, 2H), 2.50 (s, 3H); $^{13}$C NMR (75 MHz, DMSO-d$_6$) δ 162.2, 160.8, 157.7, 154.6, 150.0, 140.0, 131.5, 128.7, 127.7, 127.1, 122.9, 103.4, 90.5, 43.0, 17.5; MS (ES+) m/z 341.2 (M+1).

Example 3.1

Synthesis of N-Benzyl-4-methyl-2-(3-methyl-2-oxopyrazin-1(2H)-yl)thiazole-5-carboxamide [Not covered by Formula (I)]

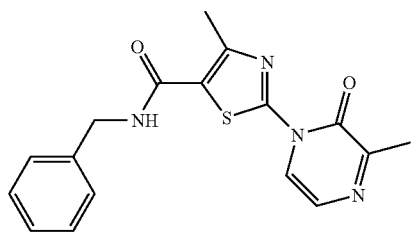 [SMILES: Cc1nc(-n2ccnc(C)c2=O)sc1C(=O)NCc1ccccc1]

Following the procedure as described in Example 3, making variations only as required to use 3-methylpyrazin-2(1H)-one in place of 4-aminopyridin-2(1H)-one to react with N-benzyl-2-bromo-4-methylthiazole-5-carboxamide, the title compound was obtained as a white solid in 5% yield: mp 186-187° C.; $^1$H NMR (300 MHz, CDCl$_3$) δ 8.44 (s, 1H), 7.45-7.25 (m, 6H), 6.12 (s, 1H), 4.59 (d, J=5.7 Hz, 2H), 2.69 (s, 3H), 2.55 (s, 3H); $^{13}$C NMR (75 MHz, CDCl$_3$) δ 161.6, 159.2, 153.4, 152.4, 152.0, 137.5, 128.8, 127.9, 127.8, 124.5, 123.5, 119.3, 44.2, 20.8, 17.3; MS (ES+) m/z 341.2 (M+1).

Example 3.2

Synthesis of N-Benzyl-2-(5-(benzyloxy)-2-oxopyridin-1(2H)-yl)-4-methylthiazole-5-carboxamide

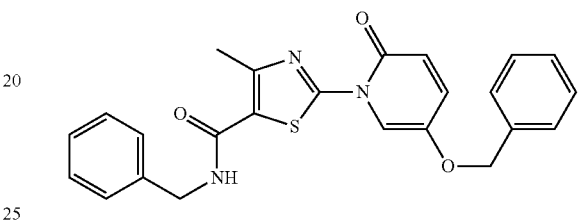

Following the procedure as described in Example 3, making variations only as required to use 5-(benzyloxy)pyridin-2(1H)-one in place of 4-aminopyridin-2(1H)-one to react with N-benzyl-2-bromo-4-methylthiazole-5-carboxamide, the title compound was obtained as a white solid in 32% yield: mp 166-167° C.; $^1$H NMR (300 MHz, CDCl$_3$) δ 8.36 (d, J=2.7 Hz, 1H), 7.48-7.22 (m, 11H), 6.61 (d, J=9.9 Hz, 1H), 6.45 (t, J=5.4 Hz, 1H), 4.98 (s, 2H), 4.56 (d, J=5.4 Hz, 2H), 2.70 (s, 3H); $^{13}$C NMR (75 MHz, CDCl$_3$) δ 162.2, 158.7, 153.3, 152.1, 143.3, 137.8, 136.1, 135.5, 128.7, 128.6, 127.9, 127.8, 127.6, 121.7, 112.0, 71.3, 44.0, 17.3; MS (ES+) m/z 432.2 (M+1).

Example 3.3

Synthesis of N-Benzyl-2-(5-chloro-2-oxopyridin-1(2H)-yl)-4-methylthiazole-5-carboxamide

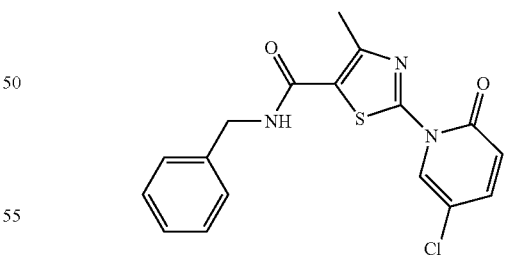

Following the procedure as described in Example 3, making variations only as required to use 5-chloro-2-hydroxypyridine in place of 4-aminopyridin-2(1H)-one to react with N-benzyl-2-bromo-4-methylthiazole-5-carboxamide, the title compound was obtained as a white solid in 39% yield: mp 173-174° C.; $^1$H NMR (300 MHz, CDCl$_3$) δ 8.79 (d, J=2.4 Hz, 1H), 7.36-7.23 (m, 6H), 6.61 (d, J=9.9 Hz, 1H), 6.43 (s, 1H), 4.55 (d, J=5.4 Hz, 2H), 2.66 (s, 3H); $^{13}$C NMR (75 MHz, CDCl$_3$) δ 161.9, 158.8, 152.4, 152.0, 141.0, 131.7, 128.7, 128.5, 127.8, 127.6, 123.8, 121.9, 115.5, 44.1, 17.2; MS (ES+) m/z 360.1 (M+1), 362.1 (M+1).

Example 3.4

Synthesis of N-Benzyl-4-methyl-2-(2-oxo-5-(trifluoromethyl)pyridin-1(2H)-yl)thiazole-5-carboxamide

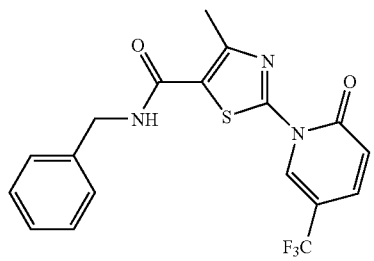 [SMILES: Cc1nc(-n2cc(C(F)(F)F)ccc2=O)sc1C(=O)NCc1ccccc1]

Following the procedure as described in Example 3, making variations only as required to use 2-hydroxy-5-(trifluoromethyl)pyridine in place of 4-aminopyridin-2(1H)-one to react with N-benzyl-2-bromo-4-methylthiazole-5-carboxamide, the title compound was obtained as a white solid in 60% yield: mp 148-149° C.; $^1$H NMR (300 MHz, CDCl$_3$) δ 9.19 (br s, 1H), 7.53 (dd, J=9.6, 2.7 Hz, 1H), 7.37-7.25 (m, 5H), 6.78 (d, J=9.6 Hz, 1H), 6.27 (t, J=5.7 Hz, 1H), 4.58 (d, J=5.7 Hz, 2H), 2.69 (s, 3H); $^{13}$C NMR (75 MHz, CDCl$_3$) δ 161.7, 159.6, 152.4, 151.9, 137.6, 135.2, 131.1, 128.8, 127.9, 124.6, 124.5, 122.1, 121.1, 111.8, 44.2, 17.2; MS (ES+) m/z 394.2 (M+1).

Example 3.5

Synthesis of N-Benzyl-4-methyl-2-(2-oxo-3-(trifluoromethyl)pyridin-1(2H)-yl)thiazole-5-carboxamide

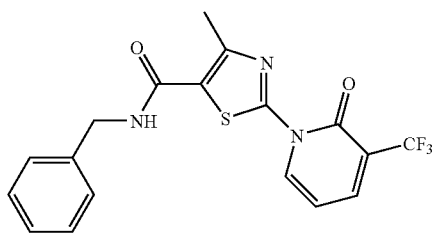 [SMILES: Cc1nc(-n2cccc(C(F)(F)F)c2=O)sc1C(=O)NCc1ccccc1]

Following the procedure as described in Example 3, making variations only as required to use 2-hydroxy-3-(trifluoromethyl)pyridine in place of 4-aminopyridin-2(1H)-one to react with N-benzyl-2-bromo-4-methylthiazole-5-carboxamide, the title compound was obtained as a white solid in 37% yield: mp 203-204° C.; $^1$H NMR (300 MHz, CDCl$_3$) δ 9.01 (d, J=7.2 Hz, 1H), 7.87 (d, J=7.2 Hz, 1H), 7.36-7.23 (m, 5H), 6.53 (t, J=7.2 Hz, 1H), 6.10 (s, 1H), 4.57 (d, J=5.4 Hz, 2H), 2.69 (s, 3H); $^{13}$C NMR (75 MHz, CDCl$_3$) δ 161.7, 156.6, 152.2, 152.1, 139.3, 139.2, 137.4, 135.1, 128.9, 128.8, 127.8, 123.8, 121.9, 106.0, 44.2, 17.2; MS (ES+) m/z 394.2 (M+1).

Example 3.6

Synthesis of N-Benzyl-4-methyl-2-(2-oxo-4-(trifluoromethyl)pyridin-1(2H)-yl)thiazole-5-carboxamide

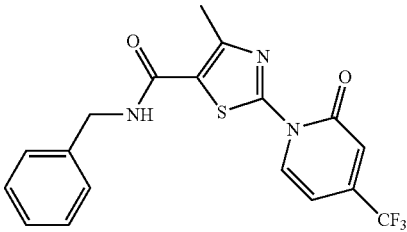 [SMILES: Cc1nc(-n2ccc(C(F)(F)F)cc2=O)sc1C(=O)NCc1ccccc1]

Following the procedure as described in Example 3, making variations only as required to use 2-hydroxy-4-(trifluoromethyl)pyridine in place of 4-aminopyridin-2(1H)-one to react with N-benzyl-2-bromo-4-methylthiazole-5-carboxamide, the title compound was obtained as a white solid in 9% yield: mp 197-198° C.; $^1$H NMR (300 MHz, CDCl$_3$) δ 8.93 (d, J=7.8 Hz, 1H), 7.39-7.25 (m, 5H), 7.00 (d, J=0.6 Hz, 1H), 6.57-6.54 (m, 1H), 6.17 (s, 1H), 4.59 (d, J=5.7 Hz, 2H), 2.70 (s, 3H); $^{13}$C NMR (75 MHz, CDCl$_3$) δ 161.7, 159.3, 152.4, 141.0, 137.5, 133.1, 128.8, 127.9, 127.8, 124.1, 119.1, 103.0, 44.2, 17.3; MS (ES+) m/z 394.2 (M+1).

Example 3.7

Synthesis of N-Benzyl-2-(3-(benzyloxy)-2-oxopyridin-1(2H)-yl)-4-methylthiazole-5-carboxamide

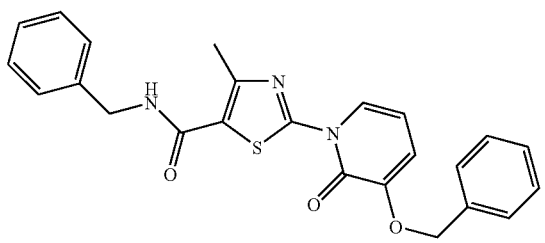 [SMILES: Cc1nc(-n2cccc(OCc3ccccc3)c2=O)sc1C(=O)NCc1ccccc1]

Following the procedure as described in Example 3, making variations only as required to use 3-(benzyloxy)pyridin-2-ol in place of 4-aminopyridin-2(1H)-one to react with N-benzyl-2-bromo-4-methylthiazole-5-carboxamide, the title compound was obtained as a white solid in 7% yield: mp 198-201° C.; $^1$H NMR (300 MHz, CDCl$_3$) δ 8.45 (dd, J=6.0, 3.0 Hz, 1H), 7.46-7.29 (m, 10H), 6.73 (d, J=6.0 Hz, 1H), 6.32 (t, J=6.0 Hz, 1H), 6.13 (br, 1H), 5.15 (s, 2H), 4.61 (d, J=6.0 Hz, 2H), 2.71 (s, 3H); $^{13}$C NMR (75 MHz, CDCl$_3$) δ 187.9, 162.1, 152.1, 148.9, 137.7, 135.5, 128.8, 128.7, 128.3, 127.8, 127.7, 127.3, 122.9, 114.8, 106.7, 106.7, 96.8, 71.1, 44.1, 17.3; MS (ES+) m/z 432.2 (M+1).

Example 3.8

Synthesis of N-Benzyl-2-(5-(benzyloxy)-1-oxoisoquinolin-2(1H)-yl)-4-methylthiazole-5-carboxamide

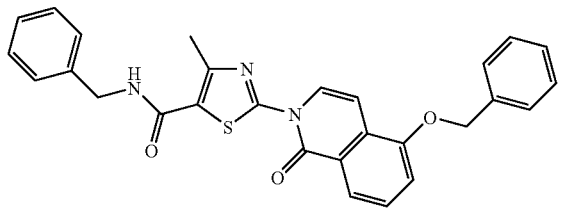 [SMILES: Cc1nc(-n2ccc3c(OCc4ccccc4)cccc3c2=O)sc1C(=O)NCc1ccccc1]

Following the procedure as described in Example 3, making variations only as required to use 5-(benzyloxy)isoquinolin-1(2H)-one in place of 4-aminopyridin-2(1H)-one to react with N-benzyl-2-bromo-4-methylthiazole-5-carboxamide, the title compound was obtained as a white solid in 2% yield: mp 225-226° C.; $^1$H NMR (300 MHz, CD$_3$OD) δ 7.77 (d, J=6.0 Hz, 1H), 7.41-7.25 (m, 11H), 7.10-7.08 (m, 2H), 6.99 (d, J=9.0 Hz, 1H), 4.55 (s, 2H), 4.50 (s, 2H), 2.57 (s, 3H); $^{13}$C NMR (75 MHz, DMSO-d$_6$) δ 162.0, 159.6, 153.5, 151.3, 136.7, 135.0, 128.3, 127.2, 126.8, 126.7, 126.6, 126.4, 125.6, 125.4, 125.3, 125.2, 124.2, 115.5, 114.3, 99.9, 41.7, 31.1, 14.1; MS (ES+) m/z 482.3 (M+1).

Example 3.9

Synthesis of N-Benzyl-2-(6-(benzyloxy)-2-oxoquinolin-1(2H)-yl)-4-methylthiazole-5-carboxamide

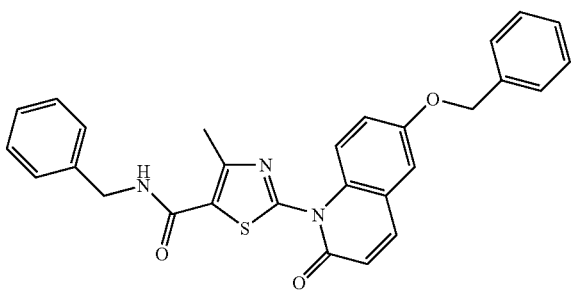 [SMILES: Cc1nc(-n2c(=O)ccc3cc(OCc4ccccc4)ccc32)sc1C(=O)NCc1ccccc1]

Following the procedure as described in Example 3, making variations only as required to use 6-(benzyloxy)quinolin-1(2H)-one in place of 4-aminopyridin-2(1H)-one to react with N-benzyl-2-bromo-4-methylthiazole-5-carboxamide, the title compound was obtained as a white solid in 3% yield: mp 213-216° C.; $^1$H NMR (300 MHz, CD$_3$OD) δ 7.85 (d, J=12.0 Hz, 1H), 7.41-7.23 (m, 11H), 7.11 (d, J=3.0 Hz, 1H), 7.08 (d, J=3.0 Hz, 1H), 7.02 (d, J=3.0 Hz, 1H), 6.58 (d. J=9.0 Hz, 1H), 4.55 (s, 2H), 4.51 (s, 2H), 2.57 (s, 3H); $^{13}$C NMR (75 MHz, DMSO-d$_6$) δ 161.4, 159.7, 154.4, 151.9, 139.6, 138.8, 137.9, 135.8, 132.1, 129.9, 129.2, 128.3, 128.2, 127.2, 126.8, 121.9, 119.9, 119.7, 116.1, 111.4, 42.8, 34.5, 16.8; MS (ES+) m/z 482.3 (M+1).

Example 3.10

Synthesis of N-Benzyl-4-methyl-2-(2-oxopyridin-1(2H)-yl)thiazole-5-carboxamide

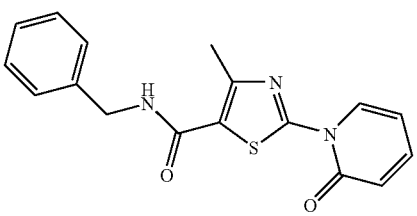 [SMILES: Cc1nc(-n2ccccc2=O)sc1C(=O)NCc1ccccc1]

Following the procedure as described in Example 3, making variations only as required to use pyridin-2(1H)-one in place of 4-aminopyridin-2(1H)-one to react with N-benzyl-2-bromo-4-methylthiazole-5-carboxamide, the title compound was obtained as a colorless solid in 48% yield: mp 180-182° C. (hexane/ethyl acetate); $^1$H NMR (300 MHz, CDCl$_3$) δ 8.83 (t, J=5.9 Hz, 1H), 8.71 (dd, J=7.3, 1.7 Hz, 1H), 7.65-7.59 (m, 1H), 7.37-7.18 (m, 5H), 6.74 (d, J=9.3 Hz, 1H), 6.60-6.55 (m, 1H), 4.39 (d, J=5.9 Hz, 2H), 2.56 (s, 3H); $^{13}$C NMR (75 MHz, CDCl$_3$) δ 167.9, 162.0, 161.6, 154.1, 150.2, 139.9, 132.6, 128.7, 127.7, 127.2, 123.6, 104.4, 98.0, 43.1, 17.5; (ES+) m/z 326.1 (M+1).

Example 3.11

Synthesis of N-(4-Fluorobenzyl)-4-methyl-2-(2-oxopyridin-1(2H)-yl)thiazole-5-carboxamide

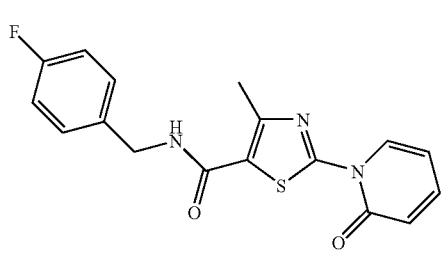 [SMILES: Cc1nc(-n2ccccc2=O)sc1C(=O)NCc1ccc(F)cc1]

Following the procedure as described in Example 3, making variations only as required to use pyridin-2(1H)-one in place of 4-aminopyridin-2(1H)-one to react with 2-bromo-N-(4-fluorobenzyl)-4-methylthiazole-5-carboxamide in place of N-benzyl-2-bromo-4-methylthiazole-5-carboxamide, the title compound was obtained as a colorless solid in 45% yield: mp 170-172° C. (hexane/ethyl acetate); $^1$H NMR (300 MHz, CDCl$_3$) δ 8.80-8.77 (m, 1H), 7.47-7.42 (m, 1H), 7.34-7.28 (m, 2H), 7.03 (t, J=8.6 Hz, 2H), 6.75 (d, J=9.4 Hz, 1H), 6.44 (d, J=6.9 Hz, 1H), 6.06 (t, J=5.6 Hz, 1H), 4.56 (d, J=5.6 Hz, 2H), 2.70 (s, 3H); $^{13}$C NMR (75 MHz, CDCl$_3$) δ 163.9, 162.1, 160.6, 153.2, 152.5, 139.9, 133.5, 131.2, 129.6, 129.5, 122.9, 121.3, 115.8, 115.5, 107.8, 43.4, 17.3; (ES+) m/z 344.2 (M+1).

Example 3.12

Synthesis of 2-(4-(Benzyloxy)-2-oxopyridin-1(2H)-yl)-N-(4-fluorobenzyl)-4-methylthiazole-5-carboxamide

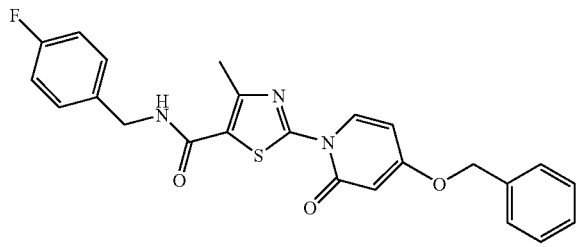 [SMILES: Cc1nc(-n2ccc(OCc3ccccc3)cc2=O)sc1C(=O)NCc1ccc(F)cc1]

Following the procedure as described in Example 3, making variations only as required to use 4-(benzyloxy)pyridin-2(1H)-one in place of 4-aminopyridin-2(1H)-one to react with 2-bromo-N-(4-fluorobenzyl)-4-methylthiazole-5-carboxamide in place of N-benzyl-2-bromo-4-methylthiazole-5-carboxamide, the title compound was obtained as a colorless solid in 92% yield: mp 223-225° C. (hexane/ethyl acetate); $^1$H NMR (300 MHz, CDCl$_3$) δ 8.67 (t, J=8.1 Hz, 1H), 7.38-7.35 (m, 5H), 7.32-7.27 (m, 2H), 7.01 (t, J=8.6 Hz, 2H), 6.23 (dd, J=8.1, 2.3 Hz, 1H), 6.11 (t, J=5.5 Hz, 1H), 6.06 (d, J=2.3 Hz, 1H), 5.03 (s, 2H), 4.54 (d, J=5.5 Hz, 2H), 2.67 (s, 3H); $^{13}$C NMR (75 MHz, CDCl$_3$) δ 167.4, 163.9, 162.2, 160.6, 153.5, 152.3, 134.5, 133.6, 131.5, 129.6, 128.8, 128.7, 127.7, 122.1, 115.8, 104.1, 97.3, 70.8, 43.3, 17.3; (ES+) m/z 450.2 (M+1).

Example 3.13

Synthesis of N-Benzyl-4-methyl-2-(2-oxo-4-(phenylcarbamoyl)pyridin-1(2H)-yl)thiazole-5-carboxamide

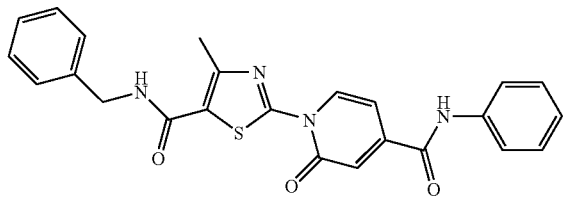 [SMILES: Cc1nc(-n2ccc(C(=O)Nc3ccccc3)cc2=O)sc1C(=O)NCc1ccccc1]

Following the procedure as described in Example 3, making variations only as required to use 2-hydroxy-N-phenyl-isonicotinamide in place of 4-aminopyridin-2(1H)-one to react with N-benzyl-2-bromo-4-methylthiazole-5-carboxamide, the title compound was obtained as a colorless solid in 20% yield: mp 243-245° C. (hexane/ethyl acetate); $^1$H NMR (300 MHz, DMSO-d$_6$) δ 10.53 (s, 1H), 8.88 (t, J=5.8 Hz, 1H), 8.83 (d, J=7.6 Hz, 1H), 7.72 (d, J=7.6 Hz, 2H), 7.36-7.19 (m, 8H), 7.10 (t, J=7.3 Hz, 1H), 6.98 (dd, J=7.6, 1.8 Hz, 1H), 4.40 (d, J=5.8 Hz, 2H), 2.59 (s, 3H); $^{13}$C NMR (75 MHz, DMSO-d$_6$) δ 163.0, 161.7, 160.2, 153.5, 150.7, 139.8, 132.0, 129.1, 128.7, 127.7, 127.2, 124.7, 124.6, 123.6, 121.0, 119.5, 107.0, 106.1, 43.2, 17.5; (ES+) m/z 445.1 (M+1).

Example 3.14

Synthesis of N-Benzyl-4-methyl-2-(2-oxo-3-(phenylcarbamoyl)pyridin-1(2H)-yl)thiazole-5-carboxamide

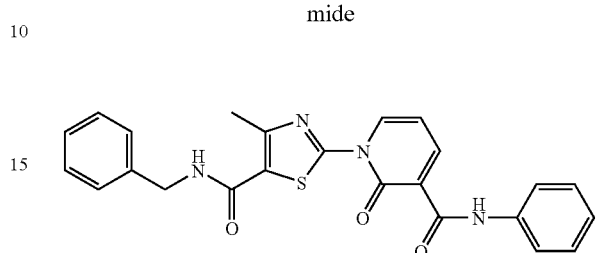

Following the procedure as described in Example 3, making variations only as required to use 2-oxo-N-phenyl-1,2-dihydropyridine-3-carboxamide in place of 4-aminopyridin-2(1H)-one to react with N-benzyl-2-bromo-4-methylthiazole-5-carboxamide, the title compound was obtained as a colorless solid in 15% yield: mp 225-227° C. (hexane/ethyl acetate); $^1$H NMR (300 MHz, DMSO-d$_6$) δ 13.14 (s, 1H), 8.64-8.55 (m, 2H), 8.18 (dd, J=6.6, 2.1 Hz, 1H), 7.58-7.47 (m, 5H), 7.32-7.26 (m, 4H), 7.24-7.17 (m, 1H), 6.75-6.70 (m, 1H), 4.37 (d, J=5.9 Hz, 2H), 2.44 (s, 3H); $^{13}$C NMR (75 MHz, DMSO-d$_6$) δ 162.0, 161.8, 156.0, 151.4, 146.0, 145.7, 140.2, 140.0, 129.7, 129.5, 128.7, 127.6, 127.2, 127.2, 120.1, 118.4, 107.8, 43.1, 17.4; (ES+) m/z 445.1 (M+1).

Example 3.15

Synthesis of N-Benzyl-4-methyl-2-(2-oxo-5-(phenylcarbamoyl)pyridin-1(2H)-yl)thiazole-5-carboxamide

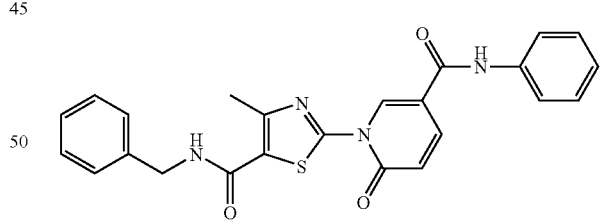

Following the procedure as described in Example 3, making variations only as required to use 6-oxo-N-phenyl-1,6-dihydropyridine-3-carboxamide in place of 4-aminopyridin-2(1H)-one to react with N-benzyl-2-bromo-4-methylthiazole-5-carboxamide, the title compound was obtained as a colorless solid in 31% yield: mp 223-225° C. (hexane/ethyl acetate); $^1$H-NMR (300 MHz, DMSO-d$_6$) δ 10.39 (s, 1H), 9.40 (d, J=2.5 Hz, 1H), 8.89 (t, J=5.9 Hz, 1H), 8.14 (dd, J=9.6, 2.5 Hz, 1H), 7.70-7.68 (m, 2H), 7.36-7.28 (m, 6H), 7.26-7.18 (m, 1H), 7.11-7.07 (m, 1H), 6.86 (d, J=9.6 Hz, 1H), 4.41 (d, J=5.9 Hz, 2H), 2.61 (s, 3H); $^{13}$C NMR (75 MHz, DMSO-d$_6$) δ 162.4, 161.6, 160.1, 153.5, 150.5, 139.7, 139.3, 139.1, 134.0, 129.1, 128.7, 127.7, 127.3, 125.3, 124.4, 121.0, 120.2, 116.2, 43.2, 17.5; (ES+) m/z 445.1 (M+1).

Example 3.16

Synthesis of 4-Methyl-2-(2-oxopyridin-1(2H)-yl)-N-(pyridin-3-ylmethyl)thiazole-5-carboxamide

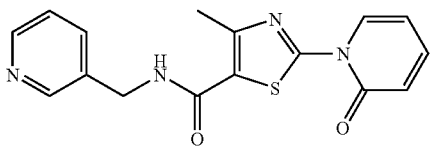 [SMILES: Cc1nc(-n2ccccc2=O)sc1C(=O)NCc1cccnc1]

Following the procedure as described in Example 3, making variations only as required to use pyridin-2(1H)-one in place of 4-aminopyridin-2(1H)-one to react with 2-bromo-4-methyl-N-(pyridin-3-ylmethyl)thiazole-5-carboxamide, the title compound was obtained as a colorless solid in 21% yield: mp 218-220° C. (ethyl acetate/hexanes); $^1$H NMR (300 MHz, DMSO-d$_6$) δ 8.87 (t, J=5.6 Hz, 1H), 8.71 (dd, J=7.3, 1.3 Hz, 1H), 8.56-8.43 (m, 2H), 7.71 (d, J=7.3 Hz, 1H), 7.68-7.59 (m, 1H), 7.38 (br s, 1H), 6.74 (d, J=9.2 Hz, 1H), 6.60-6.55 (m, 1H), 4.42 (d, J=5.7 Hz, 2H), 2.56 (s, 3H); $^{13}$C NMR (75 MHz, DMSO-d$_6$) δ 161.9, 160.2, 153.8, 150.8, 149.3, 148.4, 141.4, 135.5, 131.5, 124.2, 120.9, 108.7, 41.0, 17.5; MS (ES+) m/z 327.2 (M+1).

Example 3.17

Synthesis of 2-(4-(Benzyloxy)-2-oxopyridin-1(2H)-yl)-N-(3,4-difluorobenzyl)-4-methylthiazole-5-carboxamide

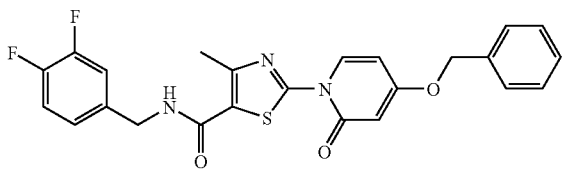 [SMILES: Cc1nc(-n2ccc(OCc3ccccc3)cc2=O)sc1C(=O)NCc1ccc(F)c(F)c1]

Following the procedure as described in Example 3, making variations only as required to use 4-(benzyloxy)pyridin-2(1H)-one in place of 4-aminopyridin-2(1H)-one to react with 2-bromo-N-(3,4-difluorobenzyl)-4-methylthiazole-5-carboxamide, the title compound was obtained as a colorless solid in 85% yield: mp 225-227° C. (ethyl acetate/hexanes); $^1$H NMR (300 MHz, CDCl$_3$) δ 8.67 (d, J=7.9 Hz, 1H), 7.43-7.35 (m, 5H), 7.17-7.05 (m, 3H), 6.35-6.19 (m, 2H), 6.05 (s, 1H), 5.03 (s, 2H), 4.52 (s, 2H), 2.67 (s, 3H); $^{13}$C NMR (75 MHz, CDCl$_3$) δ 167.4, 162.3, 162.0, 153.5, 152.6, 152.1, 151.5, 148.8, 135.0, 134.5, 131.5, 128.8, 127.7, 123.7, 121.8, 117.6, 116.9, 104.1, 97.3, 70.8, 42.9, 17.3; MS (ES+) m/z 468.3 (M+1).

Example 3.18

Synthesis of N-Benzyl-4-methyl-2-(2-oxo-4-(phenoxymethyl)pyridin-1(2H)-yl)thiazole-5-carboxamide

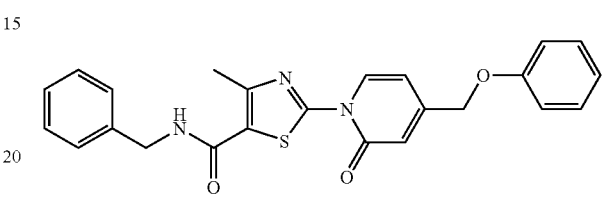

Following the procedure as described in Example 3, making variations only as required to use 4-(benzyloxy)pyridin-2(1H)-one in place of 4-aminopyridin-2(1H)-one to react with N-benzyl-2-bromo-4-methylthiazole-5-carboxamide, the title compound was obtained as a colorless solid in 12% yield: mp 175-177° C. (methanol); $^1$H NMR (300 MHz, CDCl$_3$) δ 8.78 (d, J=7.6 Hz, 1H), 7.37-7.26 (m, 7H), 7.01-6.91 (m, 3H), 6.83-6.82 (m, 1H), 6.48 (dd, J=7.6, 1.8 Hz, 1H), 6.10 (t, J=5.3 Hz, 1H), 4.96 (s, 2H), 4.59 (d, J=5.6 Hz, 2H), 2.70 (m, 3H); $^{13}$C NMR (75 MHz, CDCl$_3$) δ 162.0, 160.3, 157.7, 153.2, 152.3, 150.8, 137.6, 131.2, 129.7, 128.8, 127.9, 127.7, 123.1, 121.7, 117.2, 114.7, 106.3, 67.3, 44.1, 17.3; MS (ES+) m/z 432.3 (M+1).

Example 3.19

Synthesis of N-Benzyl-5-(4-(benzyloxy)-2-oxopyridin-1(2H)-yl)-3-methylfuran-2-carboxamide

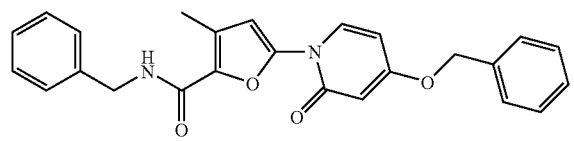 [SMILES: Cc1cc(-n2ccc(OCc3ccccc3)cc2=O)oc1C(=O)NCc1ccccc1]

Following the procedure as described in Example 3, making variations only as required to use 4-(benzyloxy)pyridin-2(1H)-one in place of 4-aminopyridin-2(1H)-one to react with N-benzyl-5-bromo-3-methylfuran-2-carboxamide in place of N-benzyl-2-bromo-4-methylthiazole-5-carboxamide, the title compound was obtained as a colorless solid in 22% yield: mp 191-192° C.; $^1$H NMR (300 MHz, DMSO-d$_6$) δ 8.92 (t, J=6.2 Hz, 1H), 8.23 (d, J=7.9 Hz, 1H), 7.49-7.20 (m, 10H), 6.78 (s, 1H), 6.25 (dd, J=7.9, 2.7 Hz, 1H), 6.06 (d, J=2.7 Hz, 1H), 5.15 (s, 2H), 4.43 (d, J=6.2 Hz, 2H), 2.33 (s, 3H); $^{13}$C NMR (75 MHz, DMSO-d$_6$) δ 166.4, 160.7, 158.3, 143.7, 139.6, 137.1, 135.4, 134.5, 128.4, 128.3, 128.2, 128.0, 127.2, 126.7, 105.6, 101.8, 97.6, 69.9, 41.5, 11.0; MS (ES+) m/z 415.3 (M+1).

Example 3.20

Synthesis of Ethyl 5-(4-(Benzyloxy)-2-oxopyridin-1 (2H)-yl)-3-methylthiophene-2-carboxylate

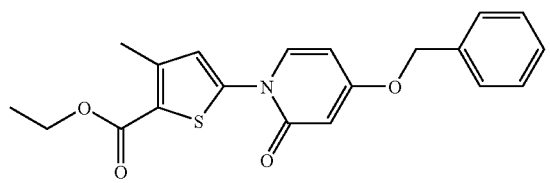 [SMILES: CCOC(=O)c1sc(-n2ccc(OCc3ccccc3)cc2=O)cc1C]

Following the procedure as described in Example 3, making variations only as required to use 4-(benzyloxy)pyridin-2(1H)-one in place of 4-aminopyridin-2(1H)-one to react with ethyl 5-bromo-3-methylthiophene-2-carboxylate in place of N-benzyl-2-bromo-4-methylthiazole-5-carboxamide, the title compound was obtained as a colorless solid in 26% yield: $^1$H NMR (300 MHz, CDCl$_3$) δ 7.55 (d, J=7.8 Hz, 1H), 7.44-7.36 (m, 5H), 6.87 (s, 1H), 6.13 (dd, J=7.8, 2.7 Hz, 1H), 6.07 (d, J=2.7 Hz, 1H), 5.04 (s, 2H), 4.32 (q, J=7.1 Hz, 2H), 2.55 (s, 3H), 1.36 (t, J=7.1 Hz, 3H); MS (ES+) m/z 370.2 (M+1).

Example 3.21

Synthesis of 5-(4-(Benzyloxy)-2-oxopyridin-1(2H)-yl)-N-(4-fluorobenzyl)-3-methylthiophene-2-carboxamide

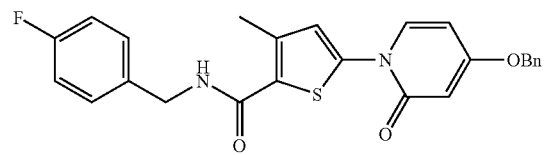 [SMILES: Cc1cc(-n2ccc(OCc3ccccc3)cc2=O)sc1C(=O)NCc1ccc(F)cc1]

Following the procedure as described in Example 3, making variations only as required to use 4-(benzyloxy)pyridin-2(1H)-one in place of 4-aminopyridin-2(1H)-one to react with 5-bromo-N-(4-fluorobenzyl)-3-methylthiophene-2-carboxamide in place of N-benzyl-2-bromo-4-methylthiazole-5-carboxamide, the title compound was obtained as a colorless solid in 28% yield: mp 175-177° C.; $^1$H NMR (300 MHz, CDCl$_3$) δ 7.55 (d, J=7.8 Hz, 1H), 7.43-7.36 (m, 5H), 7.31 (dd, J=8.5, 5.6 Hz, 2H), 7.02 (dd, J=8.5, 8.5 Hz, 2H), 6.84 (s, 1H), 6.20 (t, J=5.4 Hz, 1H), 6.14 (dd, J=7.8, 2.4 Hz, 1H), 6.05 (d, J=2.4 Hz, 1H), 5.03 (s, 2H), 4.54 (d, J=5.4 Hz, 2H), 2.53 (s, 3H); $^{13}$C NMR (75 MHz, CDCl$_3$) δ 166.8, 162.9, 162.2, 139.8, 139.7, 134.7, 134.4, 133.8 ($J_{C-F}$=3.3 Hz), 129.5 ($J_{C-F}$=8.1 Hz), 128.8, 127.8, 126.8, 121.9, 115.6 ($J_{C-F}$=21.4 Hz), 103.4, 98.1, 70.6, 43.2, 15.9; MS (ES+) m/z 449.3 (M+1).

Example 3.22

Synthesis of 5-(4-(Benzyloxy)-2-oxopyridin-1(2H)-yl)-N-(3-fluorobenzyl)-3-methylthiophene-2-carboxamide

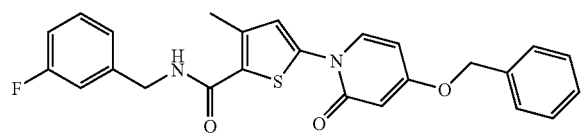 [SMILES: Cc1cc(-n2ccc(OCc3ccccc3)cc2=O)sc1C(=O)NCc1cccc(F)c1]

Following the procedure as described in Example 3, making variations only as required to use 4-(benzyloxy)pyridin-2(1H)-one in place of 4-aminopyridin-2(1H)-one to react with 5-bromo-N-(3-fluorobenzyl)-3-methylthiophene-2-carboxamide in place of N-benzyl-2-bromo-4-methylthiazole-5-carboxamide, the title compound was obtained as a colorless solid in 45% yield: mp 140-141° C.; $^1$H NMR (300 MHz, CDCl$_3$) δ 7.56 (d, J=7.8 Hz, 1H), 7.43-7.27 (m, 6H), 7.11 (d, J=7.8 Hz, 1H), 7.04 (d, J=9.6 Hz, 1H), 7.00-6.92 (m, 1H), 6.84 (s, 1H), 6.29 (t, J=5.7 Hz, 1H), 6.14 (dd, J=7.8, 2.7 Hz, 1H), 6.05 (d, J=2.7 Hz, 1H), 5.02 (s, 2H), 4.58 (d, J=5.7 Hz, 2H), 2.54 (s, 3H); $^{13}$C NMR (75 MHz, CDCl$_3$) δ 166.8, 164.6, 163.0, 163.0 (d, $J_{C-F}$=246.6 Hz), 162.2, 161.3, 140.7 (d, $J_{C-F}$=7.0 Hz), 139.9, 139.7, 134.7, 134.4, 130.2 (d, $J_{C-F}$=8.2 Hz), 128.8, 128.7, 127.8, 126.7, 123.2 (d, $J_{C-F}$=2.9 Hz), 121.9, 114.6 (d, $J_{C-F}$=15.2 Hz), 114.3 (d, $J_{C-F}$=14.4 Hz), 103.4, 98.1, 70.6, 43.3, 15.9; MS (ES+) m/z 449.3 (M+1).

Example 3.23

Synthesis of 5-(4-(Benzyloxy)-2-oxopyridin-1(2H)-yl)-N-ethyl-3-methylthiophene-2-carboxamide

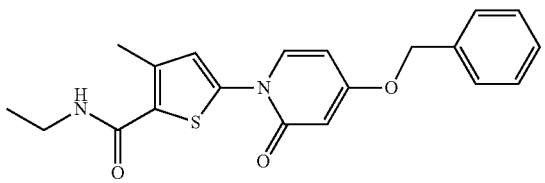 [SMILES: CCNC(=O)c1sc(-n2ccc(OCc3ccccc3)cc2=O)cc1C]

Following the procedure as described in Example 3, making variations only as required to use 4-(benzyloxy)pyridin-2(1H)-one in place of 4-aminopyridin-2(1H)-one to react with 5-bromo-N-ethyl-3-methylthiophene-2-carboxamide in place of N-benzyl-2-bromo-4-methylthiazole-5-carboxamide, the title compound was obtained as a light yellow solid in 45% yield: mp 158-160° C.; $^1$H NMR (300 MHz, CDCl$_3$) δ 7.54 (d, J=7.8 Hz, 1H), 7.43-7.36 (m, 5H), 6.82 (s, 1H), 6.13 (dd, J=7.8, 2.7 Hz, 1H), 6.06 (d, J=2.7 Hz, 1H), 5.84 (br s, 1H), 5.04 (s, 2H), 3.49-3.38 (m, 2H), 2.51 (s, 3H), 1.22 (t, J=7.3 Hz, 3H); $^{13}$C NMR (75 MHz, CDCl$_3$) δ 166.8, 162.9, 162.3, 139.4, 139.0, 134.8, 134.7, 128.8, 128.6, 127.7, 127.5, 122.2, 103.2, 98.2, 70.6, 34.8, 15.8, 14.9; MS (ES+) m/z 369.3 (M+1).

Example 3.24

Synthesis of 4-Methyl-2-(2-oxo-4-(trifluoromethyl)pyridin-1(2H)-yl)-N-(pyridin-3-ylmethyl)thiazole-5-carboxamide

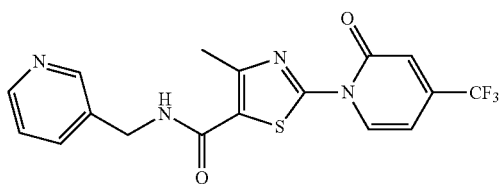 [SMILES: Cc1nc(-n2ccc(C(F)(F)F)cc2=O)sc1C(=O)NCc1cccnc1]

Following the procedure as described in Example 3, making variations only as required to use 4-(benzyloxy)pyridin-2(1H)-one in place of 4-aminopyridin-2(1H)-one to react with 2-bromo-4-methyl-N-(pyridin-3-ylmethyl)thiazole-5-carboxamide in place of N-benzyl-2-bromo-4-methylthiazole-5-carboxamide, the title compound was obtained as a colorless solid in 52% yield: mp 172-173° C.; $^1$H NMR (300 MHz, CDCl$_3$) δ 8.93 (d, J=7.2 Hz, 1H), 8.13 (br s, 1H), 7.12-6.54, (m, 3H), 4.92 (br s, 2H), 2.69 (s, 3H); $^{13}$C NMR (75 MHz, CDCl$_3$) δ 162.1, 159.3, 152.7, 152.6, 141.5, 141.0, 133.1, 127.1, 123.7, 119.9, 119.1, 119.0, 103.1, 44.2, 17.4; MS (ES+) m/z 395.2 (M+1).

Example 3.25

Synthesis of 2-(4-(Benzyloxy)-2-oxopyridin-1(2H)-yl)-4-methyl-N-(pyridin-3-ylmethyl)thiazole-5-carboxamide

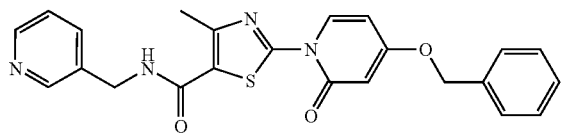 [SMILES: Cc1nc(-n2ccc(OCc3ccccc3)cc2=O)sc1C(=O)NCc1cccnc1]

Following the procedure as described in Example 3, making variations only as required to use 4-(benzyloxy)pyridin-2(1H)-one in place of 4-aminopyridin-2(1H)-one to react with 2-bromo-4-methyl-N-(pyridin-3-ylmethyl)thiazole-5-carboxamide in place of N-benzyl-2-bromo-4-methylthiazole-5-carboxamide, the title compound was obtained as a colorless solid in 47% yield: mp 208-209° C.; $^1$H-NMR (300 MHz, DMSO-d$_6$) δ 8.86 (br s, 1H), 8.68-8.60 (m, 1H), 7.81-7.72 (m, 1H), 7.51-7.33 (m, 7H), 6.35-6.48 (m, 1H), 6.27 (s, 1H), 5.19 (s, 2H), 4.47 (s, 2H), 2.58 (s, 3H); $^{13}$C NMR (75 MHz, DMSO-d$_6$) δ 167.0, 161.5, 161.1, 153.5, 150.1, 135.2, 131.6, 128.5, 128.3, 128.0, 122.9, 103.9, 97.0, 70.3, 17.0; MS (ES+) m/z: 433.3 (M+1).

Example 4

Synthesis of 2-(4-Benzamido-2-oxopyridin-1(2H)-yl)-N-benzyl-4-methylthiazole-5-carboxamide

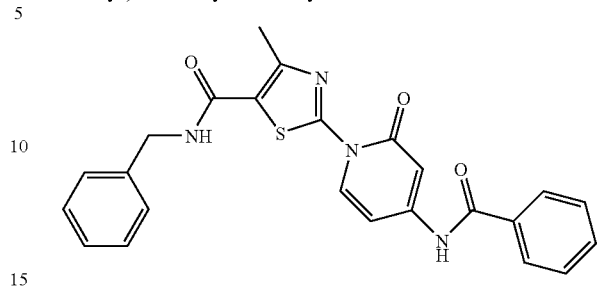

To a mixture of 2-(4-amino-2-oxopyridin-1(2H)-yl)-N-benzyl-4-methylthiazole-5-carboxamide (0.17 g, 0.50 mmol) and 4-dimethylaminopyridine (0.01 g) in pyridine (10 mL) was added benzoyl chloride (0.07 mL, 0.60 mmol) at 0° C. The reaction mixture was stirred at ambient temperature for 6 hours, and water (100 mL) was added. The title compound was precipitated as a solid which was collected by filtration and washed with water and t-butylmethyl ether (0.17 g, 76%): mp 246-248° C.; $^1$H NMR (300 MHz, DMSO-d$_6$) δ 10.66 (s, 1H), 8.78 (t, J=5.7 Hz, 1H), 8.67 (d, J=7.8 Hz, 1H), 7.95-7.90 (m, 2H), 7.66-7.47 (m, 3H), 7.35-7.18 (m, 6H), 6.94 (dd, J=7.8, 2.1 Hz, 1H), 4.39 (d, J=5.7 Hz, 2H), 2.55 (s, 3H); $^{13}$C NMR (75 MHz, DMSO-d$_6$) δ 167.4, 161.9, 161.0, 153.8, 150.3, 149.4, 139.8, 134.1, 132.9, 131.6, 129.0, 128.7, 128.4, 127.7, 127.2, 123.9, 104.2, 103.9, 43.1, 17.5; MS (ES+) m/z 445.3 (M+1).

Example 5

Synthesis of N-benzyl-2-(4-(benzylamino)-2-oxopyridin-1(2H)-yl)-4-methylthiazole-5-carboxamide

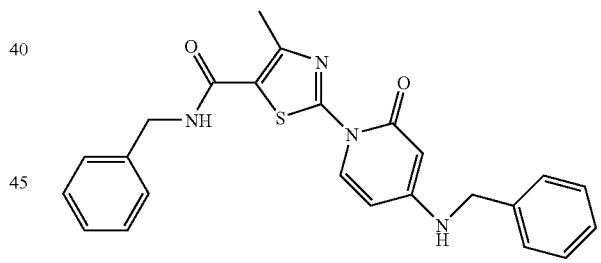

To a solution of 2-(4-amino-2-oxopyridin-1(2H)-yl)-N-benzyl-4-methylthiazole-5-carboxamide (0.30 g, 0.88 mmol) and trifluoroacetic acid (15 mL) in chloroform (20 mL) was added benzaldehyde (0.10 mL, 0.98 mmol). The reaction mixture was stirred for 15 minutes at ambient temperature, then triethylsilane (0.15 mL, 1.00 mmol) was added. The reaction mixture was kept stirring for 2 hours at ambient temperature, then another portion of benzaldehyde (0.10 mL, 0.98 mmol) and triethylsilane (0.15 mL, 1.00 mmol) was added. The reaction mixture was kept stirring for another 2 hours at ambient temperature. The solvent was removed in vacuo, and the residue was washed with saturated aqueous sodium bicarbonate solution, water and t-butylmethyl ether to afford the title compound (0.30 g, 79%): mp 253-255° C.; $^1$H NMR (300 MHz, DMSO-d$_6$) δ 8.68 (t, J=5.7 Hz, 1H), 8.39 (d, J=7.8 Hz, 1H), 7.87 (s, 1H), 7.44-7.21 (m, 10H), 6.21 (d, J=7.8 Hz, 1H), 5.31 (s, 1H), 4.36 (d, J=5.7 Hz, 2H), 4.31 (d, J=4.5 Hz, 2H), 2.50 (s, 3H); $^{13}$C NMR (75 MHz, DMSO-d$_6$)

δ 162.1, 160.9, 155.9, 154.5, 150.2, 140.0, 138.3, 130.6, 128.9, 128.7, 127.7, 127.6, 127.1, 122.8, 103.6, 88.6, 46.0, 43.0, 17.5; MS (ES+) m/z 431.2 (M+1).

Example 6

Synthesis of N-Benzyl-4-methyl-2-(2-oxo-4-(pyridin-3-ylmethoxy)pyridin-1(2H)-yl)thiazole-5-carboxamide

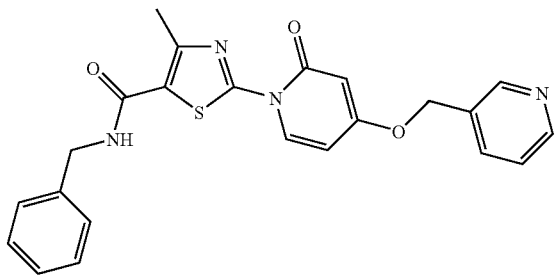 [SMILES: Cc1nc(-n2ccc(OCc3cccnc3)cc2=O)sc1C(=O)NCc1ccccc1]

To a solution of N-benzyl-2-(4-hydroxy-2-oxopyridin-1(2H)-yl)-4-methylthiazole-5-carboxamide (0.10 g, 0.29 mmol) in N,N-dimethylformamide (4 mL) was added sodium hydride (60% dispersion in mineral oil, 0.028 g, 0.70 mmol) slowly at 0° C. The reaction mixture was stirred for 5 minutes and then 3-(bromomethyl)pyridine hydrobromide (0.096 g, 0.38 mmol) and tetra-n-butylammonium iodide (0.005 g, 0.014 mmol) were added at 0° C. After stirred at ambient temperature for 16 hours, the reaction mixture was concentrated in vacuo to yield a solid residue. The crude product was purified by column chromatography eluted with ethyl acetate/hexanes (50/50 to 100/0) to afford the title compound as a white solid (0.018 g, 14% yield): mp 214-216° C.; $^1$H NMR (300 MHz, DMSO-$d_6$) δ 8.81-8.61 (m, 4H), 7.98 (d, J=7.8 Hz, 1H), 7.55-7.51 (m, 1H), 7.33-7.19 (m, 5H), 6.42-6.39 (m, 1H), 6.28 (d, J=2.7 Hz, 1H), 5.25 (s, 2H), 5.39 (d, J=5.7 Hz, 2H), 2.55 (s, 3H); $^{13}$C NMR (75 MHz, DMSO-$d_6$) δ 167.3, 161.9, 161.6, 153.9, 150.3, 149.1, 148.7, 139.9, 137.8, 132.3, 128.8, 127.7, 127.2, 124.7, 123.8, 104.3, 97.7, 68.3, 17.5; MS (ES+) m/z 433.2 (M+1).

Example 6.1

Synthesis of N-Benzyl-4-methyl-2-(2-oxo-4-(pyridin-2-ylmethoxy)pyridin-1(2H)-yl)thiazole-5-carboxamide

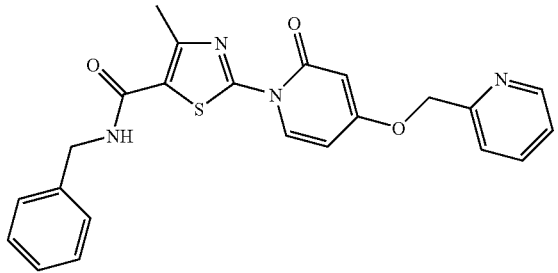 [SMILES: Cc1nc(-n2ccc(OCc3ccccn3)cc2=O)sc1C(=O)NCc1ccccc1]

Following the procedure as described in Example 6, making variations only as required to use 2-(bromomethyl)pyridine hydrobromide in place of 3-(bromomethyl)pyridine hydrobromide to react with N-benzyl-2-(4-hydroxy-2-oxopyridin-1(2H)-yl)-4-methylthiazole-5-carboxamide, the title compound was obtained as a white solid in 11% yield: mp 202-205° C.; $^1$H NMR (300 MHz, CDCl$_3$/CD$_3$OD) δ 8.69 (m, 1H), 8.53 (m, 1H), 7.89-7.84 (m, 1H), 7.56-7.49 (m, 2H), 7.39-7.35 (m, 1H), 7.28-7.17 (m, 5H), 6.36-6.32 (m, 1H), 6.07 (d, J=2.7 Hz, 1H), 5.18 (s, 2H), 4.46 (s, 2H), 2.56 (s, 3H); $^{13}$C NMR (75 MHz, CDCl$_3$/CD$_3$OD) δ 170.1, 165.7, 164.9, 156.7, 156.3, 154.0, 150.6, 141.9, 140.9, 134.7, 131.1, 130.0, 129.8, 126.8, 126.0, 125.5, 106.6, 100.1, 72.6, 46.2, 19.4; MS (ES+) m/z 433.3 (M+1).

Example 7

Synthesis of N-Benzyl-2-(3-hydroxy-2-oxopyridin-1(2H)-yl)-4-methylthiazole-5-carboxamide

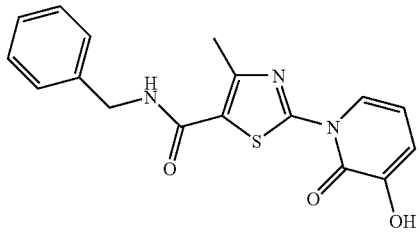 [SMILES: Cc1nc(-n2cccc(O)c2=O)sc1C(=O)NCc1ccccc1]

A mixture of N-benzyl-2-(3-(benzyloxy)-2-oxopyridin-1(2H)-yl)-4-methylthiazole-5-carboxamide (0.14 g, 0.32 mmol) and 20 wt. % palladium on activated carbon (0.10 g) in methanol (50 mL) was stirred under an atmosphere of hydrogen for 2 hours. The mixture was filtered and the filtrate was concentrated in vacuo. The residue was purified by column chromatography followed by recrystallization from methanol (10 mL) to afford the title compound (0.027 g, 8%): mp 225-228° C.; $^1$H NMR (300 MHz, CD$_3$OD) δ 8.63 (d, J=7.6 Hz, 1H), 7.42-7.26 (m, 5H), 6.20-6.10 (m, 1H), 5.87-5.83 (m, 1H), 4.36 (d, J=6.0 Hz, 2H), 2.58 (s, 3H); MS (ES+) m/z 342.2 (M+1).

Example 7.1

Synthesis of N-Benzyl-2-(5-hydroxy-1-oxoisoquinolin-2(1H)-yl)-4-methylthiazole-5-carboxamide

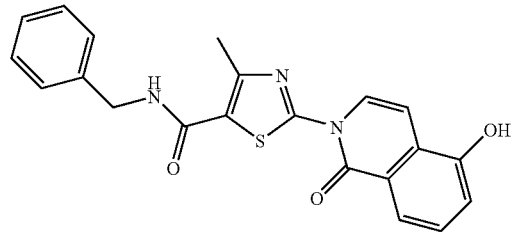 [SMILES: Cc1nc(-n2ccc3c(O)cccc3c2=O)sc1C(=O)NCc1ccccc1]

Following the procedure as described in Example 7, making variations only as required to use N-benzyl-2-(5-(benzyloxy)-1-oxoisoquinolin-2(1H)-yl)-4-methylthiazole-5-carboxamide in place of N-benzyl-2-(3-(benzyloxy)-2-oxopyridin-1(2H)-yl)-4-methylthiazole-5-carboxamide, the title compound was obtained as a white solid in 18% yield:

mp 218-221° C.; $^1$H NMR (300 MHz, CD$_3$OD) δ 7.74 (d, J=6.0 Hz, 1H), 7.35-7.23 (m, 6H), 7.12-7.08 (m, 2H), 6.97 (d, J=6.0 Hz, 1H), 4.50 (s, 2H), 2.57 (s, 3H); $^{13}$C NMR (75 MHz, CD$_3$OD) δ 162.1, 159.6, 153.5, 151.3, 136.7, 134.9, 128.3, 126.7, 126.6, 125.6, 125.4, 125.3, 125.3, 124.2, 115.5, 114.2, 99.8, 41.7, 14.1; MS (ES+) m/z 392.3 (M+1).

Example 7.2

Synthesis of N-Benzyl-2-(6-hydroxy-1-oxoisoquinolin-2(1H)-yl)-4-methylthiazole-5-carboxamide

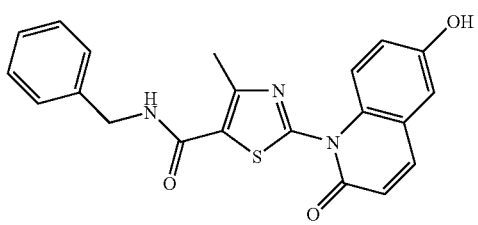 [SMILES: Cc1nc(-n2c(=O)ccc3cc(O)ccc32)sc1C(=O)NCc1ccccc1]

Following the procedure as described in Example 7, making variations only as required to use N-benzyl-2-(6-(benzyloxy)-1-oxoisoquinolin-2(1H)-yl)-4-methylthiazole-5-carboxamide in place of N-benzyl-2-(3-(benzyloxy)-2-oxopyridin-1(2H)-yl)-4-methylthiazole-5-carboxamide, the title compound was obtained as a white solid in 18% yield: mp 225-228° C.; $^1$H NMR (300 MHz, CD$_3$OD) δ 7.84 (d, J=9.0 Hz, 1H), 7.34-7.22 (m, 6H), 7.10-7.06 (m, 1H), 7.01 (m, 1H), 6.58 (d. J=9.0 Hz, 1H), 4.50 (s, 2H), 2.58 (s, 3H); $^{13}$C NMR (75 MHz, DMSO-d$_6$) δ 161.3, 159.7, 154.5, 151.9, 139.6, 138.9, 132.1, 129.9, 128.3, 127.2, 126.9, 121.9, 119.9, 119.7, 116.1, 111.4, 42.8, 16.8; MS (ES+) m/z 392.2 (M+1).

Example 7.3

Synthesis of N-Benzyl-5-(4-hydroxy-2-oxopyridin-1(2H)-yl)thiophene-3-carboxamide

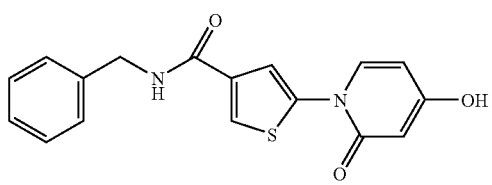 [SMILES: O=C(NCc1ccccc1)c1csc(-n2ccc(O)cc2=O)c1]

Following the procedure as described in Example 7, making variations only as required to use N-benzyl-5-(4-(benzyloxy)-2-oxopyridin-1(2H)-yl)thiophene-3-carboxamide in place of N-benzyl-2-(3-(benzyloxy)-2-oxopyridin-1(2H)-yl)-4-methylthiazole-5-carboxamide, the title compound was obtained as a white solid in 10% yield: mp 150° C. (dec.); $^1$H NMR (300 MHz, DMSO-d$_6$) δ 8.83 (t, J=5.8 Hz, 1H), 7.93 (s, 1H), 7.91 (s, 1H), 7.61 (s, 1H), 7.37-7.20 (m, 5H), 6.00 (d, J=6.8 Hz, 1H), 5.55 (s, 1H), 4.45 (d, J=5.8 Hz, 2H); MS (ES+) m/z 327.2 (M+1).

Example 7.4

Synthesis of N-Benzyl-5-(4-hydroxy-2-oxopyridin-1(2H)-yl)-3-methylthiophene-2-carboxamide

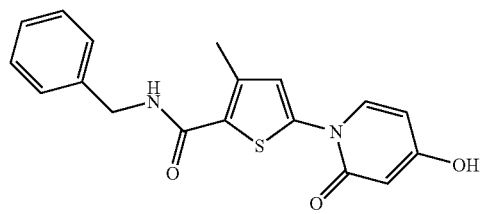 [SMILES: Cc1cc(-n2ccc(O)cc2=O)sc1C(=O)NCc1ccccc1]

Following the procedure as described in Example 7, making variations only as required to use N-benzyl-5-(4-(benzyloxy)-2-oxopyridin-1(2H)-yl)-3-methylthiophene-2-carboxamide in place of N-benzyl-2-(3-(benzyloxy)-2-oxopyridin-1(2H)-yl)-4-methylthiazole-5-carboxamide, the title compound was obtained as a white solid in 87% yield: mp 98° C. (dec.); $^1$H NMR (300 MHz, DMSO-d$_6$) δ 8.54 (t, J=5.9 Hz, 1H), 8.10 (d, J=7.8 Hz, 1H), 7.37-7.22 (m, 5H), 7.20 (s, 1H), 6.12 (dd, J=7.8, 2.5 Hz, 1H), 5.75 (d, J=2.5 Hz, 1H), 4.40 (d, J=5.9 Hz, 2H), 2.41 (s, 3H); $^{13}$C NMR (75 MHz, DMSO-d$_6$) δ 166.8, 162.5, 161.1, 139.7, 139.1, 137.1, 135.4, 128.2, 127.1, 126.6, 120.1, 102.8, 97.8, 42.5, 15.6; MS (ES+) m/z 341.1 (M+1).

Example 7.5

Synthesis of N-Benzyl-2-(4-hydroxy-2-oxopyridin-1(2H)-yl)-4-methylthiazole-5-carboxamide

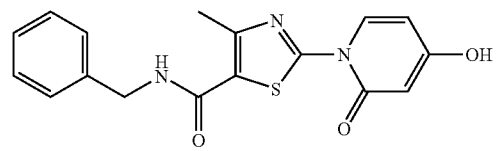 [SMILES: Cc1nc(-n2ccc(O)cc2=O)sc1C(=O)NCc1ccccc1]

Following the procedure as described in Example 7, making variations only as required to use N-benzyl-2-(4-(benzyloxy)-2-oxopyridin-1(2H)-yl)-4-methylthiazole-5-carboxamide in place of N-benzyl-2-(3-(benzyloxy)-2-oxopyridin-1(2H)-yl)-4-methylthiazole-5-carboxamide, the title compound was obtained as a colorless solid in 89% yield: mp 240-243° C. (methanol); $^1$H NMR (300 MHz, DMSO-d$_6$) δ 11.51 (br s, 1H), 8.76 (t, J=5.9 Hz, 1H), 8.59 (d, J=8.0 Hz, 1H), 7.39-7.16 (m, 5H), 6.26 (dd, J=8.0, 2.5 Hz, 1H), 5.81 (d, J=2.5 Hz, 1H), 4.38 (d, J=5.9 Hz, 2H), 2.53 (s, 3H); $^{13}$C NMR (75 MHz, DMSO-d$_6$) δ 167.9, 162.0, 161.6, 154.1, 150.2, 139.9, 132.6, 128.7, 127.7, 127.2, 123.6, 104.4, 98.0, 43.1, 17.5; MS (ES+) m/z 342.2 (M+1).

Example 7.6

Synthesis of 5-(4-Hydroxy-2-oxopyridin-1(2H)-yl)-3-methyl-N-(pyridin-3-ylmethyl)thiophene-2-carboxamide

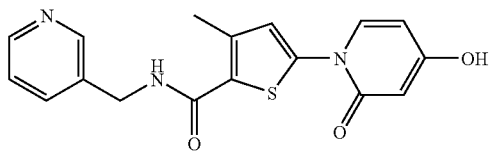 [SMILES: Cc1cc(-n2ccc(O)cc2=O)sc1C(=O)NCc1cccnc1]

Following the procedure as described in Example 7, making variations only as required to use 5-(4-(benzyloxy)-2-oxopyridin-1(2H)-yl)-3-methyl-N-(pyridin-3-ylmethyl)thiophene-2-carboxamide in place of N-benzyl-2-(3-(benzyloxy)-2-oxopyridin-1(2H)-yl)-4-methylthiazole-5-carboxamide, the title compound was obtained as an off-white solid in 14% yield: mp 110° C. (dec.); $^1$H NMR (300 MHz, CD$_3$OD) δ 8.56 (s, 1H), 8.44 (s, 1H), 7.89 (d, J=7.8 Hz, 1H), 7.85 (d, J=7.8 Hz, 1H), 7.42 (dd, J=7.8, 4.9 Hz, 1H), 7.07 (s, 1H), 6.20 (dd, J=7.8, 2.6 Hz, 1H), 5.87 (d, J=2.6 Hz, 1H), 4.56 (s, 2H), 2.47 (s, 3H); $^{13}$C NMR (75 MHz, CD$_3$OD) δ 169.8, 165.7, 164.8, 149.5, 148.8, 141.9, 140.5, 137.73, 137.7, 128.9, 125.3, 125.3, 124.0, 104.8, 99.4, 42.0, 15.9; MS (ES+) m/z 342.2 (M+1).

Example 7.7

Synthesis of N-(4-Fluorobenzyl)-5-(4-hydroxy-2-oxopyridin-1(2H)-yl)-3-methylthiophene-2-carboxamide

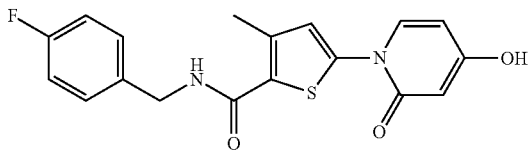 [SMILES: Cc1cc(-n2ccc(O)cc2=O)sc1C(=O)NCc1ccc(F)cc1]

Following the procedure as described in Example 7, making variations only as required to use 5-(4-(benzyloxy)-2-oxopyridin-1(2H)-yl)-N-(4-fluorobenzyl)-3-methylthiophene-2-carboxamide in place of N-benzyl-2-(3-(benzyloxy)-2-oxopyridin-1(2H)-yl)-4-methylthiazole-5-carboxamide, the title compound was obtained as an off-white solid in 76% yield: mp 95° C. (dec); $^1$H NMR (300 MHz, DMSO-d$_6$) δ 11.22 (br s, 1H), 8.53 (t, J=6.0 Hz, 1H), 8.10 (d, J=7.9 Hz, 1H), 7.39-7.30 (m, 2H), 7.21-7.11 (m, 3H), 6.13 (dd, J=7.9, 2.6 Hz, 1H), 5.76 (d, J=2.6 Hz, 1H), 4.38 (d, J=6.0 Hz, 2H), 2.41 (s, 3H); $^{13}$C NMR (75 MHz, DMSO-d$_6$) δ 166.5, 162.5, 161.0, 161.0 (d, J$_{C-F}$=242.0 Hz), 139.1, 137.2, 135.9 (d, J$_{C-F}$=2.9 Hz), 135.5, 129.1 (d, J$_{C-F}$=8.1 Hz), 127.1, 120.2, 114.9 (d, J$_{C-F}$=21.3 Hz), 102.6, 97.9, 41.8, 15.5; MS (ES+) m/z 359.2 (M+1).

Example 7.8

Synthesis of N-(3-Fluorobenzyl)-5-(4-hydroxy-2-oxopyridin-1(2H)-yl)-3-methylthiophene-2-carboxamide

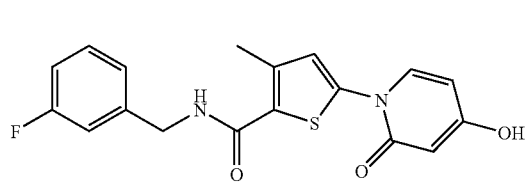 [SMILES: Cc1cc(-n2ccc(O)cc2=O)sc1C(=O)NCc1cccc(F)c1]

Following the procedure as described in Example 7, making variations only as required to use 5-(4-(benzyloxy)-2-oxopyridin-1(2H)-yl)-N-(3-fluorobenzyl)-3-methylthiophene-2-carboxamide in place of N-benzyl-2-(3-(benzyloxy)-2-oxopyridin-1(2H)-yl)-4-methylthiazole-5-carboxamide, the title compound was obtained as a colorless solid in 76% yield: mp 140-142° C.; $^1$H NMR (300 MHz, DMSO-d$_6$) δ 11.24 (br s, 1H), 8.56 (t, J=6.0 Hz, 1H), 8.11 (d, J=7.9 Hz, 1H), 7.42-7.34 (m, 1H), 7.21 (s, 1H), 7.18-7.02 (m, 3H), 6.13 (dd, J=7.9, 2.6 Hz, 1H), 5.77 (d, J=2.6 Hz, 1H), 4.41 (d, J=6.0 Hz, 2H), 2.42 (s, 3H); $^{13}$C NMR (75 MHz, DMSO-d$_6$) δ 166.5, 162.6, 162.1 (d, J$_{C-F}$=241.5 Hz), 161.0, 142.7 (d, J$_{C-F}$=7.0 Hz), 139.2, 137.3, 135.4, 130.1 (d, J$_{C-F}$=8.3 Hz), 126.9, 123.1 (d, J$_{C-F}$=2.6 Hz), 120.2, 113.8 (d, J$_{C-F}$=21.5 Hz), 113.4 (d, J$_{C-F}$=20.9 Hz), 102.6, 97.9, 42.1, 15.5; MS (ES+) m/z 359.2 (M+1).

Example 7.9

Synthesis of N-Ethyl-5-(4-hydroxy-2-oxopyridin-1(2H)-yl)-3-methylthiophene-2-carboxamide

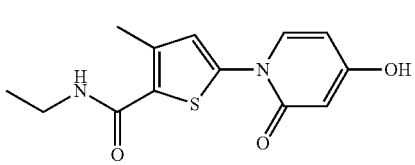 [SMILES: CCNC(=O)c1sc(-n2ccc(O)cc2=O)cc1C]

Following the procedure as described in Example 7, making variations only as required to use 5-(4-(benzyloxy)-2-oxopyridin-1(2H)-yl)-N-ethyl-3-methylthiophene-2-carboxamide in place of N-benzyl-2-(3-(benzyloxy)-2-oxopyridin-1(2H)-yl)-4-methylthiazole-5-carboxamide, the title compound was obtained as an off-white solid in 80% yield: mp 183-184° C.; $^1$H NMR (300 MHz, DMSO-d$_6$) δ 11.8 (br s, 1H), 8.07 (d, J=7.9 Hz, 1H), 7.94 (t, J=5.5 Hz, 1H), 7.16 (s, 1H), 6.12 (dd, J=7.9, 2.6 Hz, 1H), 5.76 (d, J=2.6 Hz, 1H), 3.27-3.16 (m, 2H), 2.39 (s, 3H), 1.09 (t, J=7.2 Hz, 3H);

$^{13}$C NMR (75 MHz, DMSO-d$_6$) δ 166.5, 162.2, 161.0, 138.9, 136.4, 135.6, 127.8, 120.2, 102.5, 97.9, 33.9, 15.4, 14.8; MS (ES+) m/z 279.2 (M+1).

Example 7.10

Synthesis of 2-(4-Hydroxy-2-oxopyridin-1(2H)-yl)-4-methyl-N-(pyridin-3-ylmethyl)thiazole-5-carboxamide

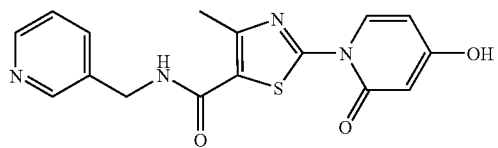 [SMILES: Cc1nc(-n2ccc(O)cc2=O)sc1C(=O)NCc1cccnc1]

Following the procedure as described in Example 7, making variations only as required to use 2-(4-(benzyloxy)-2-oxopyridin-1(2H)-yl)-4-methyl-N-(pyridin-3-ylmethyl)thiazole-5-carboxamide in place of N-benzyl-2-(3-(benzyloxy)-2-oxopyridin-1(2H)-yl)-4-methylthiazole-5-carboxamide, the title compound was obtained as yellowish solid in 34% yield: mp 238-240° C.; $^1$H NMR (300 MHz, DMSO-d$_6$) δ 8.78 (t, J=4.8 Hz, 1H), 8.55 (d, J=7.9 Hz, 1H), 8.53 (br s, 1H), 7.74-7.64 (m, 2H), 7.35 (br s, 1H), 6.22 (dd, J=7.9, 1.3 Hz, 1H), 5.74 (d, J=1.3 Hz, 1H), 4.40 (d, J=4.8 Hz, 2H), 2.52 (s, 3H); $^{13}$C NMR (75 MHz, DMSO-d$_6$) δ 168.9, 162.2, 161.7, 154.4, 150.5, 132.4, 123.2, 105.2, 97.7, 40.9, 17.6; MS (ES+) m/z: 343.2 (M+1).

Example 8

Synthesis of N-Benzyl-5-(4-(benzyloxy)-2-oxopyridin-1(2H)-yl)thiophene-3-carboxamide

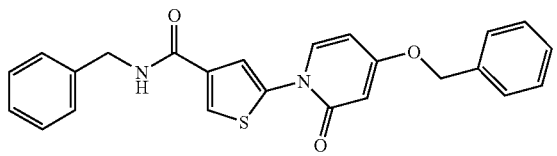 [SMILES: O=C(NCc1ccccc1)c1csc(-n2ccc(OCc3ccccc3)cc2=O)c1]

A mixture of N-benzyl-5-bromothiophene-3-carboxamide (0.57 g, 1.91 mmol), 4-(benzyloxy)pyridin-2(1H)-one (0.42 g, 2.10 mmol), copper(I) iodide (0.055 g, 0.29 mmol), 8-hydroxyquinoline (0.042 g, 0.29 mmol) and potassium carbonate (0.40 g, 2.87 mmol) in N,N-dimethylformamide (15 mL) was stirred at 130° C. for 17 h under nitrogen atmosphere. The reaction mixture was allowed to cool to ambient temperature, and then diluted with ethyl acetate (50 mL). The organic layer was washed with water (2×25 mL), dried over sodium sulfate and filtered. The filtrate was concentrated in vacuo and the residue was purified by column chromatography eluting with 10-80% ethyl acetate in hexanes to afford the title compound as a white solid (0.14 g, 18%): mp 162-163° C.; $^1$H NMR (300 MHz, DMSO-d$_6$) δ 8.55 (t, J=6.0 Hz, 1H), 8.07 (d, J=7.9 Hz, 1H), 8.00 (d, J=1.5 Hz, 1H), 7.71 (d, J=1.5 Hz, 1H), 7.49-7.20 (m, 10H), 6.26 (dd, J=7.8, 2.7 Hz, 1H), 6.11 (d, J=2.7 Hz, 1H), 5.16 (s, 2H), 4.46 (d, J=6.0 Hz, 2H); MS (ES+) m/z 417.2 (M+1).

Example 8.1

Synthesis of N-Benzyl-5-(4-(benzyloxy)-2-oxopyridin-1(2H)-yl)-3-methylthiophene-2-carboxamide

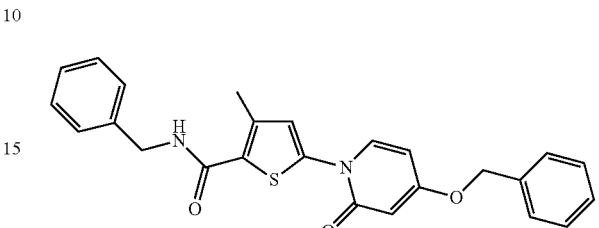

Following the procedure as described in Example 8, making variations only as required to use N-benzyl-5-bromo-3-methylthiophene-2-carboxamide in place of N-benzyl-5-bromothiophene-3-carboxamide to react with 4-(benzyloxy)pyridin-2(1H)-one, the title compound was obtained as colorless solid in 49% yield: mp 153-154° C.; $^1$H NMR (300 MHz, CDCl$_3$) δ 7.55 (d, J=7.9 Hz, 1H), 7.43-7.27 (m, 10H), 6.84 (s, 1H), 6.20-6.11 (m, 2H), 6.05 (d, J=2.7 Hz, 1H), 5.03 (s, 2H), 4.59 (d, J=5.7 Hz, 2H), 2.54 (s, 3H); $^{13}$C NMR (75 MHz, CDCl$_3$) δ 166.4, 162.5, 161.9, 139.2, 137.6, 134.2, 128.43, 128.40, 128.3, 127.5, 127.4, 127.2, 126.7, 121.8, 102.9, 97.8, 70.3, 43.6, 15.6; MS (ES+) m/z 431.3 (M+1).

Example 9

Synthesis of N-Benzyl-5-(4-(2-cyclopropylethoxy)-2-oxopyridin-1(2H)-yl)-3-methylthiophene-2-carboxamide

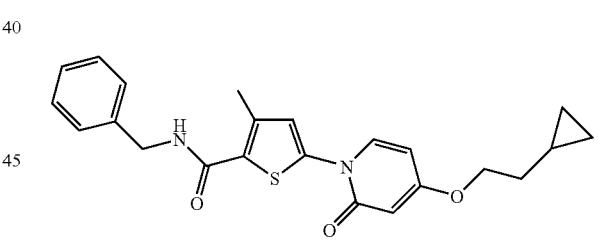

To a stirred solution of N-benzyl-5-(4-hydroxy-2-oxopyridin-1(2H)-yl)-3-methylthiophene-2-carboxamide (0.20 g, 0.59 mmol) in N,N-dimethylformamide (4 mL) at ambient temperature was added potassium carbonate (0.082 g, 0.59 mmol), followed by the addition of 2-cyclopropylethyl 4-methylbenzenesulfonate (0.13 g, 0.59 mmol). The reaction mixture was stirred at 70° C. for 2 hours, and then allowed to cool to ambient temperature and partitioned between ethyl acetate (50 mL) and water (25 mL). The organic layer was washed with brine (25 mL), dried over anhydrous sodium sulfate and filtered. The filtrate was concentrated in vacuo. The residue was purified by column chromatography eluting with 40% ethyl acetate in hexanes to afford the title compound as a colorless solid (0.14 g, 58%): mp 134-136° C.; $^1$H NMR (300 MHz, CDCl$_3$) δ 7.52 (d, J=7.8 Hz, 1H), 7.36-7.27 (m, 5H), 6.83 (s, 1H), 6.18 (t, J=5.6 Hz, 1H), 6.06 (dd, J=7.8, 2.6 Hz, 1H), 5.95 (d, J=2.7 Hz, 1H), 4.58 (d, J=5.6 Hz, 2H), 4.02 (t, J=6.6 Hz, 2H), 2.53 (s, 3H), 1.72-1.64 (m, 2H), 0.89-0.73 (m, 1H), 0.55-0.45 (m, 2H), 0.15-0.08 (m, 2H); $^{13}$C NMR (75 MHz, CDCl$_3$) δ 167.2, 162.9, 162.3, 139.7, 139.6, 138.0, 134.3, 128.7, 127.8, 127.5, 126.9, 121.9, 103.4, 97.4, 68.8, 43.9, 33.6, 15.9, 7.6, 4.2; MS (ES+) m/z 409.3 (M+1).

Example 9.1

Synthesis of N-Benzyl-3-methyl-5-(2-oxo-4-(4-(trifluoromethyl)benzyloxy)pyridin-1(2H)-yl)thiophene-2-carboxamide

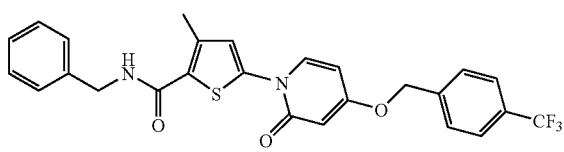 [SMILES: Cc1cc(-n2ccc(OCc3ccc(C(F)(F)F)cc3)cc2=O)sc1C(=O)NCc1ccccc1]

Following the procedure as described in Example 9, making variations only as required to use 1-(bromomethyl)-4-(trifluoromethyl)benzene in place of 2-cyclopropylethyl 4-methylbenzenesulfonate to react with N-benzyl-5-(4-hydroxy-2-oxopyridin-1(2H)-yl)-3-methylthiophene-2-carboxamide, the title compound was obtained as a colorless solid in 42% yield: mp 225-227° C.; $^1$H NMR (300 MHz, DMSO-d$_6$) δ 8.56 (t, J=6.0 Hz, 1H), 8.18 (d, J=7.9 Hz, 1H), 7.80 (d, J=8.2 Hz, 2H), 7.68 (d, J=8.1 Hz, 2H), 7.37-7.20 (m, 6H), 6.32 (dd, J=7.9, 2.8 Hz, 1H), 6.14 (d, J=2.8 Hz, 1H), 5.30 (s, 2H), 4.41 (d, J=6.0 Hz, 2H), 2.42 (s, 3H); $^{13}$C NMR (75 MHz, DMSO-d$_6$) δ 166.0, 162.4, 160.9, 140.3, 139.6, 138.7, 137.2, 135.2, 128.2 (d, $J_{C-F}$=3.7 Hz), 127.4, 127.1, 126.6, 125.4 (d, $J_{C-F}$=3.8 Hz), 120.7, 102.4, 97.5, 69.0, 42.5, 15.5; MS (ES+) m/z 499.3 (M+1).

Example 9.2

Synthesis of N-Benzyl-5-(4-(4-fluorobenzyloxy)-2-oxopyridin-1(2H)-yl)-3-methylthiophene-2-carboxamide

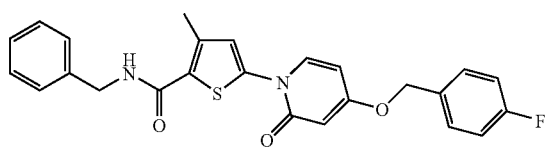 [SMILES: Cc1cc(-n2ccc(OCc3ccc(F)cc3)cc2=O)sc1C(=O)NCc1ccccc1]

Following the procedure as described in Example 9, making variations only as required to use 1-(bromomethyl)-4-fluorobenzene in place of 2-cyclopropylethyl 4-methylbenzenesulfonate to react with N-benzyl-5-(4-hydroxy-2-oxopyridin-1(2H)-yl)-3-methylthiophene-2-carboxamide, the title compound was obtained as a pale yellow solid in 43% yield: mp 195-197° C.; $^1$H NMR (300 MHz, DMSO-d$_6$) δ 8.56 (t, J=6.0 Hz, 1H), 8.16 (d, J=8.0 Hz, 1H), 7.55-7.49 (m, 2H), 7.37-7.20 (m, 8H), 6.28 (dd, J=7.9, 2.7 Hz, 1H), 6.15 (d, J=2.7 Hz, 1H), 5.14 (s, 2H), 4.41 (d, J=6.0 Hz, 2H), 2.42 (s, 3H); $^{13}$C NMR (75 MHz, DMSO-d$_6$) δ 166.2, 162.4, 160.9, 139.6, 138.8, 137.2, 135.2, 135.1, 131.7 (d, $J_{C-F}$=3.0 Hz), 130.4 (d, $J_{C-F}$=8.4 Hz), 128.2, 127.3, 127.1, 126.6, 120.6, 115.3 (d, $J_{C-F}$=21.5 Hz), 102.5, 97.3, 69.3, 42.5, 15.5; MS (ES+) m/z 449.3 (M+1).

Example 9.3

Synthesis of N-Benzyl-5-(4-(4-(difluoromethoxy)benzyloxy)-2-oxopyridin-1(2H)-yl)-3-methylthiophene-2-carboxamide

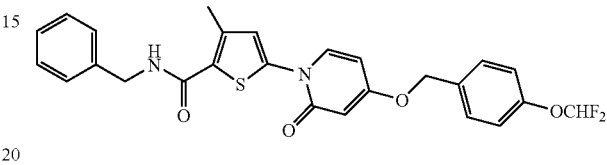

Following the procedure as described in Example 9, making variations only as required to use 1-(bromomethyl)-4-(difluoromethoxy)benzene in place of 2-cyclopropylethyl 4-methylbenzenesulfonate to react with N-benzyl-5-(4-hydroxy-2-oxopyridin-1(2H)-yl)-3-methylthiophene-2-carboxamide, the title compound was obtained as a pinkish solid in 35% yield: mp 178-180° C.; $^1$H NMR (300 MHz, DMSO-d$_6$) δ 8.55 (t, J=6.0 Hz, 1H), 8.16 (d, J=8.0 Hz, 1H), 7.53 (d, J=8.5 Hz, 2H) 7.38-7.20 (m, 9H), 6.28 (dd, J=7.9, 2.7 Hz, 1H), 6.14 (d, J=2.7 Hz, 1H), 5.16 (s, 2H), 4.41 (d, J=6.0 Hz, 2H), 2.42 (s, 3H); $^{13}$C NMR (75 MHz, DMSO-d$_6$) δ 166.1, 162.4, 160.9, 150.8, 139.6, 138.8, 137.2, 135.1, 132.4, 129.9, 128.2, 127.3, 127.4, 127.1, 126.6, 120.6, 118.7, 116.2, 102.5, 97.3, 69.2, 42.5, 15.5; MS (ES+) m/z 497.3 (M+1).

Example 9.4

Synthesis of N-Benzyl-3-methyl-5-(2-oxo-4-phenethoxypyridin-1(2H)-yl)thiophene-2-carboxamide

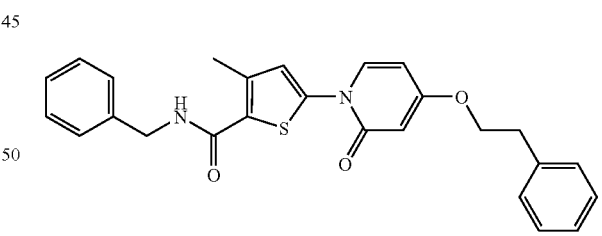

Following the procedure as described in Example 9, making variations only as required to use phenethyl 4-methylbenzenesulfonate in place of 2-cyclopropylethyl 4-methylbenzenesulfonate to react with N-benzyl-5-(4-hydroxy-2-oxopyridin-1(2H)-yl)-3-methylthiophene-2-carboxamide, the title compound was obtained as a colorless solid in 59% yield: mp 159-160° C.; $^1$H NMR (300 MHz, DMSO-d$_6$) δ 8.55 (t, J=5.9 Hz, 1H), 8.12 (d, J=7.9 Hz, 1H), 7.35-7.20 (m, 11H), 6.18 (dd, J=7.9, 2.6 Hz, 1H), 6.06 (d, J=2.6 Hz, 1H), 4.41 (d, J=6.0 Hz, 2H), 4.27 (t, J=6.7 Hz, 2H), 3.04 (t, J=6.6 Hz, 2H), 2.42 (s, 3H); $^{13}$C NMR (75 MHz, DMSO-d$_6$) δ 166.3, 162.4, 161.0, 139.6, 138.8, 137.7, 137.1, 135.0, 128.8, 128.3, 128.2, 127.3, 127.1, 126.6, 126.3, 120.5, 102.4, 96.8, 68.8, 42.5, 34.2, 15.5; MS (ES+) m/z 445.3 (M+1).

Example 9.5

Synthesis of N-Benzyl-5-(4-(cyclopropylmethoxy)-2-oxopyridin-1(2H)-yl)-3-methylthiophene-2-carboxamide

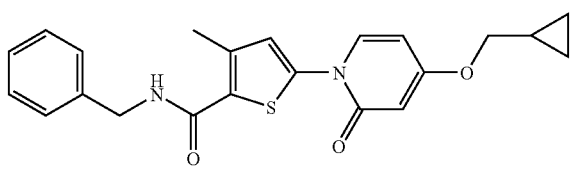 [SMILES: Cc1cc(-n2ccc(OCC3CC3)cc2=O)sc1C(=O)NCc1ccccc1]

Following the procedure as described in Example 9, making variations only as required to use cyclopropylmethyl bromide in place of 2-cyclopropylethyl 4-methylbenzenesulfonate to react with N-benzyl-5-(4-hydroxy-2-oxopyridin-1(2H)-yl)-3-methylthiophene-2-carboxamide, the title compound was obtained as a colorless solid in 62% yield: mp 175-177° C.; $^1$H NMR (300 MHz, DMSO-$d_6$) δ 8.54 (t, J=6.0 Hz, 1H), 8.13 (d, J=8.0 Hz, 1H), 7.35-7.20 (m, 6H), 6.24 (dd, J=8.0, 2.7 Hz, 1H), 5.97 (d, J=2.7 Hz, 1H), 4.41 (d, J=6.0 Hz, 2H), 3.88 (d, J=7.2 Hz, 2H), 2.42 (s, 3H), 1.27-1.14 (m, 1H), 0.63-0.54 (m, 2H), 0.37-0.29 (m, 2H); $^{13}$C NMR (75 MHz, DMSO-$d_6$) δ 166.5, 162.4, 161.0, 139.6, 138.8, 137.2, 134.9, 128.2, 127.2, 127.1, 126.6, 120.4, 102.5, 96.6, 73.1, 42.3, 15.5, 9.5, 3.1; MS (ES+) m/z 395.2 (M+1).

Example 9.6

Synthesis of 5-(4-(3-(tert-Butyldimethylsilyloxy) propoxy)-2-oxopyridin-1(2H)-yl)-N-(3-fluorobenzyl)-3-methylthiophene-2-carboxamide

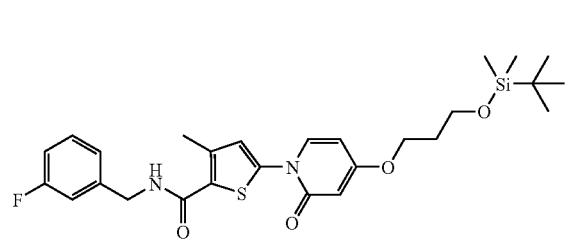 [SMILES: Cc1cc(-n2ccc(OCCCO[Si](C)(C)C(C)(C)C)cc2=O)sc1C(=O)NCc1cccc(F)c1]

Following the procedure as described in Example 9, making variations only as required to use (3-bromopropoxy)(tert-butyl)dimethylsilane in place of 2-cyclopropylethyl 4-methylbenzenesulfonate to react with N-(3-fluorobenzyl)-5-(4-hydroxy-2-oxopyridin-1(2H)-yl)-3-methylthiophene-2-carboxamide, the title compound was obtained as a yellowish viscous oil in quantitative yield: $^1$H NMR (300 MHz, CDCl$_3$) δ 7.54 (d, J=7.8 Hz, 1H), 7.35-7.27 (m, 1H), 7.12 (d, J=7.8 Hz, 1H), 7.05 (d, J=9.6 Hz, 1H), 7.00-6.94 (m, 1H), 6.85 (s, 1H), 6.19 (t, J=5.8 Hz, 1H), 6.07 (dd, J=7.8, 2.7 Hz, 1H), 5.98 (d, J=2.7 Hz, 1H), 4.59 (d, J=5.8 Hz, 2H), 4.07 (t, J=6.0 Hz, 2H), 3.77 (t, J=6.0 Hz, 2H), 3.52 (t, J=6.0 Hz, 2H), 2.54 (s, 3H), 0.88 (s, 9H), 0.04 (s, 6H); MS (ES+) m/z 531.5 (M+1).

Example 9.7

Synthesis of N-Benzyl-4-methyl-2-(2-oxo-4-β5-(trifluoromethyl)furan-2-yl)methoxy)pyridin-1(2H)-yl)thiazole-5-carboxamide

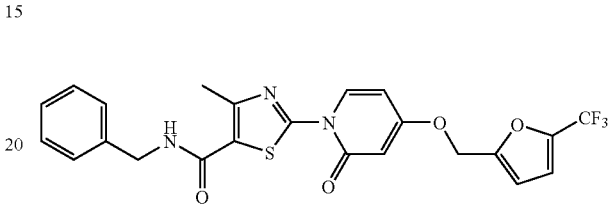

Following the procedure as described in Example 9, making variations only as required to use 2-(bromomethyl)-5-(trifluoromethyl)furan in place of 2-cyclopropylethyl 4-methylbenzenesulfonate to react with N-benzyl-2-(4-hydroxy-2-oxopyridin-1(2H)-yl)-4-methylthiazole-5-carboxamide, the title compound was obtained as a colorless solid in 16% yield: mp 214-216° C.; $^1$H NMR (300 MHz, DMSO-$d_6$) δ 8.71-8.68 (m, 1H), 7.38-7.26 (m, 5H), 6.81-6.79 (m, 1H), 6.57-6.56 (m, 1H), 6.22-6.06 (m, 3H), 5.00 (s, 2H), 4.59 (d, J=5.7 Hz, 2H), 2.68 (s, 3H); $^{13}$C NMR (75 MHz, DMSO-$d_6$) δ 166.8, 161.9, 161.5, 153.9, 152.6, 150.4, 139.9, 132.3, 128.8, 127.7, 127.2, 123.8, 114.6, 113.2, 107.5, 104.1, 97.6, 62.9, 62.4, 43.1, 17.5; MS (ES+) m/z 490.3 (M+1).

Example 9.8

Synthesis of N-Benzyl-4-methyl-2-(2-oxo-4-(4-(trifluoromethyl)benzyloxy)pyridin-1(2H)-yl)thiazole-5-carboxamide

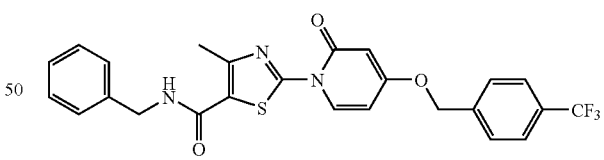

Following the procedure as described in Example 9, making variations only as required to use 4-trifluoromethylbenzyl bromide in place of 2-cyclopropylethyl 4-methylbenzenesulfonate to react with N-benzyl-2-(4-hydroxy-2-oxopyridin-1(2H)-yl)-4-methylthiazole-5-carboxamide, the title compound was obtained as a colorless solid in 21% yield: mp 278-280° C.; $^1$H NMR (300 MHz, DMSO-$d_6$) δ 8.78 (br s, 1H), 8.65-8.62 (m, 1H), 7.78-7.64 (m, 4H), 7.30-7.29 (m, 5H), 6.44-6.41 (m, 1H), 6.23 (d, J=2.7 Hz, 1H), 5.30 (s, 2H), 4.38 (d, J=6.0 Hz, 2H), 2.54 (s, 3H); $^{13}$C NMR (75 MHz, DMSO-$d_6$) δ 167.3, 161.9, 161.6, 153.9, 150.4, 140.7, 139.9, 132.3, 128.8, 128.7, 127.7, 127.2, 126.4, 126.0, 125.9, 123.8, 104.3, 97.7, 69.8, 43.1, 17.5; MS (ES+) m/z 500.3 (M+1).

Same as Example 1.24

Example 9.9

Synthesis of 2-(4-(4-(Difluoromethoxy)benzyloxy)-2-oxopyridin-1(2H)-yl)-N-(4-fluorobenzyl)-4-methylthiazole-5-carboxamide

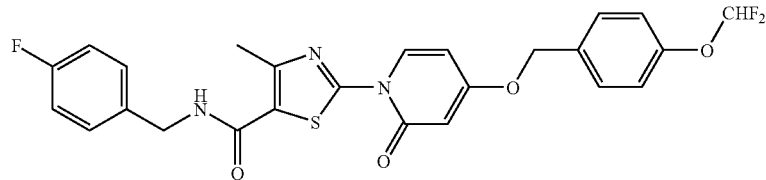 [SMILES: Cc1nc(-n2ccc(OCc3ccc(OC(F)F)cc3)cc2=O)sc1C(=O)NCc1ccc(F)cc1]

Following the procedure as described in Example 9, making variation only as required to use 4-(difluoromethoxy)benzyl bromide in place of 2-cyclopropylethyl 4-methylbenzenesulfonate to react with N-(4-fluorobenzyl)-2-(4-hydroxy-2-oxopyridin-1(2H)-yl)-4-methylthiazole-5-carboxamide, the title compound was obtained as a colorless solid in 25% yield: mp 242-244° C. (dichloromethane/methanol); $^1$H NMR (300 MHz, DMSO-$d_6$) δ 8.78 (t, J=5.8 Hz, 1H), 8.60 (dd, J=8.1, 3.0 Hz, 1H), 7.56-7.47 (m, 2H), 7.34-7.08 (m, 7H), 6.43-6.32 (m, 1H), 6.22 (s, 1H), 5.15 (s, 2H), 4.34 (d, J=5.8 Hz, 2H), 2.52 (s, 3H); $^{13}$C NMR (75 MHz, DMSO-$d_6$) δ 167.4, 163.2, 161.9, 160.0, 151.4, 150.4, 136.1, 133.7, 132.7, 130.5, 129.8, 123.6, 120.1, 119.2, 116.7, 115.6, 113.3, 104.3, 97.5, 70.1, 44.6, 17.5; MS (ES+) m/z 516.4 (M+1).

Example 9.10

Synthesis of N-Benzyl-2-(4-(cyclopentylmethoxy)-2-oxopyridin-1(2H)-yl)-4-methylthiazole-5-carboxamide

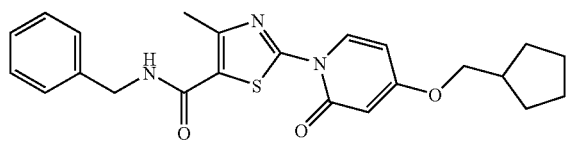 [SMILES: Cc1nc(-n2ccc(OCC3CCCC3)cc2=O)sc1C(=O)NCc1ccccc1]

Following the procedure as described in Example 9, making variation only as required to use cyclopentylmethyl 4-methylbenzenesulfonate in place of 2-cyclopropylethyl 4-methylbenzenesulfonate to react with N-benzyl-2-(4-hydroxy-2-oxopyridin-1(2H)-yl)-4-methylthiazole-5-carboxamide, the title compound was obtained as a colorless solid in 57% yield: mp 196-198° C. (methanol); $^1$H NMR (300 MHz, CDCl$_3$) δ 8.64 (d, J=8.1 Hz, 1H), 7.40-7.25 (m, 5H), 6.16 (d, J=8.1, 2.6 Hz, 1H), 6.09-6.05 (m, 1H), 5.94 (d, J=2.6 Hz, 1H), 4.58 (d, J=5.6 Hz, 2H), 3.83 (d, J=7.0 Hz, 2H), 2.68 (s, 3H) 2.41-2.27 (m, 1H), 1.87-1.77 (m, 4H), 1.66-1.58 (m, 4H); $^{13}$C NMR (75 MHz, CDCl$_3$) δ 167.9, 162.2, 162.1, 153.6, 152.2, 137.7, 131.3, 128.8, 127.9, 127.7, 122.1, 104.2, 96.6, 73.3, 44.1, 38.4, 29.3, 25.3, 17.3; MS (ES+) m/z 424.3 (M+1).

Example 9.11

Synthesis of N-(3,4-Difluorobenzyl)-2-(4-methoxy-2-oxopyridin-1(2H)-yl)-4-methylthiazole-5-carboxamide

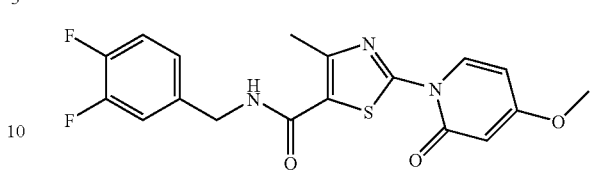

Following the procedure as described in Example 9, making variation only as required to use iodomethane in place of 2-cyclopropylethyl 4-methylbenzenesulfonate to react with N-(3,4-difluorobenzyl)-2-(4-hydroxy-2-oxopyridin-1(2H)-yl)-4-methylthiazole-5-carboxamide, the title compound was obtained as a colorless solid in 66% yield: mp 183-185° C. (ethyl acetate/hexanes); $^1$H NMR (300 MHz, CDCl$_3$) δ 8.65 (d, J=8.1 Hz, 1H), 7.18-7.05 (m, 3H), 6.20-6.15 (m, 2H), 5.97 (d, J=2.5 Hz, 1H), 4.53 (d, J=5.8 Hz, 2H), 3.82 (m, 3H), 2.68 (m, 3H); $^{13}$C NMR (75 MHz, CDCl$_3$) δ 168.4, 162.3, 162.1, 153.6, 152.7, 135.0, 131.4, 123.7, 121.8, 117.6, 117.4, 116.9, 116.7, 104.0, 96.2, 56.0, 43.0, 17.3; MS (ES+) m/z 392.2 (M+1).

Example 9.12

Synthesis of N-Benzyl-4-methyl-2-(2-oxo-4-((tetrahydrofuran-2-yl)methoxy)pyridin-1(2H)-yl)thiazole-5-carboxamide

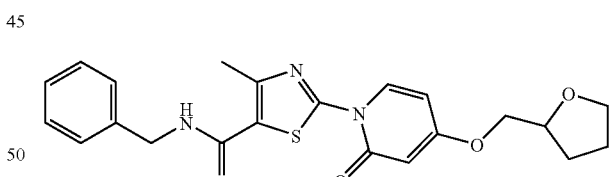

Following the procedure as described in Example 9, making variation only as required to use 2-(bromomethyl)tetrahydrofuran in place of 2-cyclopropylethyl 4-methylbenzenesulfonate to react with N-benzyl-2-(4-hydroxy-2-oxopyridin-1(2H)-yl)-4-methylthiazole-5-carboxamide, the title compound was obtained as a colorless solid in 42% yield: mp 181-183° C. (ethyl acetate/hexanes); $^1$H NMR (300 MHz, CDCl$_3$) δ 8.66-8.62 (m, 1H), 7.38-7.26 (m, 5H), 6.22-6.18 (m, 1H), 6.14-6.12 (m, 1H), 5.95-5.94 (m, 1H), 4.58-4.54 (m, 2H), 4.33-4.20 (m, 1H), 3.99-3.78 (m, 4H), 2.67 (s, 3H), 2.13-1.90 (m, 3H), 1.77-1.66 (m, 1H); MS (ES+) m/z 426.3 (M+1), 448.3 (M+23).

Example 10

Synthesis of N-Benzyl-2-(4-(4-chlorophenyl)-2-oxopyridin-1(2H)-yl)-4-methylthiazole-5-carboxamide

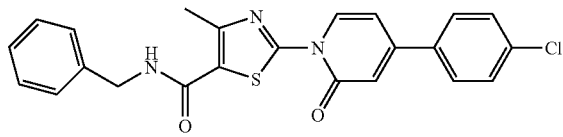 [SMILES: Cc1nc(-n2ccc(-c3ccc(Cl)cc3)cc2=O)sc1C(=O)NCc1ccccc1]

An oven-dried flask was charged with ethyl 1-(5-(benzylcarbamoyl)-4-methylthiazol-2-yl)-2-oxo-1,2-dihydropyridin-4-yl trifluoromethanesulfonate (0.10 g, 0.21 mmol), 4-chlorophenylboronic acid (0.036 g, 0.23 mmol), tetrakis(triphenylphosphine)palladium(0) (0.012 g, 0.01 mmol), potassium phosphate (0.067 g, 0.31 mmol) and potassium bromide (0.027 g, 0.23 mmol). The mixture was then purged with nitrogen, followed by the addition of anhydrous dioxane (7 mL). The reaction mixture was heated to reflux for 16 hours, then ethyl acetate (20 mL) was added and the mixture was washed with saturated ammonium chloride (10 mL), dried over anhydrous sodium sulfate and filtered. The filtrate was concentrated in vacuo. The brown residue was purified by column chromatography eluting with ethyl acetate/hexane (1/1) and then recrystallized from ether to afford the title compound as a colorless solid (0.090 g, 99%): mp 265-267° C. (ether); $^1$H NMR (300 MHz, DMSO-$d_6$) δ 8.89 (t, J=5.4 Hz, 1H), 8.81 (d, J=7.7 Hz, 1H), 7.91-7.88 (m, 2H), 7.64-7.58 (m, 2H), 7.35-7.23 (m, 5H), 7.15 (d, J=1.7 Hz, 1H), 7.05 (dd, J=7.7, 2.1 Hz, 1H), 4.44 (d, J=5.2 Hz, 2H), 2.62 (s, 3H); $^{13}$C NMR (75 MHz, DMSO-$d_6$) δ 161.8, 160.2, 153.6, 150.6, 150.0, 139.8, 135.7, 134.6, 131.7, 129.6, 129.3, 128.7, 127.7, 127.2, 124.5, 116.3, 107.5, 43.1, 17.5; MS (ES+) m/z 436.0 (M+1).

Example 11

Synthesis of 1-(5-(Benzylcarbamoyl)-4-methylthiazol-2-yl)-2-oxo-1,2-dihydropyridin-4-yl Trifluoromethanesulfonate

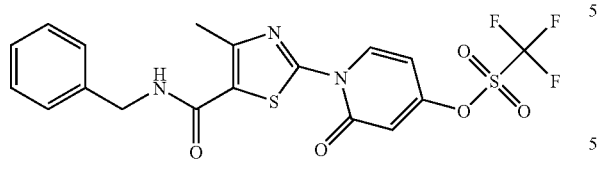

To a solution of N-benzyl-2-(4-hydroxy-2-oxopyridin-1(2H)-yl)-4-methylthiazole-5-carboxamide (1.00 g, 2.92 mmol) in anhydrous pyridine (20 mL) was added trifluoromethanesulfonic anhydride at −75° C. The mixture was stirred at −50° C. for 20 minutes followed by the addition of ethyl acetate (30 mL), and subsequently washed with water (2×5 mL). The organic layer was separated and concentrated in vacuo. The residue was subjected to column chromatography eluting with ethyl acetate/hexane (3/2) to afford the title compound as a yellow solid in 58% yield (0.81 g): $^1$H NMR (300 MHz, DMSO-$d_6$) δ 8.95 (d, J=8.1 Hz, 1H), 7.40-7.26 (m, 5H), 6.69 (d, J=2.6 Hz, 1H), 6.45 (dd, J=8.1, 2.6 Hz, 1H), 6.08 (t, J=5.6 Hz, 1H), 4.60 (d, J=5.6 Hz, 2H), 2.69 (s, 3H); MS (ES+) m/z 474.4 (M+1).

Example 12

Synthesis of Ethyl 4-Methyl-2-(2-oxo-4-phenylpyridin-1(2H)-yl)thiazole-5-carboxylate

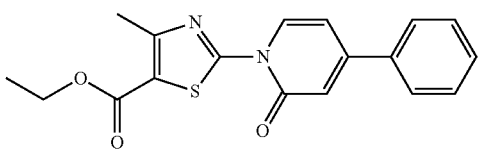 [SMILES: CCOC(=O)c1sc(-n2ccc(-c3ccccc3)cc2=O)nc1C]

To a solution of ethyl 2-bromo-4-methylthiazole-5-carboxylate (0.50 g, 2.00 mmol) in anhydrous N,N-dimethylformamide (10 mL) was added 4-phenylpyridin-2-ol (0.31 g, 1.80 mmol), copper(I) iodide (0.053 g, 0.28 mmol), 8-hydroxyquinoline (0.041 g, 0.28 mmol), and potassium carbonate (0.39 g, 2.80 mmol). The mixture was degassed and the flask was filled with nitrogen. The reaction mixture was heated at 100° C. for 6 hours and then diluted with ethyl acetate (25 mL), washed with 14% aqueous ammonium hydroxide (2×7 mL) and brine (7 mL). The organic layer was dried over anhydrous sodium sulfate, filtered concentrated in vacuo to afford as a yellowish solid (0.45 g, 66%): $^1$H NMR (300 MHz, DMSO-$d_6$) δ 8.83-8.75 (m, 1H), 7.88-7.81 (m, 2H), 7.60-7.50 (m, 3H), 7.14-7.03 (m, 2H), 4.26 (q, J=7.0 Hz, 2H), 2.64 (s, 3H), 1.28 (t, J=7.0 Hz, 3H); MS (ES+) m/z 341.6 (M+1).

Example 12.1

Synthesis of Ethyl 2-(4-(Benzyloxy)-2-oxopyridin-1(2H)-yl)-4-methylthiazole-5-carboxylate

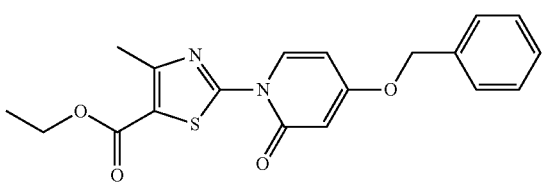

Following the procedure as described in Example 12, making variations only as required to use 4-(benzyloxy)pyridin-2(1H)-one in place of 4-phenylpyridin-2-ol to react with ethyl 2-bromo-4-methylthiazole-5-carboxylate, the title compound was obtained as a yellow solid in 80% yield: $^1$H NMR (300 MHz, CDCl$_3$) δ 8.65 (d, J=7.9 Hz, 1H), 7.42-7.26 (m, 5H), 6.18 (d, J=7.9 Hz, 1H), 6.07 (s, 1H), 5.01 (s, 2H), 4.28 (q, J=7.1 Hz, 1H), 2.65 (s, 3H), 1.32 (t, J=7.1 Hz, 3H); MS (ES+) m/z 371.1 (M+1).

Example 12.2

Synthesis of Ethyl 2-(4-(benzyloxy)-2-oxopyridin-1(2H)-yl)-4-methyl-1H-imidazole-5-carboxylate

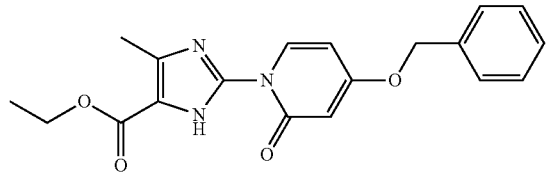 [SMILES: CCOC(=O)c1[nH]c(-n2ccc(OCc3ccccc3)cc2=O)nc1C]

Following the procedure as described in Example 12, making variations only as required to use 4-(benzyloxy)pyridin-2(1H)-one in place of 4-phenylpyridin-2-ol to react with ethyl 2-bromo-4-methyl-1H-imidazole-5-carboxylate in place of ethyl 2-bromo-4-methylthiazole-5-carboxylate at 130° C. for 64 hours, the title compound was obtained as a colorless solid in 26% yield: mp 135-136° C.; $^1$H NMR (300 MHz, CDCl$_3$) δ 12.01 (s, 1H), 8.60-8.50 (m, 1H), 7.44-7.36 (m, 5H), 6.21 (dd, J=8.0, 2.6 Hz, 1H), 6.04 (d, J=2.6 Hz, 1H), 5.06 (s, 2H), 4.44-4.29 (m, 2H), 2.59-2.51 (m, 3H), 1.44-1.34 (m, 3H); MS (ES+) m/z 354.2 (M+1).

Example 12.3

Synthesis of Ethyl 2-(4-(Benzyloxy)-2-oxopyridin-1(2H)-yl)-1,4-dimethyl-1H-imidazole-5-carboxylate

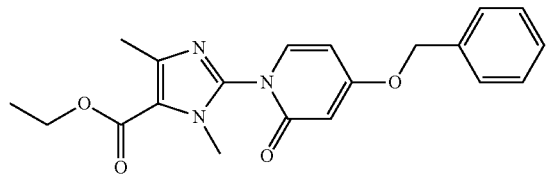 [SMILES: CCOC(=O)c1c(C)nc(-n2ccc(OCc3ccccc3)cc2=O)n1C]

Following the procedure as described in Example 12, making variations only as required to use 4-(benzyloxy)pyridin-2(1H)-one in place of 4-phenylpyridin-2-ol to react with ethyl 2-bromo-1,4-dimethyl-1H-imidazole-5-carboxylate in place of ethyl 2-bromo-4-methylthiazole-5-carboxylate at 125° C. for 64 hours, the title compound was obtained as a colorless solid in 24% yield: $^1$H NMR (300 MHz, CDCl$_3$) δ 7.44-7.36 (m, 5H), 7.22 (d, J=7.7 Hz, 1H), 6.09 (dd, J=7.7, 2.5 Hz, 1H) 5.98 (d, J=2.5 Hz, 1H), 5.04 (s, 2H), 4.35 (q, J=7.1 Hz, 2H), 3.69 (s, 3H), 2.49 (s, 3H), 1.38 (t, J=7.1 Hz, 3H); MS (ES+) m/z 368.2 (M+1).

Example 12.4

Synthesis of Ethyl 2-(4-(Benzyloxy)-2-oxopyridin-1(2H)-yl)-1,5-dimethyl-1H-imidazole-4-carboxylate Not Covered by Formula (I)

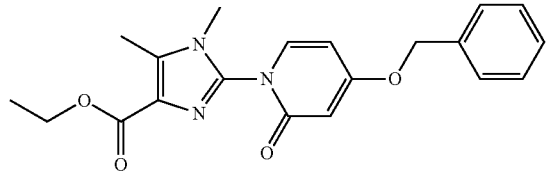 [SMILES: CCOC(=O)c1nc(-n2ccc(OCc3ccccc3)cc2=O)n(C)c1C]

Following the procedure as described in Example 12, making variations only as required to use 4-(benzyloxy)pyridin-2(1H)-one in place of 4-phenylpyridin-2-ol to react with ethyl 2-bromo-1,5-dimethyl-1H-imidazole-4-carboxylate in place of ethyl 2-bromo-4-methylthiazole-5-carboxylate at 125° C. for 28 hours, the title compound was obtained as a colorless solid in 30% yield: $^1$H NMR (300 MHz, CDCl$_3$) δ 7.43-7.38 (m, 5H), 7.31 (d, J=7.7 Hz, 1H), 6.07 (dd, J=7.7, 2.5 Hz, 1H) 5.96 (d, J=2.5 Hz, 1H), 5.04 (s, 2H), 4.37 (q, J=6.9 Hz, 2H), 3.42 (s, 3H), 2.58 (s, 3H), 1.38 (t, J=7.1 Hz, 3H); MS (ES+) m/z 368.3 (M+1).

Example 13

Synthesis of 4-Methyl-2-(2-oxo-4-phenylpyridin-1(2H)-yl)thiazole-5-carboxylic Acid

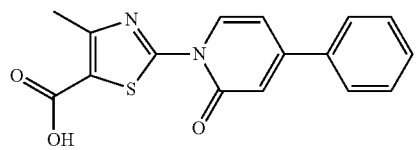 [SMILES: Cc1nc(-n2ccc(-c3ccccc3)cc2=O)sc1C(=O)O]

To a solution of ethyl 4-methyl-2-(2-oxo-4-phenylpyridin-1(2H)-yl)thiazole-5-carboxylate (0.25 g, 0.74 mmol) in a mixture of tetrahydrofuran (4 mL) and water (4 mL) was added lithium hydroxide (0.14 g, 3.68 mmol). The reaction mixture was heated at 50° C. for 4 hours, then cooled to ambient temperature and acidified to pH 6 with acetic acid. The solid obtained was collected by filtration, washed with water and dried in air. The title compound was obtained as a yellowish solid (0.20 g, 87%): MS (ES+) m/z 313.5 (M+1).

Example 13.1

Synthesis of 2-(4-(Benzyloxy)-2-oxopyridin-1(2H)-yl)-4-methylthiazole-5-carboxylic acid

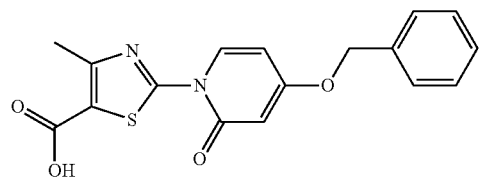 [SMILES: Cc1nc(-n2ccc(OCc3ccccc3)cc2=O)sc1C(=O)O]

Following the procedure as described in Example 13, making variations only as required to use ethyl 2-(4-(benzyloxy)-2-oxopyridin-1(2H)-yl)-4-methylthiazole-5-carboxylate in place of ethyl 4-methyl-2-(2-oxo-4-phenylpyridin-1(2H)-yl)thiazole-5-carboxylate, the title compound was obtained as a yellowish solid in 72% yield: MS (ES+) m/z 343.2 (M+1).

Example 13.2

Synthesis of 2-(4-(Cyclopropylmethoxy)-2-oxopyridin-1(2H)-yl)-4-methylthiazole-5-carboxylic Acid

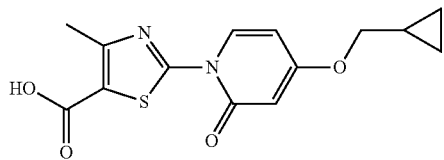 [SMILES: Cc1nc(-n2ccc(OCC3CC3)cc2=O)sc1C(=O)O]

Following the procedure as described in Example 13, making variations only as required to use ethyl 2-(4-(cyclopropylmethoxy)-2-oxopyridin-1(2H)-yl)-4-methylthiazole-5-carboxylate in place of ethyl 4-methyl-2-(2-oxo-4-phenylpyridin-1(2H)-yl)thiazole-5-carboxylate, the title compound was obtained as a yellowish solid in 73% yield: MS (ES+) m/z 307.4 (M+1).

Example 13.3

Synthesis of 2-(4-(2-Cyclopropylethoxy)-2-oxopyridin-1(2H)-yl)-4-methylthiazole-5-carboxylic Acid

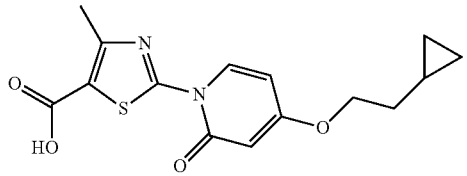 [SMILES: Cc1nc(-n2ccc(OCCC3CC3)cc2=O)sc1C(=O)O]

Following the procedure as described in Preparation 13, making variations only as required to use ethyl 2-(4-(2-cyclopropylethoxy)-2-oxopyridin-1(2H)-yl)-4-methylthiazole-5-carboxylate in place of ethyl 4-methyl-2-(2-oxo-4-phenylpyridin-1(2H)-yl)thiazole-5-carboxylate, the title compound was obtained as a pale yellow solid in 85% yield: MS (ES+) m/z: 321.4 (M+1).

Example 13.4

Synthesis of 2-(4-Methoxy-2-oxopyridin-1(2H)-yl)-4-methylthiazole-5-carboxylic Acid

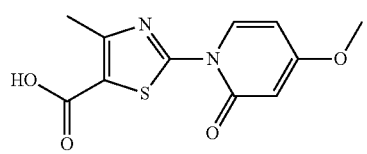

Following the procedure as described in Example 13, making variations only as required to use ethyl 2-(4-methoxy-2-oxopyridin-1(2H)-yl)-4-methylthiazole-5-carboxylate in place of ethyl 4-methyl-2-(2-oxo-4-phenylpyridin-1(2H)-yl) thiazole-5-carboxylate, the title compound was obtained as a yellowish solid in 80% yield: MS (ES+) m/z 267.3 (M+1).

Example 13.5

Synthesis of 2-(4-Hydroxy-2-oxopyridin-1(2H)-yl)-4-methylthiazole-5-carboxylic Acid

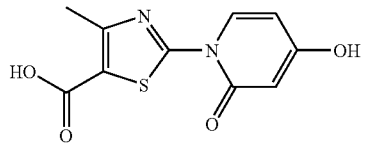 [SMILES: Cc1nc(-n2ccc(O)cc2=O)sc1C(=O)O]

Following the procedure as described in Example 13, making variations only as required to use ethyl 2-(4-hydroxy-2-oxopyridin-1(2H)-yl)-4-methylthiazole-5-carboxylate in place of ethyl 4-methyl-2-(2-oxo-4-phenylpyridin-1(2H)-yl) thiazole-5-carboxylate, the title compound was obtained as a colorless solid in 92% yield: MS (ES+) m/z 253.2 (M+1).

Example 13.6

Synthesis of 4-Methyl-2-(2-oxo-4-β5-(trifluoromethyl)furan-2-yl)methoxy)pyridin-1(2H)-yl)thiazole-5-carboxylic acid

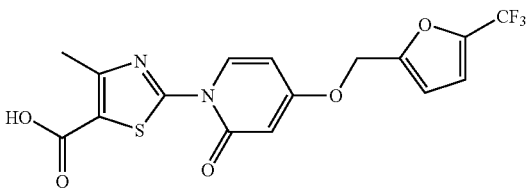 [SMILES: Cc1nc(-n2ccc(OCc3ccc(C(F)(F)F)o3)cc2=O)sc1C(=O)O]

Following the procedure as described in Example 13, making variations only as required to use ethyl 4-methyl-2-(2-oxo-4-(5-(trifluoromethyl)furan-2-yl)methoxy)pyridin-1 (2H)-yl)thiazole-5-carboxylate in place of ethyl 4-methyl-2-(2-oxo-4-phenylpyridin-1(2H)-yl)thiazole-5-carboxylate, the title compound was obtained as a colorless solid in 75% yield: mp 261-263° C. (water/acetone); $^1$H NMR (300 MHz, DMSO-$d_6$) δ 13.24 (br s, 1H), 8.61 (d, J=8.1 Hz, 1H), 7.25-7.23 (m, 1H), 6.90 (d, J=3.2 Hz, 1H), 6.39 (dd, J=8.1, 2.7 Hz, 1H), 6.32 (d, J=2.7 Hz, 1H), 5.25 (s, 2H), 2.58 (s, 3H); $^{13}$C NMR (75 MHz, DMSO-$d_6$) δ 166.8, 164.0, 161.6, 155.8, 154.4, 152.6, 141.3, 132.1, 121.1, 117.6, 114.5, 113.1, 104.1, 97.6, 62.4, 17.4; MS (ES+) m/z 401.1 (M+1).

Example 13.7

Synthesis of 2-(4-(4-Fluorobenzyloxy)-2-oxopyridin-1(2H)-yl)-4-methylthiazole-5-carboxylic acid

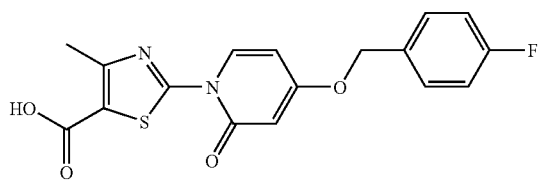 [SMILES: Cc1nc(-n2ccc(OCc3ccc(F)cc3)cc2=O)sc1C(=O)O]

Following the procedure as described in Example 13, making variations only as required to use ethyl 2-(4-(4-fluorobenzyloxy)-2-oxopyridin-1(2H)-yl)-4-methylthiazole-5-carboxylate in place of ethyl 4-methyl-2-(2-oxo-4-phenylpyridin-1(2H)-yl)thiazole-5-carboxylate, the title compound was obtained as a colorless solid in 79% yield: mp>300° C. (water/acetone); $^1$H NMR (300 MHz, DMSO-$d_6$) δ 8.60 (d, J=8.1 Hz, 1H), 7.52-7.47 (m, 2H), 7.27-7.16 (m, 2H), 6.90 (d, J=3.2 Hz, 1H), 6.37 (dd, J=8.1, 2.7 Hz, 1H), 6.21 (d, J=2.6 Hz, 1H), 5.14 (s, 2H), 2.57 (s, 3H); $^{13}$C NMR (75 MHz, DMSO-$d_6$) δ 167.4, 164.1, 161.7, 160.9, 155.9, 154.4, 132.0, 131.9, 130.9, 120.8, 116.0, 115.7, 104.1, 97.5, 70.1, 17.4; MS (ES+) m/z 361.3 (M+1).

Example 13.8

Synthesis of 5-(4-(Benzyloxy)-2-oxopyridin-1(2H)-yl)-3-methylthiophene-2-carboxylic acid

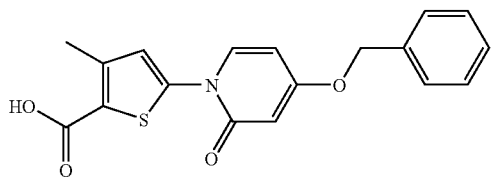 [SMILES: Cc1cc(-n2ccc(OCc3ccccc3)cc2=O)sc1C(=O)O]

Following the procedure as described in Example 13, making variations only as required to use ethyl 5-(4-(benzyloxy)-2-oxopyridin-1(2H)-yl)-3-methylthiophene-2-carboxylate in place of ethyl 4-methyl-2-(2-oxo-4-phenylpyridin-1(2H)-yl)thiazole-5-carboxylate, the title compound was obtained as a colorless solid in 92% yield: $^1$H NMR (300 MHz, DMSO-$d_6$) δ 12.82 (br s, 1H), 8.20 (d, J=8.0 Hz, 1H), 7.50-7.32 (m, 6H), 6.30 (dd, J=8.0, 2.6 Hz, 1H), 6.14 (d, J=2.6 Hz, 1H), 5.17 (s, 2H), 2.46 (s, 3H); MS (ES+) m/z 342.2 (M+1).

Example 14

Synthesis of Ethyl 2-(4-Hydroxy-2-oxopyridin-1(2H)-yl)-4-methylthiazole-5-carboxylate

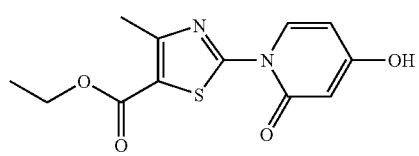

A mixture of ethyl 2-(4-(benzyloxy)-2-oxopyridin-1(2H)-yl)-4-methylthiazole-5-carboxylate (7.00 g, 18.0 mmol) and 20 wt. % palladium on activated carbon (3 g) in anhydrous tetrahydrofuran (300 mL) was stirred under an atmosphere of hydrogen for 2 hours. The mixture was filtered through celite and the filtrate was concentrated in vacuo. The residue was recrystallized from ethyl acetate to afford the title compound as a colorless solid (4.00 g, 80%): mp 270-273° C. (ethyl acetate); $^1$H NMR (300 MHz, DMSO-$d_6$) δ 11.57 (s, 1H), 8.58 (d, J=8.0 Hz, 1H), 6.27 (dd, J=8.0, 2.5 Hz, 1H), 5.81 (d, J=2.5 Hz, 1H), 4.24 (q, J=7.1 Hz, 2H), 2.58 (s, 3H), 1.26 (t, J=7.1 Hz, 3H); $^{13}$C NMR (75 MHz, DMSO-$d_6$) δ 168.0, 162.5, 161.7, 156.5, 155.3, 132.4, 119.0, 104.7, 97.9, 61.2, 17.6, 14.6; MS (ES+) m/z 281.0 (M+1).

Example 15

Synthesis of Ethyl 2-(4-(Cyclopropylmethoxy)-2-oxopyridin-1(2H)-yl)-4-methylthiazole-5-carboxylate

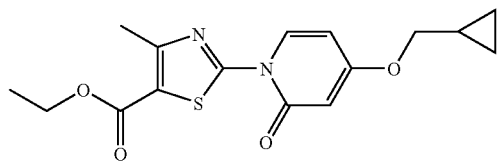 [SMILES: CCOC(=O)c1sc(-n2ccc(OCC3CC3)cc2=O)nc1C]

To a stirred solution of ethyl 2-(4-hydroxy-2-oxopyridin-1(2H)-yl)-4-methylthiazole-5-carboxylate (1.00 g, 3.56 mmol) in N,N-dimethylformamide (10 mL) at 0° C. was added sodium hydride (0.14 g, 5.70 mmol). The reaction mixture was stirred at 0° C. for 30 minutes, then (bromomethyl)cyclopropane (0.58 g, 4.28 mmol) was added. The reaction mixture was stirred at ambient temperature for 16 hours. The solvent was removed at high vacuum and the residue was diluted with dichloromethane (30 mL), washed with brine (25 mL), dried over sodium sulfate and filtered. The filtrate was concentrated in vacuo. The residue was purified by column chromatography eluting with ethyl acetate/hexane (1/1) to afford the title compound as a colorless solid (1.15 g, 97%): mp 180-183° C. (hexane/ethyl acetate); $^1$H NMR (300 MHz, CDCl$_3$) δ 8.68-8.65 (m, 1H), 6.19-6.16 (m, 1H), 5.93 (d, J=2.6 Hz, 1H), 4.31 (q, J=7.1 Hz, 2H), 3.81 (d, J=7.1 Hz, 2H), 2.68 (s, 3H), 1.35 (t, J=7.1 Hz, 3H), 1.31-1.19 (m, 1H), 0.70-0.64 (m, 2H), 0.38-0.33 (m, 2H); $^{13}$C NMR (75 MHz, CDCl$_3$) δ 167.6, 162.9, 162.2, 156.6, 155.6, 131.3, 119.6, 104.5, 96.7, 60.9, 17.3, 14.3, 9.8, 9.5, 3.3; MS (ES+) m/z 335.1 (M+1).

Example 15.1

Synthesis of Ethyl 2-(4-Methoxy-2-oxopyridin-1(2H)-yl)-4-methylthiazole-5-carboxylate

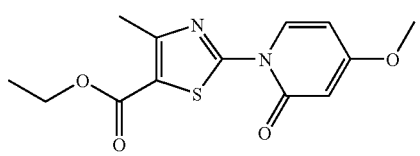 [SMILES: CCOC(=O)c1sc(-n2ccc(OC)cc2=O)nc1C]

Following the procedure as described in Example 15, making variations only as required to use methyl iodide in place of (bromomethyl)cyclopropane to react with ethyl 2-(4-hydroxy-2-oxopyridin-1(2H)-yl)-4-methylthiazole-5-carboxylate, the title compound was obtained as a yellowish solid in 54% yield: mp 163-165° C. (hexane/ethyl acetate); $^1$H NMR (300 MHz, CDCl$_3$) δ 8.67 (d, J=8.1 Hz, 1H), 6.16 (dd, J=8.1, 2.7 Hz, 1H), 6.00 (d, J=2.7 Hz, 1H), 4.32 (q, J=7.1 Hz, 2H), 3.83 (s, 3H), 2.68 (s, 3H), 1.36 (t, J=7.1 Hz, 3H); $^{13}$C NMR (75 MHz, CDCl₃) δ 168.3, 162.9, 162.2, 156.6, 155.7, 131.3, 119.7, 103.8, 96.3, 60.9, 56.0, 17.3, 14.3; MS (ES+) m/z 295.2 (M+1).

Example 15.2

Synthesis of Ethyl 2-(4-(2-Cyclopropylethoxy)-2-oxopyridin-1(2H)-yl)-4-methylthiazole-5-carboxylate

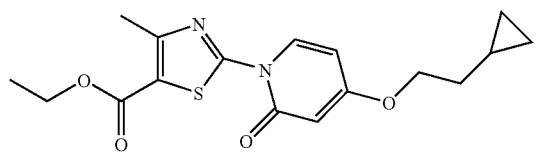 [SMILES: CCOC(=O)c1sc(-n2ccc(OCCC3CC3)cc2=O)nc1C]

Following the procedure as described in Example 15, making variations only as required to use 2-cyclopropylethyl-4-methylbenzenesulfonate in place of (bromomethyl)cyclopropane to react with ethyl 2-(4-hydroxy-2-oxopyridin-1(2H)-yl)-4-methylthiazole-5-carboxylate, the title compound was obtained as a colorless solid in 35% yield: mp 188-190° C. (hexane/ethyl acetate); ¹H NMR (300 MHz, CDCl₃) δ 8.67 (dd, J=8.1, 1.1 Hz, 1H), 6.17-6.13 (m, 1H), 6.00-5.99 (m, 1H), 4.35-4.27 (m, 2H), 4.04 (t, J=6.6 Hz, 2H), 2.68 (s, 3H), 1.68 (q, J=6.6 Hz, 2H), 1.35 (dt, J=7.1, 1.3 Hz, 3H), 0.90-0.68 (m, 1H), 0.52-0.44 (m, 2H), 0.14-0.09 (m, 2H); ¹³C NMR (75 MHz, CDCl₃) δ 167.8, 162.9, 162.2, 156.6, 155.6, 131.3, 119.7, 104.1, 96.7, 69.1, 60.9, 33.6, 17.3, 14.3, 7.5, 4.2; MS (ES+) m/z 349.2 (M+1).

Example 16

Synthesis of 2-(4-(Benzyloxy)-2-oxopyridin-1(2H)-yl)-4-methyl-1H-imidazole-5-carboxylic Acid

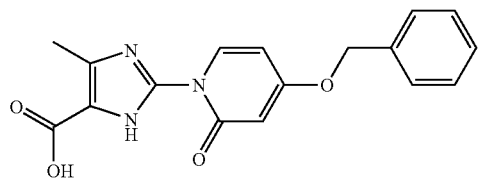 [SMILES: Cc1nc(-n2ccc(OCc3ccccc3)cc2=O)[nH]c1C(=O)O]

A suspension of ethyl 2-(4-(benzyloxy)-2-oxopyridin-1(2H)-yl)-4-methyl-1H-imidazole-5-carboxylate (0.10 g, 0.28 mmol) in 1 N aqueous sodium hydroxide (2 mL) was stirred at 45° C. for 16 h, and then at 65° C. for 5 h. The reaction mixture was cooled to 0° C. then acidified with 10% aqueous hydrochloric acid to pH ~2. The precipitate was filtered, washed with water, and then with acetone into a separate flask. The acetone filtrate was concentrated in vacuo and co-concentrated with methanol to dryness (×2). The residue was combined with the solid to afford the title compound (0.060 g, 65%): MS (ES−) m/z 324.2 (M−1).

Example 16.1

Synthesis of 2-(4-(Benzyloxy)-2-oxopyridin-1(2H)-yl)-1,4-dimethyl-1H-imidazole-5-carboxylic Acid

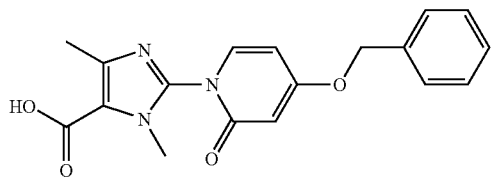 [SMILES: Cc1nc(-n2ccc(OCc3ccccc3)cc2=O)n(C)c1C(=O)O]

Following the procedure are described in Example 16, making variations only as required to use ethyl 2-(4-(benzyloxy)-2-oxopyridin-1(2H)-yl)-1,4-dimethyl-1H-imidazole-5-carboxylate in place of ethyl 2-(4-(benzyloxy)-2-oxopyridin-1(2H)-yl)-4-methyl-1H-imidazole-5-carboxylate, the title compound was obtained as a colorless solid in 97% yield: ¹H NMR (300 MHz, DMSO-d₆) δ 13.03 (br s, 1H), 7.54 (dd, J=7.8, 1.4 Hz, 1H), 7.51-7.37 (m, 5H), 6.18 (d, J=7.8 Hz, 1H), 6.03 (s, 1H), 5.16 (s, 2H), 3.50 (s, 3H), 2.38 (s, 3H); MS (ES+) m/z 340.2 (M+1).

Example 16.2

Synthesis of 2-(4-(Benzyloxy)-2-oxopyridin-1(2H)-yl)-1,5-dimethyl-2,3-dihydro-1H-imidazole-4-carboxylic Acid

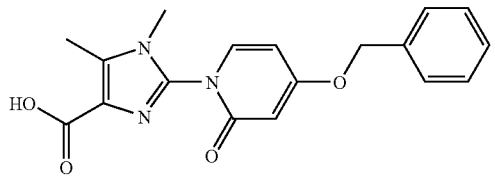 [SMILES: Cc1c(C(=O)O)nc(-n2ccc(OCc3ccccc3)cc2=O)n1C]

Following the procedure as described in Example 16, making variations only as required to use ethyl 2-(4-(benzyloxy)-2-oxopyridin-1(2H)-yl)-1,5-dimethyl-1H-imidazole-4-carboxylate in place of ethyl 2-(4-(benzyloxy)-2-oxopyridin-1(2H)-yl)-4-methyl-1H-imidazole-5-carboxylate, the title compound was obtained as a colorless solid in 86% of yield: ¹H NMR (300 MHz, DMSO-d₆) δ 12.24 (br s, 1H), 7.56-7.34 (m, 6H), 6.18 (d, J=7.3 Hz, 1H), 6.04 (s, 1H), 5.16 (s, 2H), 3.30 (s, 3H), 3.17 (s, J=4.7 Hz, 3H); MS (ES+) m/z 340.2 (M+1).

Example 17

Synthesis of ethyl 4-Methyl-2-(2-oxo-4-β5-(trifluoromethyl)furan-2-yl)methoxy)pyridin-1(2H)-yl)thiazole-5-carboxylate

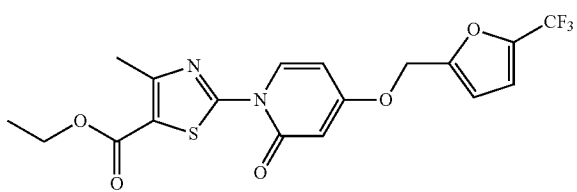 [SMILES: CCOC(=O)c1sc(-n2ccc(OCc3ccc(C(F)(F)F)o3)cc2=O)nc1C]

To a stirred solution of ethyl 2-(4-hydroxy-2-oxopyridin-1(2H)-yl)-4-methylthiazole-5-carboxylate (1.00 g, 3.56 mmol) in N,N-dimethylformamide (20 mL) at 0° C. was added sodium hydride (0.15 g, 6.42 mmol). The mixture was stirred at 0° C. for 30 minutes, followed by the addition of 2-(bromomethyl)-5-(trifluoromethyl)furan (1.06 g, 4.63 mmol). The reaction mixture was stirred at ambient temperature for 16 hours. The solvent was removed in vacuo and the residue was diluted with dichloromethane (250 mL), washed with brine (100 mL), dried over sodium sulfate, filtered and concentrated in vacuo. The residue was recrystallized in ethyl acetate and hexane to afford the title compound as a colorless solid in 68% yield (1.04 g): mp 196-198° C. (ethyl acetate/hexanes); $^1$H NMR (300 MHz, CDCl$_3$) δ 8.72-8.70 (m, 1H), 6.80-6.79 (m, 1H), 6.37 (d, J=3.2 Hz, 1H), 6.21-6.17 (m, 1H), 6.09 (d, J=2.5 Hz, 1H), 5.02 (s, 2H), 4.32 (q, J=7.1 Hz, 2H), 2.68 (s, 3H), 1.36 (t, J=7.1 Hz, 3H); $^{13}$C NMR (75 MHz, CDCl$_3$) δ 166.5, 162.8, 161.8, 156.3, 155.7, 150.6, 143.1, 131.8, 120.4, 119.9, 112.4, 111.7, 103.6, 97.2, 62.1, 61.0, 17.3, 14.3; MS (ES+) m/z 429.2 (M+1).

Example 17.1

Synthesis of Ethyl 2-(4-(4-Fluorobenzyloxy)-2-oxopyridin-1(2H)-yl)-4-methylthiazole-5-carboxylate

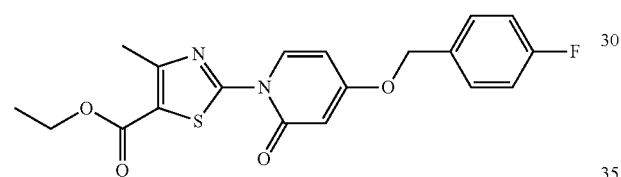

Following the procedure as described in Example 17, making variations only as required to use ethyl 1-(bromomethyl)-4-fluorobenzene in place of 2-(bromomethyl)-5-(trifluoromethyl)furan to react with ethyl 2-(4-hydroxy-2-oxopyridin-1(2H)-yl)-4-methylthiazole-5-carboxylate, the title compound was obtained as a colorless solid in 70% yield: mp 214-217° C. (ethyl acetate/hexanes); $^1$H NMR (300 MHz, CDCl$_3$) δ 8.70 (d, J=8.1 Hz, 1H), 7.42-7.34 (m, 2H), 7.12-7.04 (m, 2H), 6.20 (dd, J=8.1, 2.7 Hz, 1H), 6.07 (d, J=2.7 Hz, 1H), 5.01 (s, 2H), 4.32 (q, J=7.1 Hz, 2H), 2.68 (s, 3H), 1.36 (t, J=7.1 Hz, 3H); $^{13}$C NMR (75 MHz, CDCl$_3$) δ 167.1, 164.5, 162.8, 161.2, 156.5, 155.6, 131.5, 130.4, 129.8, 119.8, 115.9, 103.9, 97.4, 70.1, 61.9, 17.3, 14.3; MS (ES+) m/z 389.2 (M+1).

Example 18

Synthesis of N-Benzyl-4-methyl-2-(2-oxo-4-phenoxypyridin-1(2H)-yl)thiazole-5-carboxamide

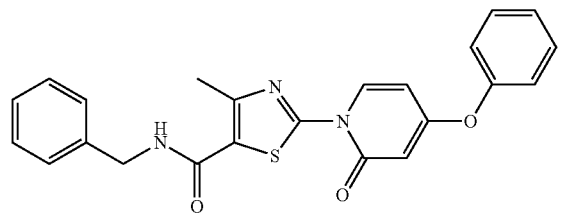 [SMILES: Cc1nc(-n2ccc(Oc3ccccc3)cc2=O)sc1C(=O)NCc1ccccc1]

To a solution of N-benzyl-2-(4-hydroxy-2-oxopyridin-1(2H)-yl)-4-methylthiazole-5-carboxamide (0.20 g, 0.58 mmol) and 2-(trimethylsilyl)phenyl trifluoromethanesulfonate (0.19 g, 0.64 mmol) in anhydrous acetonitrile (10 mL) was added cesium fluoride (0.22 g, 1.46 mmol). The reaction mixture was heated at 60° C. for 16 hours, followed by the addition of ethyl acetate (30 mL). The mixture was washed with saturated ammonium chloride (10 mL), dried over anhydrous sodium sulfate, filtered and the filtrate was concentrated in vacuo. The residue was purified by column chromatography eluted with ethyl acetate/hexane (1/1) and further purified by recrystallization in ether to afford the title compound as a colorless solid in 14% yield (0.032 g): mp 67-70° C. (ether); $^1$H NMR (300 MHz, CDCl$_3$) δ 8.76 (d, J=8.1 Hz, 1H), 7.45-7.25 (m, 8H), 7.11-7.08 (m, 2H), 6.35 (dd, J=8.1, 2.7 Hz, 1H), 6.05 (t, J=5.6 Hz, 1H), 5.81 (d, J=2.6 Hz, 1H), 4.58 (d, J=5.6 Hz, 2H), 2.69 (s, 3H); $^{13}$C NMR (75 MHz, CDCl$_3$) δ 167.8, 162.1, 161.8, 153.3, 152.8, 152.1, 137.7, 132.2, 130.3, 128.8, 127.9, 127.7, 126.4, 122.5, 121.1, 103.4, 100.2, 44.1, 17.3; MS (ES+) m/z 418.2 (M+1).

Example 19

Synthesis of N-benzyl-4-methyl-2-(2-oxo-4-phenethylpyridine-1(2H)-yl)thiazole-5-carboxamide

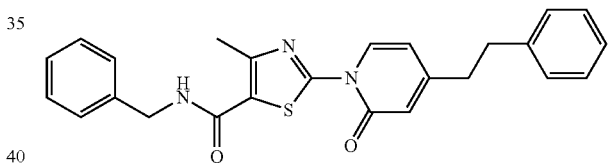

To an oven-dried sealed tube under nitrogen atmosphere was added 145-(benzylcarbamoyl)-4-methylthiazol-2-yl)-2-oxo-1,2-dihydropyridin-4-yl trifluoromethanesulfonate (0.20 g, 0.42 mmol), phenethylboronic acid (0.069 g, 0.46 mmol), 1,1'-bis(diphenylphosphino)ferrocene]dichloropalladium(II) (0.068 g, 0.084 mmol) and potassium carbonate (0.18 g, 1.26 mmol), followed by the addition of tetrahydrofuran (10 mL) and water (1 mL). The reaction mixture was heated at reflux for 22 hours, and cooled to ambient temperature. Ethyl acetate (20 mL) was added and the mixture was washed with saturated ammonium chloride (10 mL), dried over anhydrous sodium sulfate and filtered. The filtrate was concentrated in vacuo. The brown residue was purified by column chromatography eluted with ethyl acetate/hexane (1/1) to afford the title compound as a colorless solid in 33% yield (0.060 g): mp 149-150° C. (ethyl acetate/hexanes); $^1$H NMR (300 MHz, CDCl$_3$) δ 8.66 (d, J=7.5 Hz, 1H), 7.34-7.25 (m, 7H), 7.21-7.14 (m, 3H), 6.49 (s, 1H), 6.25 (dd, J=7.5, 1.8 Hz, 1H), 6.11 (t, J=5.6 Hz, 1H), 4.59 (d, J=5.6 Hz, 2H), 2.95-2.89 (m, 2H), 2.84-2.76 (m, 2H), 2.69 (s, 3H); $^{13}$C NMR (75 MHz, CDCl$_3$) δ 162.1, 160.5, 155.2, 153.3, 152.3, 140.0, 137.7, 130.2, 128.8, 128.6, 128.3, 127.9 127.7, 126.4, 122.8, 118.6, 109.7, 44.1, 37.0, 35.0, 17.3; MS (ES+) m/z 430.3 (M+1).

Example 19.1

Synthesis of N-Benzyl-2-(4-cyclopropyl-2-oxopyridin-1(2H)-yl)-4-methylthiazole-5-carboxamide

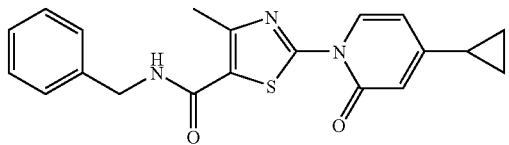 [SMILES: Cc1nc(-n2ccc(C3CC3)cc2=O)sc1C(=O)NCc1ccccc1]

Following the procedure as described in Example 19, making variations only as required to use cyclopropylboronic acid in place of phenethylboronic acid to react with -(5-(benzylcarbamoyl)-4-methylthiazol-2-yl)-2-oxo-1,2-dihydropyridin-4-yl trifluoromethanesulfonate, the title compound was obtained as a colorless solid in 54% yield: mp 149-151° C. (ethyl acetate/hexanes); $^1$H NMR (300 MHz, CDCl$_3$) δ 8.63 (d, J=7.6 Hz, 1H), 7.39-7.25 (m, 5H), 6.39 (d, J=1.5 Hz, 1H), 6.10-6.05 (m, 2H), 4.58 (d, J=5.6 Hz, 2H), 2.69 (s, 3H), 1.81-1.72 (m, 1H), 1.14-1.07 (m, 2H), 0.86-0.81 (m, 2H); $^{13}$C NMR (75 MHz, CDCl$_3$) δ 162.2, 160.3, 158.8, 153.4, 152.3, 137.7, 130.3, 128.8, 127.9, 127.6, 127.7, 114.7, 106.6, 44.1, 17.3, 15.4, 10.4; MS (ES+) m/z 366.1 (M+1).

Example 20

Synthesis of N-Benzyl-4-methyl-2-(4-methyl-2-oxopyridin-1(2H)-yl)thiazole-5-carboxamide

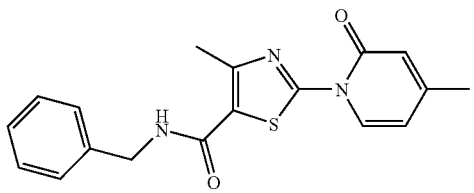 [SMILES: Cc1ccn(-c2nc(C)c(C(=O)NCc3ccccc3)s2)c(=O)c1]

To an oven-dried sealed tube under nitrogen atmosphere was added 145-(benzylcarbamoyl)-4-methylthiazol-2-yl)-2-oxo-1,2-dihydropyridin-4-yl trifluoromethanesulfonate (0.27 g, 0.56 mmol), trimethylboroxine (0.07 g, 0.62 mmol), tetrakis(triphenylphosphine)palladium(0) (0.13 g, 0.11 mmol) and potassium carbonate (0.23 g, 1.69 mmol), followed by the addition of dimethoxyethane (10 mL) and water (1 mL). The reaction mixture was heated at reflux for 18 hours, cooled to ambient temperature and ethyl acetate (30 mL) was added. The mixture was washed with saturated ammonium chloride (10 mL), dried over anhydrous sodium sulfate and filtered. The filtrate was concentrated in vacuo. The brown residue was purified by column chromatography eluted with ethyl acetate/hexane (4/1) to afford the title compound as a colorless solid in 54% yield (0.13 g): mp 145-147° C. (ethyl acetate/hexanes); $^1$H NMR (300 MHz, CDCl$_3$) δ 8.65 (d, J=7.5 Hz, 1H), 7.37-7.25 (m, 5H), 6.50 (s, 1H), 6.27 (dd, J=7.5, 1.7 Hz, 1H), 6.12 (t, J=5.6 Hz, 1H), 4.58 (d, J=5.6 Hz, 2H), 2.69 (s, 3H), 2.24 (s, 3H); $^{13}$C NMR (75 MHz, CDCl$_3$) δ 162.2, 160.4, 153.4, 152.2, 152.1, 137.7, 130.0, 128.8, 127.9, 127.7, 122.8, 119.1, 110.6, 44.1, 21.5, 17.3; MS (ES+) m/z 340.1 (M+1).

Example 21

Synthesis of N-Benzyl-4-methyl-2-(2-oxo-4-((5-phenyl-1,3,4-oxadiazol-2-yl)methoxy)pyridin-1(2H)-yl)thiazole-5-carboxamide

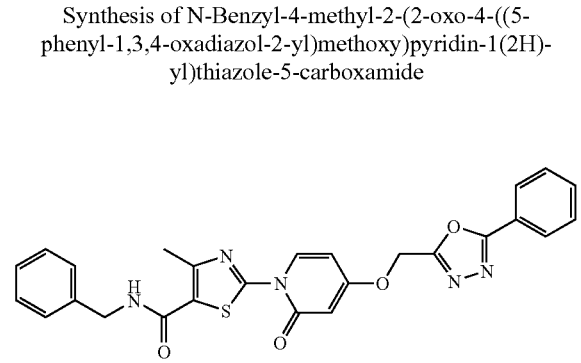

To a solution of N-benzyl-2-(4-hydroxy-2-oxopyridin-1(2H)-yl)-4-methylthiazole-5-carboxamide (0.20 g, 0.58 mmol) in anhydrous N,N-dimethylformamide (8 mL) was added cesium carbonate (0.32 g, 0.99 mmol) and catalytic amount of n-tetrabutylammonium iodide, followed by the addition of 2-(chloromethyl)-5-phenyl-1,3,4-oxadiazole (0.15 g, 0.76 mmol). The reaction mixture was heated at 80° C. for 20 hours and concentrated in vacuo, followed by the addition of dichloromethane (100 mL). The mixture was washed with water (70 mL). The organic layer was dried over anhydrous sodium sulfate and filtered. The solvent was concentrated in vacuo. The residue was recrystallized in ethyl acetate and hexane. The solid was collected by filtration and washed with methanol and hexanes to afford the title compound as a colorless solid in 38% yield (0.11 g): $^1$H NMR (300 MHz, DMSO-d$_6$) δ 8.84 (t, J=5.9 Hz, 1H), 8.69 (d, J=8.0 Hz, 1H), 8.04-8.01 (m, 2H), 7.69-7.57 (m, 3H), 7.37-7.29 (m, 4H), 7.27-7.21 (m, 1H), 6.50-6.43 (m, 2H), 5.64 (s, 2H), 4.42 (d, J=5.9 Hz, 2H), 2.58 (s, 3H); MS (ES+) m/z 500.2 (M+1), 522.2 (M+23).

Example 21.1

Synthesis of N-Benzyl-2-(4-((5-(4-chlorophenyl)-1,3,4-oxadiazol-2-yl)methoxy)-2-oxopyridin-1(2H)-yl)-4-methylthiazole-5-carboxamide

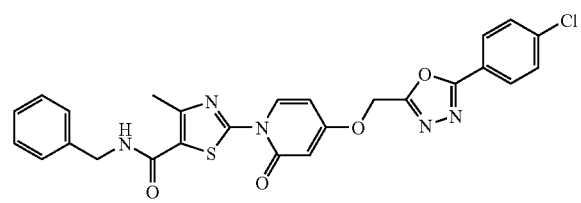 [SMILES: Cc1nc(-n2ccc(OCc3nnc(-c4ccc(Cl)cc4)o3)cc2=O)sc1C(=O)NCc1ccccc1]

Following the procedure as described in Example 21, making variation only as required to use 2-(chloromethyl)-5-(4-chlorophenyl)-1,3,4-oxadiazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 32% yield: $^1$H NMR (300 MHz, DMSO-d$_6$) δ 8.80 (t, J=5.8 Hz, 1H), 8.65 (d, J=7.8 Hz, 1H), 8.0 (d, J=8.6 Hz, 2H), 7.66 (d, J=8.5 Hz, 2H), 7.32-7.19 (m, 5H), 6.46-6.39 (m, 2H), 5.60 (s, 2H), 4.38 (d, J=5.8 Hz, 2H), 2.54 (s, 3H); MS (ES+) m/z 534.1 (M+1).

Example 21.2

Synthesis of N-Benzyl-2-(4-((8-chloro-6-(trifluoromethyl)naphthalen-2-yl)methoxy)-2-oxopyridin-1(2H)-yl)-4-methylthiazole-5-carboxamide

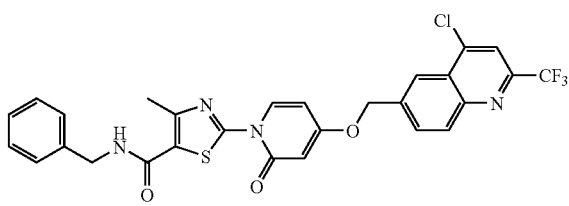 [SMILES: Cc1nc(-n2ccc(OCc3ccc4nc(C(F)(F)F)cc(Cl)c4c3)cc2=O)sc1C(=O)NCc1ccccc1]

Following the procedure as described in Example 21, making variation only as required to use 6-(bromomethyl)-4-chloro-2-(trifluoromethyl)quinoline in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 27% yield: $^1$H NMR (300 MHz, DMSO-d$_6$) δ 8.79 (t, J=5.9 Hz, 1H), 8.65 (d, J=8.1 Hz, 1H), 8.42-8.40 (m, 1H), 8.34-8.27 (m, 2H), 8.07-8.04 (m, 1H), 7.34-7.26 (m, 4H), 7.23-7.17 (m, 1H), 6.49 (dd, J=8.1, 2.6 Hz, 1H), 6.32 (d, J=2.6 Hz, 1H), 5.52 (s, 2H), 4.38 (d, J=5.9 Hz, 2H), 2.54 (s, 3H); MS (ES+) m/z 585.1 (M+1).

Example 21.3

Synthesis of N-Benzyl-4-methyl-2-(2-oxo-4-β6-(trifluoromethyl)pyridin-3-yl)methoxy)pyridin-1(2H)-yl)thiazole-5-carboxamide

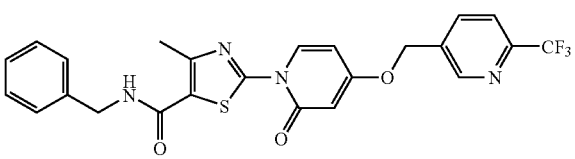 [SMILES: Cc1nc(-n2ccc(OCc3ccc(C(F)(F)F)nc3)cc2=O)sc1C(=O)NCc1ccccc1]

Following the procedure as described in Example 21, making variation only as required to use 5-(chloromethyl)-2-(trifluoromethyl)pyridine in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 49% yield: $^1$H NMR (300 MHz, DMSO-d$_6$) δ 8.85 (s, 1H), 8.79 (t, J=5.9 Hz, 1H), 8.64 (d, J=8.1 Hz, 1H), 8.17-8.14 (m, 1H), 7.95 (d, J=8.1 Hz, 1H), 7.38-7.17 (m, 5H), 6.43 (dd, J=8.1, 2.7 Hz, 1H), 6.28 (d, J=2.7 Hz, 1H), 5.35 (s, 2H), 4.38 (d, J=5.9 Hz, 2H), 2.54 (s, 3H); MS (ES+) m/z 501.2 (M+1).

Example 21.4

Synthesis of N-Benzyl-4-methyl-2-(2-oxo-4-(thiazol-4-ylmethoxy)pyridin-1(2H)-yl)thiazole-5-carboxamide

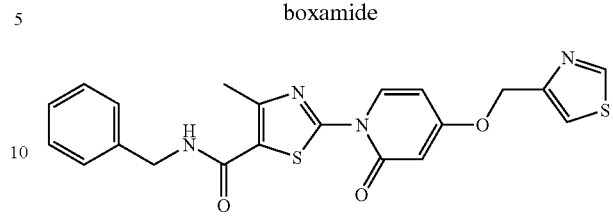

Following the procedure as described in Example 21, making variation only as required to use 4-(chloromethyl)thiazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 29% yield: $^1$H NMR (300 MHz, DMSO-d$_6$) δ 9.12 (d, J=1.9 Hz, 1H), 8.79 (t, J=5.9 Hz, 1H), 8.61 (d, J=8.0 Hz, 1H), 7.89 (d, J=1.9 Hz, 1H), 7.33-7.27 (m, 4H), 7.25-7.17 (m, 1H), 6.38-6.32 (m, 2H), 5.27 (s, 2H), 4.38 (d, J=5.9 Hz, 2H), 2.54 (s, 3H); MS (ES+) m/z 439.1 (M+1).

Example 21.5

Synthesis of N-Benzyl-4-methyl-2-(2-oxo-4-((tetrahydro-2H-pyran-2-yl)methoxy)pyridin-1(2H)-yl)thiazole-5-carboxamide

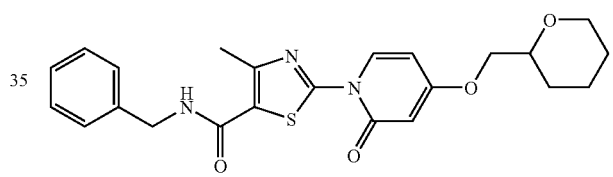

Following the procedure as described in Example 21, making variation only as required to use 2-(bromomethyl)tetrahydro-2H-pyran in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 66% yield: $^1$H NMR (300 MHz, DMSO-d$_6$) δ 8.77 (t, J=5.9 Hz, 1H), 8.58 (d, J=8.1 Hz, 1H), 7.36-7.26 (m, 4H), 7.23-7.18 (m, 1H), 6.34 (dd, J=8.1, 2.7 Hz, 1H), 6.11 (d, J=2.6 Hz, 1H), 4.38 (d, J=5.9 Hz, 2H), 4.03-3.94 (m, 2H), 3.86-3.82 (m, 1H), 3.62-3.55 (m, 1H), 3.38-3.31 (m, 1H), 2.53 (s, 3H), 1.76-1.69 (m, 1H), 1.59-1.20 (m, 5H); MS (ES+) m/z 440.2 (M+1).

Example 21.6

Synthesis of N-Benzyl-4-methyl-2-(4-((5-methylisoxazol-3-yl)methoxy)-2-oxopyridin-1(2H)-yl)thiazole-5-carboxamide

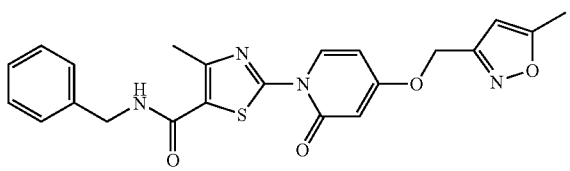 [SMILES: Cc1cc(COc2ccn(-c3nc(C)c(C(=O)NCc4ccccc4)s3)c(=O)c2)no1]

Following the procedure as described in Example 21, making variation only as required to use 3-(bromomethyl)-5-methylisoxazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 47% yield: ¹H NMR (300 MHz, DMSO-d₆) δ 8.79 (t, J=5.9 Hz, 1H), 8.62 (d, J=8.1 Hz, 1H), 7.35-7.18 (m, 5H), 6.38-6.35 (m, 2H), 6.26 (d, J=2.6 Hz, 1H), 5.22 (s, 2H), 4.38 (d, J=5.9 Hz, 2H), 2.54 (s, 3H), 2.38 (s, 3H); MS (ES+) m/z 437.2 (M+1).

Example 21.7

Synthesis of N-Benzyl-2-(4-((5-chlorothiophen-2-yl)methoxy)-2-oxopyridin-1(2H)-yl)-4-methylthiazole-5-carboxamide

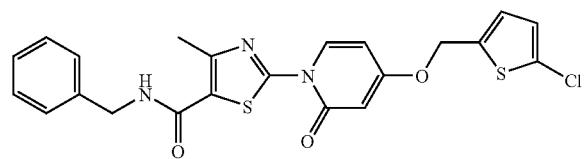 [SMILES: Cc1nc(-n2ccc(OCc3ccc(Cl)s3)cc2=O)sc1C(=O)NCc1ccccc1]

Following the procedure as described in Example 21, making variation only as required to use 2-chloro-5-(chloromethyl)thiophene in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 40% yield: ¹H NMR (300 MHz, DMSO-d₆) δ 8.78 (t, J=5.9 Hz, 1H), 8.60 (d, J=8.1 Hz, 1H), 7.30-7.18 (m, 5H), 7.15 (d, J=3.8 Hz, 1H), 7.05 (d, J=3.8 Hz, 1H), 6.34 (dd, J=8.1, 2.7 Hz, 1H), 6.28 (d, J=2.7 Hz, 1H), 5.30 (s, 2H), 4.38 (d, J=5.9 Hz, 2H), 2.54 (s, 3H); MS (ES+) m/z 471.9 (M+1), 473.8 (M+3).

Example 21.8

Synthesis of 2-(4-(Benzo[d]thiazol-2-ylmethoxy)-2-oxopyridin-1(2H)-yl)-N-benzyl-4-methylthiazole-5-carboxamide

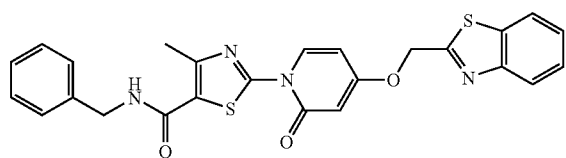 [SMILES: Cc1nc(-n2ccc(OCc3nc4ccccc4s3)cc2=O)sc1C(=O)NCc1ccccc1]

Following the procedure as described in Example 21, making variation only as required to use 2-(bromomethyl)benzo[d]thiazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 14% yield: ¹H NMR (300 MHz, DMSO-d₆) δ 8.79 (t, J=5.9 Hz, 1H), 8.66 (d, J=8.1 Hz, 1H), 8.13-8.11 (m, 1H), 8.03-8.00 (m, 1H), 7.55-7.42 (m, 2H), 7.34-7.18 (m, 5H), 6.48 (dd, J=8.1, 2.7 Hz, 1H), 6.34 (d, J=2.7 Hz, 1H), 5.68 (s, 2H), 4.38 (d, J=5.9 Hz, 2H), 2.54 (s, 3H); MS (ES+) m/z 489.1 (M+1).

Example 21.9

Synthesis of N-Benzyl-2-(4-((2-isopropylthiazol-4-yl)methoxy)-2-oxopyridin-1(2H)-yl)-4-methylthiazole-5-carboxamide

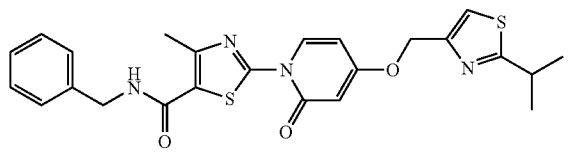 [SMILES: Cc1nc(-n2ccc(OCc3csc(C(C)C)n3)cc2=O)sc1C(=O)NCc1ccccc1]

Following the procedure as described in Example 21, making variation only as required to use 4-(chloromethyl)-2-isopropylthiazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 36% yield: ¹H NMR (300 MHz, CDCl₃) δ 8.67 (d, J=8.1 Hz, 1H), 7.34-7.23 (m, 5H), 7.21 (s, 1H), 6.28-6.20 (m, 1H), 6.10-6.04 (m, 2H), 5.12 (s, 2H), 4.59 (d, J=5.6 Hz, 2H), 3.38-3.27 (m, 1H), 2.68 (s, 3H), 1.45-1.35 (m, 6H); MS (ES+) m/z 481.2 (M+1).

Example 21.10

Synthesis of N-Benzyl-2-(4-((6-chloropyridin-3-yl)methoxy)-2-oxopyridin-1(2H)-yl)-4-methylthiazole-5-carboxamide

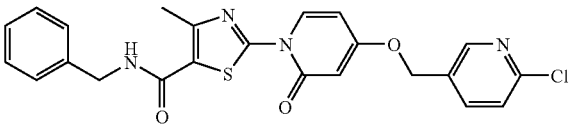

Following the procedure as described in Example 21, making variation only as required to use 2-chloro-5-(chloromethyl)pyridine in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 73% yield: ¹H NMR (300 MHz, DMSO-d₆) δ 8.79 (t, J=5.9 Hz, 1H), 8.62 (d, J=8.1 Hz, 1H), 8.51 (d, J=2.4 Hz, 1H), 7.95 (dd, J=8.3, 2.5 Hz, 1H), 7.57-7.54 (m, 1H), 7.35-7.16 (m, 5H), 6.39 (dd, J=8.1, 2.7 Hz, 1H), 6.26 (d, J=2.7 Hz, 1H), 5.22 (s, 2H), 4.38 (d, J=5.9 Hz, 2H), 2.54 (s, 3H); MS (ES+) m/z 467.0 (M+1).

Example 21.11

Synthesis of N-Benzyl-4-methyl-2-(4-((2-methylthiazol-4-yl)methoxy)-2-oxopyridin-1(2H)-yl)thiazole-5-carboxamide

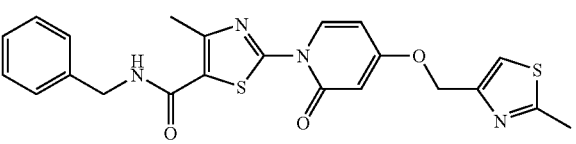 [SMILES: Cc1nc(COc2ccn(-c3nc(C)c(C(=O)NCc4ccccc4)s3)c(=O)c2)cs1]

Following the procedure as described in Example 21, making variation only as required to use 4-(chloromethyl)-2-methylthiazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 20% yield: $^1$H NMR (300 MHz, CDCl$_3$) δ 8.67 (d, J=8.1 Hz, 1H), 7.34-7.26 (m, 5H), 7.20 (s, 1H), 6.24 (dd, J=8.1, 2.7 Hz, 1H), 6.13-6.07 (m, 2H), 5.10 (s, 2H), 4.59 (d, J=5.6 Hz, 2H), 2.73 (s, 3H), 2.67 (s, 3H); MS (ES+) m/z 453.1 (M+1).

Example 21.12

Synthesis of 2-(4-((1,2,4-Oxadiazol-3-yl)methoxy)-2-oxopyridin-1(2H)-yl)-N-benzyl-4-methylthiazole-5-carboxamide

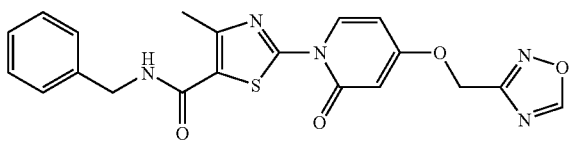 [SMILES: Cc1nc(-n2ccc(OCc3ncon3)cc2=O)sc1C(=O)NCc1ccccc1]

Following the procedure as described in Example 21, making variation only as required to use 3-(chloromethyl)-1,2,4-oxadiazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 20% yield: $^1$H NMR (300 MHz, DMSO-d$_6$) δ 8.81 (t, J=5.9 Hz, 1H), 8.66 (d, J=8.1 Hz, 1H), 7.36-7.17 (m, 6H), 6.42 (dd, J=8.1, 2.8 Hz, 1H), 6.33 (d, J=2.8 Hz, 1H), 5.26 (s, 2H), 4.38 (d, J=5.9 Hz, 2H), 2.55 (s, 3H); MS (ES+) m/z 424.1 (M+1).

Example 21.13

Synthesis of N-benzyl-2-(4-((3,5-dimethylisoxazol-4-yl)methoxy)-2-oxopyridin-1(2H)-yl)-4-methylthiazole-5-carboxamide

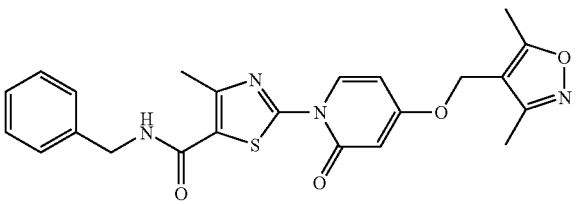 [SMILES: Cc1nc(-n2ccc(OCc3c(C)noc3C)cc2=O)sc1C(=O)NCc1ccccc1]

Following the procedure as described in Example 21, making variation only as required to use 4-(chloromethyl)-3,5-dimethylisoxazole in place of 2-(chloromethyl)-5-phenyl-1,3,4-oxadiazole to react with N-benzyl-2-(4-hydroxy-2-oxopyridin-1(2H)-yl)-4-methylthiazole-5-carboxamide, the title compound was obtained as a colorless solid in 10% yield: $^1$H NMR (300 MHz, CDCl$_3$) δ 8.69 (d, J=8.1 Hz, 1H), 7.41-7.26 (m, 5H), 6.16-6.06 (m, 3H), 4.76 (s, 2H), 4.59 (d, J=5.5 Hz, 2H), 2.68 (s, 3H), 2.41 (s, 3H), 2.27 (s, 3H); MS (ES+) m/z 451.1 (M+1).

Example 22

Synthesis of N-(Benzo[b]thiophen-2-ylmethyl)-2-(4-(benzyloxy)-2-oxopyridin-1(2H)-yl)-4-methylthiazole-5-carboxamide

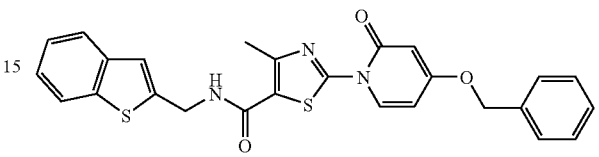

To a solution of 2-(4-(benzyloxy)-2-oxopyridin-1(2H)-yl)-4-methylthiazole-5-carboxylic acid (0.20 g, 0.58 mmol) in anhydrous N,N-dimethylformamide (10 mL) was added N,N-diisopropylethylamine (0.27 g, 2.10 mmol) and N-(3-dimethylaminopropyl)-N'-ethylcarbodiimide (0.18 g, 0.93 mmol). The mixture was stirred for 30 minutes, followed by the addition of 1-hydroxybenzotriazole (0.11 g, 0.81 mmol) and benzo[b]thiophen-2-ylmethanamine (0.14 mL, 0.87 mmol). The reaction mixture was stirred at ambient temperature for 24 hours. The solvent was removed in vacuo and the residue was dissolved in dichloromethane (50 mL), washed with saturated aqueous sodium bicarbonate (2×5 mL) and brine (10 mL). The organic layer was dried over anhydrous sodium sulfate, filtered and concentrated in vacuo. The residue was recrystallized from ethyl acetate and hexane. The solid was collected by filtration and washed with methanol and hexane. The title compound was obtained as a colorless solid in 78% yield (0.22 g): $^1$H NMR (300 MHz, DMSO-d$_6$) δ 8.98 (t, J=5.8 Hz, 1H), 8.61 (d, J=8.1 Hz, 1H), 7.82-7.85 (m, 1H), 7.76-7.73 (m, 1H), 7.51-7.23 (m, 8H), 6.34 (dd, J=8.1, 2.7 Hz, 1H), 6.23 (d, J=2.7 Hz, 1H), 5.16 (s, 2H), 4.65-4.63 (m, 2H), 2.56 (s, 3H); MS (ES+) m/z 488.1 (M+1).

Example 22.1

Synthesis of 2-(4-(Benzyloxy)-2-oxopyridin-1(2H)-yl)-4-methyl-N-((3-methylthiophen-2-yl)methyl)thiazole-5-carboxamide

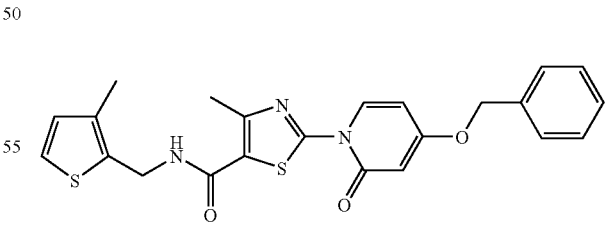

Following the procedure as described in Example 22, making variation only as required to use (3-methylthiophen-2-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 52% yield: $^1$H NMR (300 MHz, DMSO-d$_6$) δ 8.81 (t, J=5.8 Hz, 1H), 8.60 (d, J=8.1 Hz, 1H), 7.45-7.30 (m, 5H), 7.24 (d, J=5.1 Hz, 1H), 6.79 (d, J=5.1

Hz, 1H), 6.38 (dd, J=8.1, 2.7 Hz, 1H), 6.22 (d, J=2.7 Hz, 1H), 5.15 (s, 2H), 4.45-4.43 (m, 2H), 2.53 (s, 3H), 2.17 (s, 3H); MS (ES+) m/z 452.1 (M+1).

Example 22.2

Synthesis of 2-(4-(Benzyloxy)-2-oxopyridin-1(2H)-yl)-N-(2,3-dihydro-1H-inden-2-yl)-4-methylthiazole-5-carboxamide

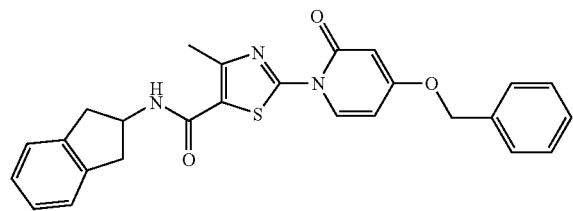 [SMILES: Cc1nc(-n2ccc(OCc3ccccc3)cc2=O)sc1C(=O)NC1Cc2ccccc2C1]

Following the procedure as described in Example 22, making variation only as required to use 2,3-dihydro-1H-inden-2-amine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 27% yield: $^1$H NMR (300 MHz, DMSO-$d_6$) δ 8.61 (d, J=8.1 Hz, 1H), 8.51 (d, J=7.0 Hz, 1H), 7.50-7.31 (m, 5H), 7.20-7.09 (m, 4H), 6.38 (dd, J=8.1, 2.7 Hz, 1H), 6.22 (d, J=2.7 Hz, 1H), 5.15 (s, 2H), 4.66-4.58 (m, 1H), 3.24-3.11 (m, 2H), 2.95-2.84 (m, 2H), 2.52 (s, 3H); MS (ES+) m/z 458.2 (M+1).

Example 22.3

Synthesis of 2-(4-(Benzyloxy)-2-oxopyridin-1(2H)-yl)-4-methyl-N-((5-methylpyrazin-2-yl)methyl)thiazole-5-carboxamide

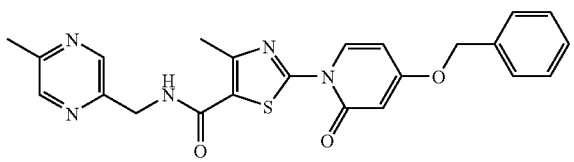 [SMILES: Cc1cnc(CNC(=O)c2sc(-n3ccc(OCc4ccccc4)cc3=O)nc2C)cn1]

Following the procedure as described in Example 22, making variation only as required to use (5-methylpyrazin-2-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 42% yield: $^1$H NMR (300 MHz, DMSO-$d_6$) δ 8.83 (t, J=5.7 Hz, 1H), 8.61 (d, J=8.1 Hz, 1H), 8.44 (s, 2H), 7.48-7.31 (m, 5H), 6.39 (dd, J=8.1, 2.7 Hz, 1H), 6.23 (d, J=2.7 Hz, 1H), 5.16 (s, 2H), 4.48 (d, J=5.7 Hz, 2H), 2.54 (m, 3H), 2.43 (s, 3H); MS (ES+) m/z 448.2 (M+1).

Example 22.4

Synthesis of 2-(4-(Benzyloxy)-2-oxopyridin-1(2H)-yl)-4-methyl-N-(oxazol-2-ylmethyl)thiazole-5-carboxamide

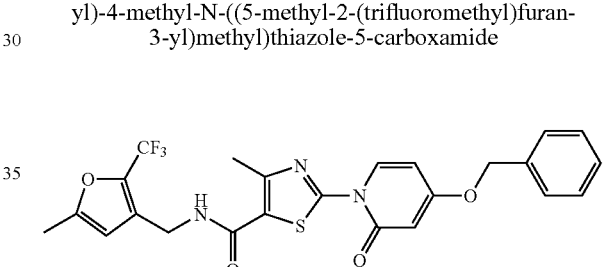

Following the procedure as described in Example 22, making variation only as required to use oxazol-2-ylmethanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 62% yield: $^1$H NMR (300 MHz, DMSO-$d_6$) δ 8.87 (t, J=5.7 Hz, 1H), 8.61 (d, J=8.1 Hz, 1H), 8.02 (s, 1H), 7.45-7.30 (m, 5H), 7.13 (s, 1H), 6.39 (dd, J=8.1, 2.7 Hz, 1H), 6.23 (d, J=2.7 Hz, 1H), 5.16 (s, 2H), 4.49 (d, J=5.7 Hz, 2H), 2.54 (m, 3H); MS (ES+) m/z 423.2 (M+1).

Example 22.5

Synthesis of 2-(4-(Benzyloxy)-2-oxopyridin-1(2H)-yl)-4-methyl-N-((5-methyl-2-(trifluoromethyl)furan-3-yl)methyl)thiazole-5-carboxamide

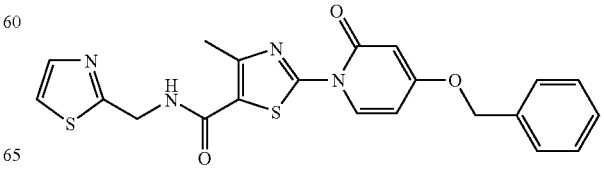

Following the procedure as described in Example 22, making variation only as required to use (5-methyl-2-(trifluoromethyl)furan-3-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 28% yield: $^1$H NMR (300 MHz, DMSO-$d_6$) δ 8.75 (t, J=5.7 Hz, 1H), 8.61 (d, J=8.1 Hz, 1H), 7.52-7.30 (m, 5H), 6.39 (dd, J=8.1, 2.7 Hz, 1H), 6.26 (s, 1H), 6.23 (d, J=2.7 Hz, 1H), 5.16 (s, 2H), 4.30 (d, J=5.7 Hz, 2H), 2.53 (m, 3H), 2.26 (m, 3H); MS (ES+) m/z 504.2 (M+1).

Example 22.6

Synthesis of 2-(4-(Benzyloxy)-2-oxopyridin-1(2H)-yl)-4-methyl-N-(thiazol-2-ylmethyl)thiazole-5-carboxamide Following the procedure as described in Example 22, making variation only as required to use thiazol-2-ylmethanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 71% yield: $^1$H NMR (300 MHz, DMSO-$d_6$) δ 9.11 (t, J=5.9 Hz, 1H), 8.61 (d, J=8.1 Hz, 1H), 7.70 (d, J=3.3 Hz, 1H), 7.60 (d, J=3.3 Hz, 1H), 7.45-7.33 (m, 5H), 6.39 (dd, J=8.1, 2.7 Hz, 1H), 6.23 (d, J=2.7 Hz, 1H), 5.16 (s, 2H), 4.66 (d, J=5.9 Hz, 2H), 2.56 (m, 3H); MS (ES+) m/z 439.1 (M+1).

Example 22.7

Synthesis of 2-(4-(Benzyloxy)-2-oxopyridin-1(2H)-yl)-4-methyl-N-((5-methylthiophen-2-yl)methyl)thiazole-5-carboxamide

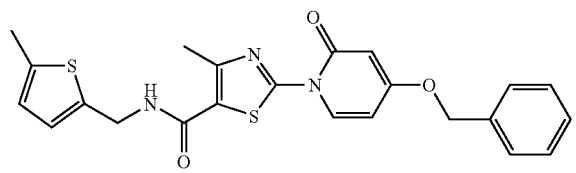 [SMILES: Cc1ccc(CNC(=O)c2sc(-n3ccc(OCc4ccccc4)cc3=O)nc2C)s1]

Following the procedure as described in Example 22, making variation only as required to use (5-methylthiophen-2-yl)methanamine in replace of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 43% yield: $^1$H NMR (300 MHz, DMSO-$d_6$) δ 8.82 (t, J=5.8 Hz, 1H), 8.60 (d, J=8.1 Hz, 1H), 7.45-7.30 (m, 5H), 6.73 (d, J=3.3 Hz, 1H), 7.59-6.57 (m, 1H), 6.38 (dd, J=8.1, 2.7 Hz, 1H), 6.22 (d, J=2.7 Hz, 1H), 5.16 (s, 2H), 4.43 (d, J=5.8 Hz, 2H), 2.53 (s, 3H), 2.34 (s, 3H); MS (ES+) m/z 452.1 (M+1).

Example 22.8

Synthesis of 2-(4-(Benzyloxy)-2-oxopyridin-1(2H)-yl)-4-methyl-N-((4-methylthiophen-2-yl)methyl)thiazole-5-carboxamide

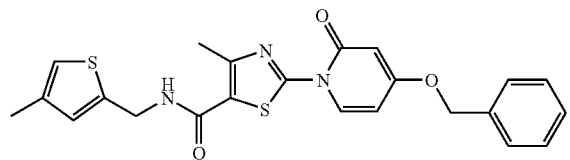 [SMILES: Cc1csc(CNC(=O)c2sc(-n3ccc(OCc4ccccc4)cc3=O)nc2C)c1]

Following the procedure as described in Example 22, making variation only as required to use (4-methylthiophen-2-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 46% yield: $^1$H NMR (300 MHz, DMSO-$d_6$) δ 8.83 (t, J=5.8 Hz, 1H), 8.60 (d, J=8.1 Hz, 1H), 7.50-7.31 (m, 5H), 6.91 (s, 1H), 6.77 (s, 1H), 6.38 (dd, J=8.1, 2.6 Hz, 1H), 6.22 (d, J=2.6 Hz, 1H), 5.15 (s, 2H), 4.46 (d, J=5.7 Hz, 2H), 2.53 (s, 3H), 2.12 (s, 3H); MS (ES+) m/z 452.2 (M+1).

Example 22.9

Synthesis of 2-(4-(Benzyloxy)-2-oxopyridin-1(2H)-yl)-N-((1,5-dimethyl-1H-pyrrol-2-yl)methyl)-4-methylthiazole-5-carboxamide

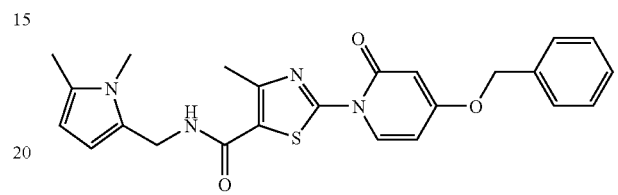

Following the procedure as described in Example 22, making variation only as required to use (1,5-dimethyl-1H-pyrrol-2-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 33% yield: $^1$H NMR (300 MHz, DMSO-$d_6$) δ 8.60 (d, J=8.1 Hz, 1H), 8.53 (t, J=5.4 Hz, 1H), 7.44-7.33 (m, 5H), 6.37 (dd, J=8.1, 2.7 Hz, 1H), 6.21 (d, J=2.7 Hz, 1H), 5.91 (d, J=3.3 Hz, 1H), 5.64-5.63 (m, 1H), 5.15 (s, 2H), 4.32 (d, J=5.4 Hz, 2H), 3.39 (s, 3H), 2.51 (s, 3H), 2.10 (s, 3H); MS (ES+) m/z 449.2 (M+1).

Example 22.10

Synthesis of 2-(4-(Benzyloxy)-2-oxopyridin-1(2H)-yl)-4-methyl-N-((1-methyl-1H-imidazol-5-yl)methyl)thiazole-5-carboxamide

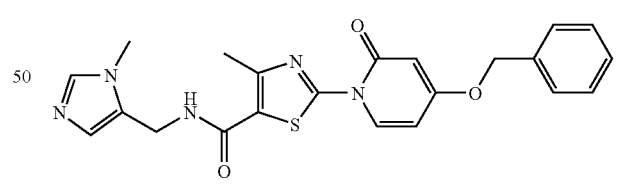

Following the procedure as described in Example 22, making variation only as required to use (1-methyl-1H-imidazol-5-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 52% yield: $^1$H NMR (300 MHz, DMSO-$d_6$) δ 8.65-8.58 (m, 2H), 7.51 (s, 1H), 7.44-7.30 (m, 5H), 6.78 (s, 1H), 6.38 (dd, J=8.1, 2.6 Hz, 1H), 6.22 (d, J=2.6 Hz, 1H), 5.15 (s, 2H), 4.36 (d, J=5.3 Hz, 2H), 3.58 (s, 3H), 2.52 (s, 3H); MS (ES+) m/z 436.2 (M+1).

Example 22.11

Synthesis of 2-(4-(Benzyloxy)-2-oxopyridin-1(2H)-yl)-4-methyl-N-((1-methyl-1H-pyrazol-4-yl)methyl)thiazole-5-carboxamide

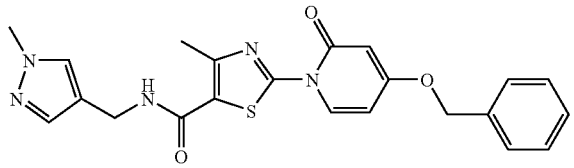 [SMILES: Cc1nc(-n2ccc(OCc3ccccc3)cc2=O)sc1C(=O)NCc1cnn(C)c1]

Following the procedure as described in Example 22, making variation only as required to use (1-methyl-1H-pyrazol-4-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 8% yield: $^1$H NMR (300 MHz, DMSO-$d_6$) δ 8.59 (d, J=8.1 Hz, 1H), 8.31 (br s, 2H), 7.69 (s, 1H), 7.50-7.30 (m, 5H), 6.30 (dd, J=8.1, 2.7 Hz, 1H), 6.13 (d, J=2.7 Hz, 1H), 5.13 (s, 2H), 3.82 (s, 2H), 3.77 (s, 3H), 2.52 (s, 3H); MS (ES+) m/z 436.1 (M+1).

Example 22.12

Synthesis of 2-(4-(Benzyloxy)-2-oxopyridin-1(2H)-yl)-4-methyl-N-((2-methylthiazol-4-yl)methyl)thiazole-5-carboxamide

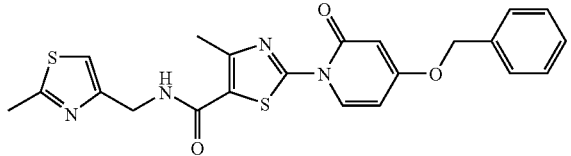 [SMILES: Cc1nc(CNC(=O)c2sc(-n3ccc(OCc4ccccc4)cc3=O)nc2C)cs1]

Following the procedure as described in Example 25, making variation only as required to use (2-methylthiazol-4-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 74% yield: $^1$H NMR (300 MHz, DMSO-$d_6$) δ 8.74 (t, J=5.7 Hz, 1H), 8.61 (d, J=8.1 Hz, 1H), 7.45-7.31 (m, 5H), 7.16 (s, 1H), 6.38 (dd, J=8.1, 2.7 Hz, 1H), 6.23 (d, J=2.7 Hz, 1H), 5.16 (s, 2H), 4.42 (d, J=5.7 Hz, 2H), 2.59 (s, 3H), 2.54 (s, 3H); MS (ES+) m/z 453.1 (M+1).

Example 22.13

Synthesis of 2-(4-(Benzyloxy)-2-oxopyridin-1(2H)-yl)-N-((5-cyanofuran-2-yl)methyl)-4-methylthiazole-5-carboxamide

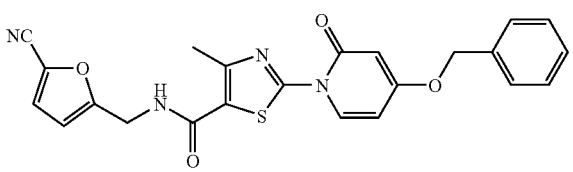

Following the procedure as described in Example 22, making variation only as required to use 5-(aminomethyl)furan-2-carbonitrile in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 72% yield: $^1$H NMR (300 MHz, DMSO-$d_6$) δ 8.84 (t, J=5.6 Hz, 1H), 8.61 (d, J=8.1 Hz, 1H), 7.52 (d, J=3.6 Hz, 1H), 7.45-7.30 (m, 5H), 6.55 (d, J=3.6 Hz, 1H), 6.39 (dd, J=8.1, 2.7 Hz, 1H), 6.23 (d, J=2.6 Hz, 1H), 5.16 (s, 2H), 4.44 (d, J=5.6 Hz, 2H), 2.54 (s, 3H); MS (ES+) m/z 447.1 (M+1).

Example 22.14

Synthesis of N-(Benzo[d]oxazol-2-ylmethyl)-2-(4-(benzyloxy)-2-oxopyridin-1(2H)-yl)-4-methylthiazole-5-carboxamide

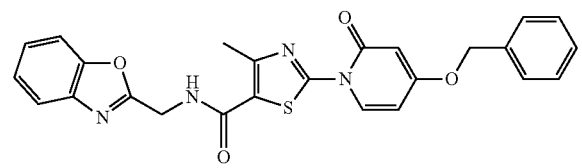 [SMILES: Cc1nc(-n2ccc(OCc3ccccc3)cc2=O)sc1C(=O)NCc1nc2ccccc2o1]

Following the procedure as described in Example 22, making variation only as required to use benzo[d]oxazol-2-ylmethanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 44% yield: $^1$H NMR (300 MHz, DMSO-$d_6$) δ 9.01 (t, J=5.5 Hz, 1H), 8.62 (d, J=8.1 Hz, 1H), 7.72-7.64 (m, 2H), 7.45-7.31 (m, 7H), 6.40 (dd, J=8.1, 2.7 Hz, 1H), 6.24 (d, J=2.7 Hz, 1H), 5.16 (s, 2H), 4.68 (d, J=5.5 Hz, 2H), 2.57 (s, 3H); MS (ES+) m/z 473.1 (M+1).

Example 22.15

Synthesis of Ethyl 5-((2-(4-(Benzyloxy)-2-oxopyridin-1(2H)-yl)-4-methylthiazole-5-carboxamido)methyl)furan-2-carboxylate

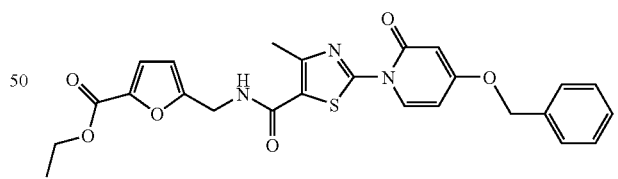

Following the procedure as described in Example 22, making variation only as required to use ethyl 5-(aminomethyl)furan-2-carboxylate in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 67% yield: $^1$H NMR (300 MHz, DMSO-$d_6$) δ 8.85 (t, J=5.6 Hz, 1H), 8.61 (d, J=8.1 Hz, 1H), 7.45-7.33 (m, 5H), 7.20 (d, J=3.5 Hz, 1H), 6.45 (d, J=3.5 Hz, 1H), 6.39 (dd, J=8.1, 2.7 Hz, 1H), 6.23 (d, J=2.7 Hz, 1H), 5.16 (s, 2H), 4.45 (d, J=5.5 Hz, 2H), 4.23 (q, J=7.1 Hz, 2H), 2.54 (s, 3H), 1.24 (t, J=7.1 Hz, 3H); MS (ES+) m/z 494.2 (M+1).

Example 22.16

Synthesis of N-((1H-Indol-2-yl)methyl)-2-(4-(benzyloxy)-2-oxopyridin-1(2H)-yl)-4-methylthiazole-5-carboxamide

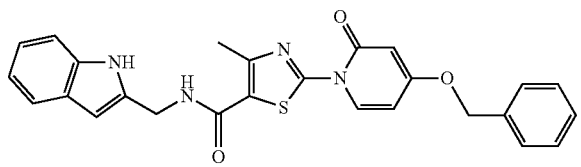 [SMILES: Cc1nc(-n2ccc(OCc3ccccc3)cc2=O)sc1C(=O)NCc1cc2ccccc2[nH]1]

Following the procedure as described in Example 22, making variation only as required to use (1H-indol-2-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 22% yield: $^1$H NMR (300 MHz, DMSO-$d_6$) δ 10.91 (s, 1H), 8.73 (t, J=5.6 Hz, 1H), 8.62 (d, J=8.1 Hz, 1H), 7.45-7.29 (m, 7H), 7.01-6.87 (m, 2H), 6.39 (dd, J=8.1, 2.7 Hz, 1H), 6.25-6.22 (m, 2H), 5.16 (s, 2H), 4.53 (d, J=5.6 Hz, 2H), 2.56 (s, 3H); MS (ES+) m/z 471.2 (M+1).

Example 22.17

Synthesis of N-(Benzo[d]thiazol-2-ylmethyl)-2-(4-(benzyloxy)-2-oxopyridin-1(2H)-yl)-4-methylthiazole-5-carboxamide

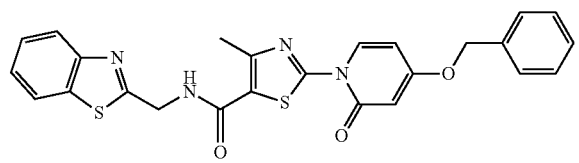 [SMILES: Cc1nc(-n2ccc(OCc3ccccc3)cc2=O)sc1C(=O)NCc1nc2ccccc2s1]

Following the procedure as described in Example 22, making variation only as required to use benzo[d]thiazol-2-ylmethanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 69% yield: $^1$H NMR (300 MHz, DMSO-$d_6$) δ 9.23 (t, J=5.8 Hz, 1H), 8.63 (d, J=8.1 Hz, 1H), 8.04-8.02 (m, 1H), 7.93-7.91 (m, 1H), 7.49-7.31 (m, 7H), 6.40 (dd, J=8.1, 2.7 Hz, 1H), 6.24 (d, J=2.7 Hz, 1H), 5.17 (s, 2H), 4.78 (d, J=5.8 Hz, 2H), 2.58 (s, 3H); MS (ES+) m/z 489.1 (M+1).

Example 22.18

Synthesis of N-((1H-Pyrazol-3-yl)methyl)-2-(4-(benzyloxy)-2-oxopyridin-1(2H)-yl)-4-methylthiazole-5-carboxamide

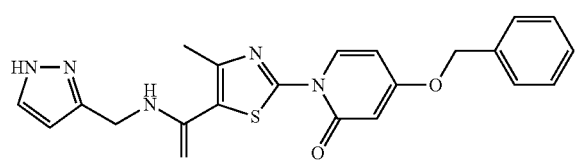

Following the procedure as described in Example 22, making variation only as required to use (1H-pyrazol-3-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 43% yield: $^1$H NMR (300 MHz, DMSO-$d_6$) δ 12.63 (br s, 1H), 8.74-8.54 (m, 2H), 7.63-7.31 (m, 6H), 6.38 (dd, J=8.1, 2.5 Hz, 1H), 6.22 (d, J=2.5 Hz, 1H), 6.13 (d, J=1.0 Hz, 1H), 5.15 (s, 2H), 4.37 (d, J=5.6 Hz, 2H), 2.53 (s, 3H); MS (ES+) m/z 422.2 (M+1).

Example 22.19

Synthesis of 2-(4-(Benzyloxy)-2-oxopyridin-1(2H)-yl)-N-((6-chloropyridin-3-yl)methyl)-4-methylthiazole-5-carboxamide

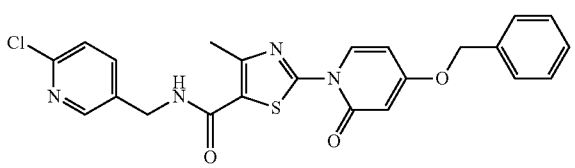 [SMILES: Cc1nc(-n2ccc(OCc3ccccc3)cc2=O)sc1C(=O)NCc1ccc(Cl)nc1]

Following the procedure as described in Example 22, making variation only as required to use (6-chloropyridin-3-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 60% yield: $^1$H NMR (300 MHz, DMSO-$d_6$) δ 8.82 (t, J=5.8 Hz, 1H), 8.60 (d, J=8.1 Hz, 1H), 8.34 (d, J=2.1 Hz, 1H), 7.77 (dd, J=8.2, 2.5 Hz, 1H), 7.51-7.28 (m, 6H), 6.38 (dd, J=8.1, 2.7 Hz, 1H), 6.23 (d, J=2.7 Hz, 1H), 5.16 (s, 2H), 4.39 (d, J=5.8 Hz, 2H), 2.53 (s, 3H); MS (ES+) m/z 467.0 (M+1).

Example 22.20

Synthesis of 2-(4-(Benzyloxy)-2-oxopyridin-1(2H)-yl)-4-methyl-N-((6-(trifluoromethyl)pyridin-3-yl)methyl)thiazole-5-carboxamide

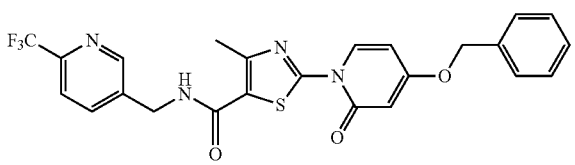 [SMILES: Cc1nc(-n2ccc(OCc3ccccc3)cc2=O)sc1C(=O)NCc1ccc(C(F)(F)F)nc1]

Following the procedure as described in Example 22, making variation only as required to use (6-(trifluoromethyl)pyridin-3-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 38% yield: $^1$H NMR (300 MHz, DMSO-$d_6$) δ 8.89 (t, J=5.6 Hz, 1H), 8.69 (br s, 1H), 8.61 (d, J=8.1 Hz 1H), 7.98-7.96 (m, 1H), 7.87-7.84 (m, 1H), 7.45-7.33 (m, 5H), 6.39 (dd, J=8.1, 2.6 Hz, 1H), 6.23 (d, J=2.6 Hz, 1H), 5.16 (s, 2H), 4.50 (d, J=5.6 Hz, 2H), 2.54 (s, 3H); MS (ES+) m/z 501.1 (M+1).

Example 22.21

Synthesis of 2-(4-(Benzyloxy)-2-oxopyridin-1(2H)-yl)-4-methyl-N-((5-methylfuran-2-yl)methyl)thiazole-5-carboxamide

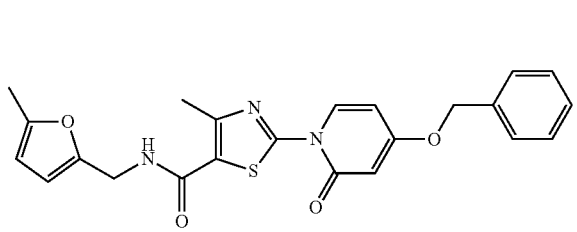 [SMILES: Cc1ccc(CNC(=O)c2sc(-n3ccc(OCc4ccccc4)cc3=O)nc2C)o1]

Following the procedure as described in Example 22, making variation only as required to use (5-methylfuran-2-yl)methanamine in place of benzo[b]thiophen-2-ylmethanamine to react with 2-(4-(benzyloxy)-2-oxopyridin-1(2H)-yl)-4-methylthiazole-5-carboxylic acid, the title compound was obtained as a colorless solid in 48% yield: $^1$H NMR (300 MHz, DMSO-$d_6$) δ 8.68 (t, J=5.6 Hz, 1H), 8.60 (d, J=8.1 Hz, 1H), 7.45-7.31 (m, 5H), 6.38 (dd, J=8.1, 2.7 Hz, 1H), 6.22 (d, J=2.7 Hz, 1H), 6.09 (d, J=3.0 Hz, 1H), 5.95 (d, J=3.0 Hz, 1H), 5.16 (s, 2H), 4.30 (d, J=5.6 Hz, 2H), 2.52 (s, 3H), 2.19 (s, 3H); MS (ES+) m/z 436.5 (M+1).

Example 23

Synthesis of 1-(5-(benzylcarbamoyl)-4-methylthiophen-2-yl)-2-oxo-1,2-dihydropyridin-4-yl trifluoromethanesulfonate

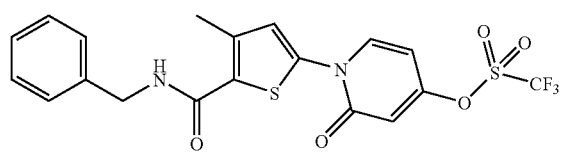 [SMILES: Cc1cc(-n2ccc(OS(=O)(=O)C(F)(F)F)cc2=O)sc1C(=O)NCc1ccccc1]

To a stirred suspension of N-benzyl-5-(4-hydroxy-2-oxopyridin-1(2H)-yl)-3-methylthiophene-2-carboxamide (0.34 g, 0.98 mmol) in dichloromethane (5 mL) under nitrogen atmosphere at −78° C. was added triethylamine (0.40 mL, 2.87 mmol), followed by dropwise addition of trifluoromethanesulfonic anhydride (0.18 mL, 1.07 mmol). The resulting reaction mixture was stirred at −78° C. for 15 minutes, and then quenched with water (25 mL). The aqueous layer was extracted with dichloromethane (50 mL). The organic layer was dried over sodium sulfate, filtered and concentrated in vacuo. The residue was purified by column chromatography eluted with 30% ethyl acetate in dichloromethane to afford the title compound as a cream color solid in 74% yield (0.34 g): $^1$H NMR (300 MHz, CDCl$_3$) δ 7.74 (d, J=7.9 Hz, 1H), 7.38-7.28 (m, 5H), 6.94 (s, 1H), 6.62 (d, J=2.7 Hz, 1H), 6.35 (dd, J=7.9, 2.7 Hz, 1H), 6.15 (t, J=5.3 Hz, 1H), 4.60 (d, J=5.3 Hz, 2H), 2.54 (s, 3H); MS (ES+) m/z 473.3 (M+1).

Example 24

Synthesis of N-benzyl-3-methyl-5-(2-oxo-4-phenethylpyridine-1(2H)-yl)thiophene-2-carboxamide

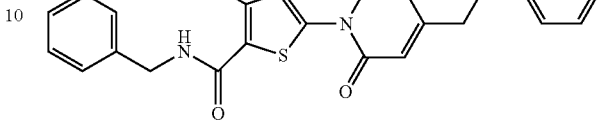

A mixture of 1-(5-(benzylcarbamoyl)-4-methylthiophen-2-yl)-2-oxo-1,2-dihydropyridin-4-yl trifluoromethanesulfonate (0.15 g, 0.32 mmol), phenethyl boronic acid (0.047 g, 0.31 mmol), [1,1'-bis(diphenylphosphino)ferrocene]dichloropalladium(II), 1:1 complex with dichloromethane (0.023 g, 0.028 mmol) and potassium carbonate (0.13 g, 0.95 mmol) in tetrahydrofuran (3 mL) and water (0.3 mL) was stirred in a sealed tube at 70° C. for 16 hours under nitrogen atmosphere. The reaction mixture was allowed to cool to ambient temperature, and was partitioned between ethyl acetate (75 mL) and water (35 mL). The organic layer was washed sequentially with 10% aqueous hydrochloric acid (30 mL), saturated aqueous sodium bicarbonate solution (2×25 mL) and brine (30 mL), then dried over sodium sulfate, filtered and concentrated in vacuo. The residue was purified by column chromatography eluted with 20% ethyl acetate in dichloromethane to afford the title compound as a light cream color solid in 40% yield (0.054 g): mp 145-146° C.; $^1$H NMR (300 MHz, CDCl$_3$) δ 7.59 (d, J=7.3 Hz, 1H), 7.38-7.15 (m, 10H), 6.89 (s, 1H), 6.48 (s, 1H), 6.19 (t, J=5.8 Hz, 1H), 6.16 (dd, J=7.3, 1.9 Hz, 1H), 4.59 (d, J=5.8 Hz, 2H), 2.96-2.87 (m, 2H), 2.84-2.75 (m, 2H), 2.54 (s, 3H); $^{13}$C NMR (75 MHz, CDCl$_3$) δ 162.9, 160.7, 154.3, 140.1, 139.54, 139.5, 137.9, 133.2, 128.7, 128.6, 128.3, 127.8, 127.6, 127.2, 126.4, 121.8, 119.2, 109.3, 43.9, 36.9, 35.1, 15.9; MS (ES+) m/z 429.3 (M+1).

Example 25

Synthesis of N-(3-Fluorobenzyl)-5-(4-(3-hydroxypropoxy)-2-oxopyridin-1(2H)-yl)-3-methylthiophene-2-carboxamide

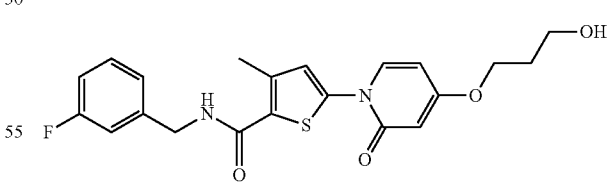

A solution of 5-(4-(3-(tert-butyldimethylsilyloxy)propoxy)-2-oxopyridin-1(2H)-yl)-N-(3-fluorobenzyl)-3-methylthiophene-2-carboxamide (0.368 mmol) in acetic acid (5 mL) was stirred at 60° C. for 16 hours. The reaction mixture was allowed to cool to ambient temperature and concentrated in vacuo. The residue was purified by column chromatography eluted with 0-10% methanol in dichloromethane to afford the title compound as a pinkish solid in 61% yield (0.093 g): mp 135-137° C.; $^1$H NMR (300 MHz, DMSO-$d_6$) δ 8.58 (t, J=6.0 Hz, 1H), 8.14 (d, J=7.9 Hz, 1H), 7.42-7.33 (m, 1H), 7.26 (s, 1H), 7.18-7.03 (m, 3H), 6.21 (dd, J=7.9, 2.7 Hz, 1H), 6.01 (d, J=2.7 Hz, 1H), 4.60 (br s, 1H), 4.42 (d, J=6.0 Hz, 2H), 4.09 (t, J=6.2 Hz, 2H), 3.54 (t, J=6.2 Hz, 2H), 2.42 (s, 3H), 1.86 (p, J=6.2 Hz, 2H); $^{13}$C NMR (75 MHz, DMSO-d$_6$) δ 166.6, 162.5, 162.1 (d, $J_{C-F}$=243.2 Hz), 161.0, 142.7 (d, $J_{C-F}$=7.0 Hz), 138.9, 137.4, 134.8, 130.1 (d, $J_{C-F}$=8.3 Hz), 127.0, 123.1 (d, $J_{C-F}$=2.7 Hz), 120.4, 113.8 (d, $J_{C-F}$=21.5 Hz), 113.4 (d, $J_{C-F}$=20.9 Hz), 102.6, 96.6, 65.6, 56.9, 42.1, 31.4, 15.5; MS (ES+) m/z 417.3 (M+1).

Example 26

Synthesis of N-Benzyl-4-methyl-2-(2-oxo-4-(2-oxoimidazolidin-1-yl)pyridin-1(2H)-yl)thiazole-5-carboxamide

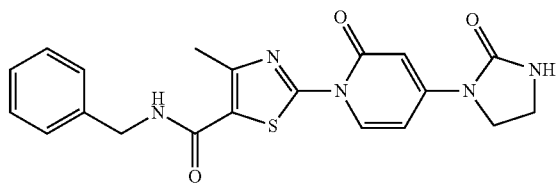 [SMILES: Cc1nc(-n2ccc(N3CCNC3=O)cc2=O)sc1C(=O)NCc1ccccc1]

To a solution of 2-(4-amino-2-oxopyridin-1(2H)-yl)-N-benzyl-4-methylthiazole-5-carboxamide (0.14 g, 0.41 mmol) in N,N-dimethylformamide (10 mL) was added 2-chloroethyl isocyanate (0.05 mL, 0.58 mmol) at ambient temperature. The resulting reaction mixture was heated at 80-90° C. for 7 hours. Potassium carbonate (0.10 g, 0.72 mmol) was added and the reaction mixture was heated for 18 hours. The solvent was removed in vacuo, and the residue was purified by column chromatography to afford the title compound in 6% yield (0.01 g): mp>300° C.; $^1$H NMR (300 MHz, DMSO-d$_6$) δ 8.76 (t, J=6.0 Hz, 1H), 8.56 (d, J=8.4 Hz, 1H), 7.64-7.17 (m, 7H), 6.08 (d, J=2.1 Hz, 1H), 4.38 (d, J=6.0 Hz, 2H), 3.85-3.79 (m, 2H), 3.42-3.37 (m, 2H), 2.60 (s, 3H); $^{13}$C NMR (75 MHz, DMSO-d$_6$) δ 161.9, 160.7, 157.8, 153.8, 150.7, 150.4, 139.9, 130.9, 128.7, 127.7, 127.2, 123.7, 101.4, 98.8, 44.3, 43.1, 36.5, 17.5; MS (ES+) m/z 410.2 (M+1).

Example 27

Synthesis of 3-((2-(4-methoxy-2-oxopyridin-1(2H)-yl)-4-methylthiazole-5-carboxamido)methyl)pyridine 1-oxide

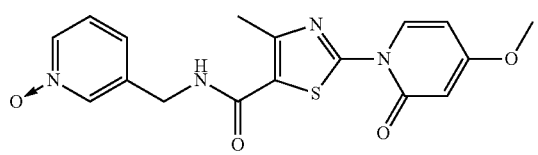 [SMILES: COc1ccn(-c2nc(C)c(C(=O)NCc3ccc[n+]([O-])c3)s2)c(=O)c1]

To a stirred solution of 2-(4-methoxy-2-oxopyridin-1(2H)-yl)-4-methyl-N-(pyridin-3-ylmethyl)thiazole-5-carboxamide (0.10 g, 0.28 mmol) in anhydrous dichloromethane (10 mL) was added m-chloroperoxy benzoic acid (0.072 g, 0.42 mmol) at ambient temperature. The reaction mixture was stirred at ambient temperature for 24 hours, diluted with dichloromethane (100 mL), washed with saturated bicarbonate solution (20 mL) and brine (20 mL). The organic layer was dried over sodium sulfate, filtered and concentrated in vacuo. The residue was crystallized in ethyl acetate and hexane. The solid was collected by filtration and washed with methanol and hexane to afford the title compound as a colorless solid in 34% yield (0.035 g): mp 255-257° C. (ethyl acetate/hexanes); $^1$H NMR (300 MHz, DMSO-d$_6$) δ 8.81 (t, J=5.8 Hz, 1H), 8.59 (d, J=8.1 Hz, 1H), 8.13 (s, 1H), 8.09 (d, J=6.3 Hz, 1H), 7.37-7.23 (m, 2H), 6.33 (dd, J=8.1, 2.7 Hz, 1H), 6.12 (d, J=2.7 Hz, 1H), 4.34 (d, J=5.7 Hz, 2H), 3.81 (s, 3H), 2.54 (s, 3H); $^{13}$C NMR (75 MHz, DMSO-d$_6$) δ 168.6, 162.2, 161.7, 154.1, 151.0, 139.3, 138.1, 137.7, 131.9, 126.7, 124.9, 123.0, 104.2, 96.5, 56.8, 42.1, 17.5; MS (ES+) m/z 373.3 (M+1), 395.2 (M+23).

Example 28

Measuring Stearoyl-CoA Desaturase Inhibition Activity of a Test Compound Using Mouse Liver Microsomes The identification of compounds of the invention as SCD inhibitors was readily accomplished using the SCD microsomal assay procedure described in Shanklin J. and Summerville C., *Proc. Natl. Acad. Sci. USA* (1991), Vol. 88, pp. 2510-2514.

Preparation of Mouse Liver Microsomes

Male ICR outbread mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1/3 w/v) containing 0.25 M sucrose, 62 mM potassium phosphate buffer (pH 7.0), 0.15 M KCl, 15 mM N-acetylcysteine, 5 mM MgCl$_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Desaturase activity is measured as the release of $^3$H$_2$O from [9,10-$^3$H]stearoyl-CoA. Reactions per assay point conditions are as follows: 2 μL 1.5 mM stearoyl-CoA, 0.25 μL 1 mCi/mL $^3$H stearoyl CoA, 10 μL 20 mM NADH, 36.75 μL 0.1 M PK buffer (K$_2$HPO$_4$/NaH$_2$PO$_4$, pH 7.2). The test compound or control solution is added in a 1 µL volume. Reactions are started by adding 50 µL of microsomes (1.25 mg/mL). The plates are mixed and after 15 min incubation on a heating block (25° C.), the reactions are stopped by the addition of 10 µL 60% PCA. An aliquot of 100 µL is then transferred to a filter plate pretreated with charcoal and the plate centrifuged at 4000 rpm for 1 minute. The flow through containing the $^3H_2O$ released by the SCD1 desaturation reaction is added to scintillation fluid and the radioactivity measured in a Packard TopCount. The data is analysed to identify the $IC_{50}$ for test compounds and reference compounds.

Representative compounds of the invention showed activity as inhibitors of SCD when tested in this assay. The activity was defined in terms of % SCD enzyme activity remaining at the desired concentration of the test compound or as the $IC_{50}$ concentration. The $IC_{50}$ (affinity) of the example compounds toward the stearoyl-CoA desaturase is comprised between around 500 micro Molar and 0.0001 micro Molar or between around 100 micro Molar and 0.002 micro Molar or between around 10 micro Molar and 0.002 micro Molar. Some results are shown in Table 1 below.

TABLE 1

| Example No. | Compound Name | Microsomal IC50 (µm) |
|---|---|---|
| 1.1 | N-benzyl-2-(4-(cyclopropylmethoxy)-2-oxopyridin-1(2H)-yl)-4-methylthiazole-5-carboxamide | 0.40 |
| 1.2 | N-benzyl-2-(4-methoxy-2-oxopyridin-1(2H)-yl)-4-methylthiazole-5-carboxamide | 0.09 |
| 3.11 | N-(4-fluorobenzyl)-4-methyl-2-(2-oxopyridin-1(2H)-yl)thiazole-5-carboxamide | 0.23 |
| 1.7 | N-benzyl-2-(4-(benzyloxy)-2-oxopyridin-1(2H)-yl)-4-methyl-1H-imidazole-5-carboxamide | 0.22 |
| 7.6 | 5-(4-hydroxy-2-oxopyridin-1(2H)-yl)-3-methyl-N-(pyridin-3-ylmethyl)thiophene-2-carboxamide | 0.80 |
| 1.22 | 2-(4-hydroxy-2-oxopyridin-1(2H)-yl)-4-methyl-N-(oxazol-2-ylmethyl)thiazole-5-carboxamide | 0.43 |
| 21.13 | N-benzyl-2-(4-((3,5-dimethylisoxazol-4-yl)methoxy)-2-oxopyridin-1(2H)-yl)-4-methylthiazole-5-carboxamide | 0.18 |
| 22.19 | 2-(4-(benzyloxy)-2-oxopyridin-1(2H)-yl)-N-((6-chloropyridin-3-yl)methyl)-4-methylthiazole-5-carboxamide | 0.05 |
| 3.5 | N-benzyl-4-methyl-2-(2-oxo-3-(trifluoromethyl)pyridin-1(2H)-yl)thiazole-5-carboxamide | 0.15 |
| 7.1 | N-benzyl-2-(5-hydroxy-1-oxoisoquinolin-2(1H)-yl)-4-methylthiazole-5-carboxamide | 0.03 |
| 3.19 | N-benzyl-5-(4-(benzyloxy)-2-oxopyridin-1(2H)-yl)-3-methylfuran-2-carboxamide | 5.70 |

Those skilled in the art are aware of a variety of modifications to this assay that can be useful for measuring inhibition of stearoyl-CoA desaturase activity in microsomes or in cells by test compounds.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention.

Accordingly, the invention is not limited except as by the appended claims.

The invention claimed is:
1. A compound of Formula (I):

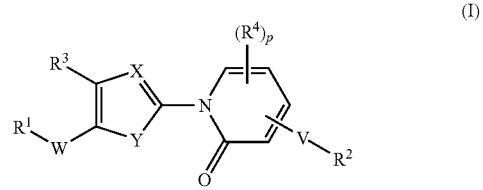

wherein,
V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_t$—, —S(O)$_t$N(R$^5$)—, —OS(O)$_2$—, —OS(O)$_2$N(R$^5$)—, —N(R$^5$)C(=N(R$^{5a}$))NR$^5$—, —N(R$^5$)C(=S)NR$^5$—, —N(R$^5$)((R$^{5a}$)N=)C—, —C(=N(R$^{5a}$))N(R$^5$)—, alkylene, alkenylene, alkynylene, aryl, heteroaryl, cycloalkyl, heterocyclyl or a direct bond;
W is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —N(R$^5$)—, —S—, —S(O)$_t$—, —N(R$^5$)S(O)$_t$—, —S(O)$_t$N(R$^5$)—, —OS(O)$_2$N(R$^5$)—, —C(O)—, —OC(O)—, —C(O)O—, —N(R$^5$)C(=N(R$^5$))NR$^5$—, —N(R$^5$)((R$^{5a}$)N=)C—, —C(=N(R$^5$))N(R$^5$)—, aryl, heteroaryl, heterocyclyl, alkynylene, alkenylene, alkylene or a direct bond;
X is selected from C(H) or N;
Y is selected from S, N(H) or N(CH$_3$);
p is 0, 1, 2, or 3;
t is 1 or 2;
R$^1$ is selected from the group consisting of hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, and heteroarylalkyl;
or R$^1$ is a multi-ring structure having 2 to 4 rings wherein the rings are independently selected from the group consisting of cycloalkyl, heterocyclyl, aryl and heteroaryl and where some or all of the rings may be fused to each other;
R$^2$ is selected from the group consisting of hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl and heteroarylalkyl;
R$^3$ is selected from the group consisting of alkyl, alkenyl, alkoxy, hydroxyalkyl, alkoxyalkyl, cycloalkyl, cycloalkylalkyl, heterocyclyl, aryl, aralkyl, heteroaryl, halo, haloalkyl, haloalkoxyl, cyano and —N(R$^5$)$_2$;
R$^4$ is selected from the group consisting of alkyl, hydroxyalkyl, cycloalkylalkyl, aralkyl, halo, haloalkyl, —OCF$_3$ and —OC(H)F$_2$;
R$^5$ is selected from the group consisting of hydrogen, aryl, alkyl, heteroaryl, heterocyclyl, haloalkyl, hydroxyalkyl, cycloalkylalkyl and aralkyl;
R$^{5a}$ is selected from the group consisting of hydrogen, alkyl, cycloalkylalkyl and cyano;
a stereoisomer, enantiomer or tautomer thereof, a pharmaceutically acceptable salt thereof.
2. The compound according to claim 1, wherein X is C(H) and Y is S.

3. The compound according to claim 1, wherein X is N and Y is S.

4. The compound according to claim 1, wherein X is N and Y is N(H) or N(CH₃).

5. The compound according to claim 1, wherein
V is selected from —O— or a direct bond;
W is selected from —N(R⁵)C(O)—, —C(O)N(R⁵)—, —C(O)O— or a direct bond;
X is selected from C(H) or N;
Y is selected from S, N(H) or N(CH₃);
p is 0, 1, 2, or 3;
R¹ is selected from the group consisting of hydrogen, alkyl, aryl, aralkyl, alkoxy, heterocyclyl, heterocyclylalkyl, heteroaryl, and heteroarylalkyl;
R² is selected from the group consisting of hydrogen, alkyl, alkynyl, alkoxyl, hydroxyalkyl, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is alkyl or haloalkyl; and
R⁵ is selected from the group consisting of hydrogen or alkyl.

6. The compound according to claim 2, wherein
V is selected from —O— or a direct bond;
W is selected from —N(R⁵)C(O)—, —C(O)N(R⁵)—, —C(O)O— or a direct bond;
p is 0, 1, 2, or 3;
R¹ is selected from the group consisting of hydrogen, alkyl, aryl, aralkyl, heterocyclyl, heterocyclylalkyl, heteroaryl, and heteroarylalkyl;
R² is selected from the group consisting of hydrogen, alkyl, alkynyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is alkyl or haloalkyl; and
R⁵ is selected from the group consisting of hydrogen or alkyl.

7. The compound according to claim 3, wherein
V is selected from —O— or a direct bond;
W is selected from —N(R⁵)C(O)—, —C(O)N(R⁵)—, —OC(O)—, —C(O)O— or a direct bond;
p is 0, 1, 2, or 3;
R¹ is selected from the group consisting of hydrogen, alkyl, cycloalkylalkyl, aryl, aralkyl, heterocyclyl, heterocyclylalkyl, heteroaryl, and heteroarylalkyl;
R² is selected from the group consisting of hydrogen, alkyl, alkynyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is alkyl, halo and haloalkyl;
or two adjacent R⁴ groups, together with the carbon atoms to which they attached, may form a cycloalkyl, heterocyclyl, aryl or heteroaryl and the remaining R⁴ groups, if present, are as described above; and
R⁵ is selected from the group consisting of hydrogen or alkyl.

8. The compound according to claim 7, wherein
V is a direct bond;
W is —N(R⁵)C(O)— or —OC(O)—;
p is 0, 1 or 2;
R¹ is selected from the group consisting of hydrogen, alkyl, cycloalkylalkyl, aryl, aralkyl, heterocyclyl, heterocyclylalkyl, heteroaryl, and heteroarylalkyl;
R² is selected from the group consisting of hydrogen, alkyl, alkynyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is alkyl, halo and haloalkyl;
or two adjacent R⁴ groups, together with the carbon atoms to which they attached, may form a cycloalkyl, heterocyclyl, aryl or heteroaryl and the remaining R⁴ groups, if present, are as described above; and
R⁵ is selected from the group consisting of hydrogen or alkyl.

9. The compound according to claim 7, wherein
V is —O—;
W is —N(R⁵)C(O)— or —OC(O)—;
p is 0, 1 or 2;
R¹ is selected from the group consisting of hydrogen, alkyl, cycloalkylalkyl, aryl, aralkyl, heterocyclyl, heterocyclylalkyl, heteroaryl, and heteroarylalkyl;
R² is selected from the group consisting of hydrogen, alkyl, alkynyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is alkyl, halo and haloalkyl;
or two adjacent R⁴ groups, together with the carbon atoms to which they attached, may form a cycloalkyl, heterocyclyl, aryl or heteroaryl and the remaining R⁴ groups, if present, are as described above; and
R⁵ is selected from the group consisting of hydrogen or alkyl.

10. The compound according to claim 4, wherein
V is selected from —O— or a direct bond;
W is selected from —N(R⁵)C(O)—, —C(O)N(R⁵)—, —OC(O)—, —C(O)O— or a direct bond;
p is 0, 1, 2, or 3;
R¹ is selected from the group consisting of hydrogen, alkyl, aryl, aralkyl, heterocyclyl, heterocyclylalkyl, heteroaryl, and heteroarylalkyl;
R² is selected from the group consisting of hydrogen, alkyl, alkenyl, alkynyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is alkyl, halo and haloalkyl;
or two adjacent R⁴ groups, together with the carbon atoms to which they attached, may form a cycloalkyl, heterocyclyl, aryl or heteroaryl and the remaining R⁴ groups, if present, are as described above; and
R⁵ is selected from the group consisting of hydrogen or alkyl.

11. The compound according to claim 1, wherein
V is selected from —C(O)N(R⁵)—, —N(R⁵)—, —O—, —OS(O)₂— or a direct bond;
W is selected from —N(R⁵)C(O)—, —OC(O)— or —C(O)O—;
X is selected from C(H) or N;
Y is selected from S, N(H) or N(CH₃);
p is 0, 1, 2, or 3;
R¹ is selected from the group consisting of alkyl, aryl, aralkyl, heterocyclyl, heterocyclylalkyl, and heteroarylalkyl;
R² is selected from the group consisting of hydrogen, alkyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is haloalkyl or alkyl; and R⁵ is selected from the group consisting of hydrogen or alkyl.

12. The compound according to claim 2, wherein
V is selected from —O—, —N(R⁵)—, —OS(O)₂— or a direct bond;
W is selected from —N(R⁵)C(O)—, or —C(O)O—;
p is 0, 1, 2, or 3;
R¹ is selected from the group consisting of alkyl, aryl, aralkyl, heterocyclyl, heterocyclylalkyl, and heteroarylalkyl;
R² is selected from the group consisting of hydrogen, alkyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is haloalkyl or alkyl; and
R⁵ is selected from the group consisting of hydrogen or alkyl.

13. The compound according to claim 3, wherein
V is selected from —C(O)N(R⁵)—, —N(R⁵)—, —O—, —OS(O)₂— or a direct bond;
W is selected from —N(R⁵)C(O)—, —OC(O)— or —C(O)O—;
p is 0, 1, 2, or 3;
R¹ is selected from the group consisting of alkyl, aryl, aralkyl, heterocyclyl, heterocyclylalkyl, and heteroarylalkyl;
R² is selected from the group consisting of hydrogen, alkyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is alkyl or haloalkyl; and
R⁵ is selected from the group consisting of hydrogen or alkyl.

14. The compound according to claim 4, wherein
V is selected from —C(O)N(R⁵)—, —N(R⁵)—, —O—, —OS(O)₂— or a direct bond;
W is selected from —N(R⁵)C(O)—, —OC(O)— or —C(O)O—;
p is 0, 1, 2, or 3;
R¹ is selected from the group consisting of alkyl, aryl, aralkyl, heterocyclyl, heterocyclylalkyl, and heteroarylalkyl;
R² is selected from the group consisting of hydrogen, alkyl, hydroxyalkyl, alkoxy, alkoxyalkyl, cycloalkyl, cycloalkylalkyl, aryl, haloalkyl, aralkyl, heterocyclyl, heterocyclylalkyl, heteroaryl and heteroarylalkyl;
R³ is alkyl;
R⁴ is haloalkyl or alkyl; and
R⁵ is selected from the group consisting of hydrogen or alkyl.

15. The compound according to claim 1, wherein the compound is selected from the group consisting of:
N-benzyl-4-methyl-2-(2-oxo-4-phenylpyridin-1(2H)-yl)thiazole-5-carboxamide;
N-Benzyl-2-(5-(benzyloxy)-2-oxopyridin-1(2H)-yl)-4-methylthiazole-5-carboxamide;
N-Benzyl-2-(4-hydroxy-2-oxopyridin-1(2H)-yl)-4-methylthiazole-5-carboxamide;
N-benzyl-2-(4-(4-chlorophenyl)-2-oxopyridin-1(2H)-yl)-4-methylthiazole-5-carboxamide;
N-benzyl-2-(4-(cyclopropylmethoxy)-2-oxopyridin-1(2H)-yl)-4-methylthiazole-5-carboxamide;
N-benzyl-2-(4-methoxy-2-oxopyridin-1(2H)-yl)-4-methylthiazole-5-carboxamide;
N-(4-fluorobenzyl)-2-(4-hydroxy-2-oxopyridin-1(2H)-yl)-4-methylthiazole-5-carboxamide;
N-benzyl-2-(4-(2-cyclopropylethoxy)-2-oxopyridin-1(2H)-yl)-4-methylthiazole-5-carboxamide;
2-(4-amino-2-oxopyridin-1(2H)-yl)-N-benzyl-4-methylthiazole-5-carboxamide;
N-benzyl-4-methyl-2-(2-oxopyridin-1(2H)-yl)thiazole-5-carboxamide;
N-benzyl-4-methyl-2-(2-oxo-4-(phenylcarbamoyl)pyridin-1(2H)-yl)thiazole-5-carboxamide;
N-benzyl-2-(3-(benzyloxy)-2-oxopyridin-1(2H)-yl)-4-methylthiazole-5-carboxamide;
N-benzyl-2-(3-hydroxy-2-oxopyridin-1(2H)-yl)-4-methylthiazole-5-carboxamide;
N-benzyl-4-methyl-2-(2-oxo-3-(phenylcarbamoyl)pyridin-1(2H)-yl)thiazole-5-carboxamide;
N-benzyl-4-methyl-2-(2-oxo-5-(phenylcarbamoyl)pyridin-1(2H)-yl)thiazole-5-carboxamide;
2-(4-benzamido-2-oxopyridin-1(2H)-yl)-N-benzyl-4-methylthiazole-5-carboxamide;
N-(4-fluorobenzyl)-4-methyl-2-(2-oxopyridin-1(2H)-yl)thiazole-5-carboxamide;
2-(4-(benzyloxy)-2-oxopyridin-1(2H)-yl)-N-(4-fluorobenzyl)-4-methylthiazole-5-carboxamide;
2-(4-(2-cyclopropylethoxy)-2-oxopyridin-1(2H)-yl)-N-(4-fluorobenzyl)-4-methylthiazole-5-carboxamide;
2-(4-(2-cyclopropylethoxy)-2-oxopyridin-1(2H)-yl)-4-methyl-N-(pyridin-3-ylmethyl)thiazole-5-carboxamide;
N-benzyl-4-methyl-2-(2-oxo-4-(pyridin-3-ylmethoxy)pyridin-1(2H)-yl)thiazole-5-carboxamide;
N-benzyl-2-(5-hydroxy-1-oxoisoquinolin-2(1H)-yl)-4-methylthiazole-5-carboxamide;
N-benzyl-2-(6-hydroxy-2-oxoquinolin-1(2H)-yl)-4-methylthiazole-5-carboxamide;
N-benzyl-2-(6-(benzyloxy)-2-oxoquinolin-1(2H)-yl)-4-methylthiazole-5-carboxamide;
N-benzyl-2-(5-(benzyloxy)-1-oxoisoquinolin-2(1H)-yl)-4-methylthiazole-5-carboxamide;
N-benzyl-2-(4-(benzyloxy)-2-oxopyridin-1(2H)-yl)-4-methyl-1H-imidazole-5-carboxamide;
N-benzyl-5-(4-(benzyloxy)-2-oxopyridin-1(2H)-yl)-3-methylthiophene-2-carboxamide;
N-benzyl-5-(4-hydroxy-2-oxopyridin-1(2H)-yl)-3-methylthiophene-2-carboxamide;
N-benzyl-2-(4-(benzyloxy)-2-oxopyridin-1(2H)-yl)-1,4-dimethyl-1H-imidazole-5-carboxamide;
N-benzyl-2-(4-(benzyloxy)-2-oxopyridin-1(2H)-yl)-1,5-dimethyl-1H-imidazole-4-carboxamide;
N-benzyl-5-(4-(2-cyclopropylethoxy)-2-oxopyridin-1(2H)-yl)-3-methylthiophene-2-carboxamide;
1-(5-(Benzylcarbamoyl)-4-methylthiazol-2-yl)-2-oxo-1,2-dihydropyridin-4-yl trifluoromethanesulfonate;
Ethyl 4-methyl-2-(2-oxo-4-phenylpyridin-1(2H)-yl)thiazole-5-carboxylate;
Ethyl 2-(4-(benzyloxy)-2-oxopyridin-1(2H)-yl)-4-methylthiazole-5-carboxylate;
Ethyl 2-(4-(benzyloxy)-2-oxopyridin-1(2H)-yl)-4-methyl-1H-imidazole-5-carboxylate;
Ethyl 2-(4-(benzyloxy)-2-oxopyridin-1(2H)-yl)-1,4-dimethyl-1H-imidazole-5-carboxylate;
Ethyl 2-(4-(benzyloxy)-2-oxopyridin-1(2H)-yl)-1,5-dimethyl-1H-imidazole-4-carboxylate;
4-Methyl-2-(2-oxo-4-phenylpyridin-1(2H)-yl)thiazole-5-carboxylic acid;
4-Methyl-2-(4-(benzyloxy)-2-oxopyridin-1(2H)-yl)thiazole-5-carboxylic acid;

2-(4-(Cyclopropylmethoxy)-2-oxopyridin-1(2H)-yl)-4-methylthiazole-5-carboxylic acid;
2-(4-(2-Cyclopropylethoxy)-2-oxopyridin-1(2H)-yl)-4-methylthiazole-5-carboxylic acid;
2-(4-Methoxy-2-oxopyridin-1(2H)-yl)-4-methylthiazole-5-carboxylic acid;
2-(4-Hydroxy-2-oxopyridin-1(2H)-yl)-4-methylthiazole-5-carboxylic acid;
Ethyl 2-(4-hydroxy-2-oxopyridin-1(2H)-yl)-4-methylthiazole-5-carboxylate;
Ethyl 2-(4-(cyclopropylmethoxy)-2-oxopyridin-1(2H)-yl)-4-methylthiazole-5-carboxylate;
Ethyl 2-(4-methoxy-2-oxopyridin-1(2H)-yl)-4-methylthiazole-5-carboxylate;
Ethyl 2-(4-(2-cyclopropylethoxy)-2-oxopyridin-1(2H)-yl)-4-methylthiazole-5-carboxylate;
2-(4-(Benzyloxy)-2-oxopyridin-1(2H)-yl)-4-methyl-1H-imidazole-5-carboxylic acid;
2-(4-(Benzyloxy)-2-oxopyridin-1(2H)-yl)-1,4-dimethyl-1H-imidazole-5-carboxylic acid;
2-(4-(Benzyloxy)-2-oxopyridin-1(2H)-yl)-4-methyl-N-(pyridin-3-ylmethyl)-1H-imidazole-5-carboxamide;
N-Benzyl-2-(4-(benzyloxy)-2-oxopyridin-1(2H)-yl)-4-methylthiazole-5-carboxamide;
N-Benzyl-4-methyl-2-(3-methyl-2-oxopyrazin-1(2H)-yl)thiazole-5-carboxamide;
N-Benzyl-2-(5-chloro-2-oxopyridin-1(2H)-yl)-4-methylthiazole-5-carboxamide;
N-Benzyl-4-methyl-2-(2-oxo-5-(trifluoromethyl)pyridin-1(2H)-yl)thiazole-5-carboxamide;
N-Benzyl-4-methyl-2-(2-oxo-3-(trifluoromethyl)pyridin-1(2H)-yl)thiazole-5-carboxamide;
N-Benzyl-4-methyl-2-(2-oxo-4-(trifluoromethyl)pyridin-1(2H)-yl)thiazole-5-carboxamide;
N-benzyl-2-(4-(benzylamino)-2-oxopyridin-1(2H)-yl)-4-methylthiazole-5-carboxamide;
N-Benzyl-4-methyl-2-(2-oxo-4-(pyridin-2-ylmethoxy)pyridin-1(2H)-yl)thiazole-5-carboxamide;
N-Benzyl-2-(6-hydroxy-1-oxoisoquinolin-2(1H)-yl)-4-methylthiazole-5-carboxamide;
N-Benzyl-5-(4-hydroxy-2-oxopyridin-1(2H)-yl)thiophene-3-carboxamide;
N-Benzyl-5-(4-(benzyloxy)-2-oxopyridin-1(2H)-yl)thiophene-3-carboxamide;
N-Benzyl-3-methyl-5-(2-oxo-4-(4-(trifluoromethyl)benzyloxy)pyridin-1(2H)-yl)thiophene-2-carboxamide;
N-Benzyl-5-(4-(4-fluorobenzyloxy)-2-oxopyridin-1(2H)-yl)-3-methylthiophene-2-carboxamide;
N-Benzyl-5-(4-(4-(difluoromethoxy)benzyloxy)-2-oxopyridin-1(2H)-yl)-3-methylthiophene-2-carboxamide;
N-Benzyl-3-methyl-5-(2-oxo-4-phenethoxypyridin-1(2H)-yl)thiophene-2-carboxamide;
2-(4-(Benzyloxy)-2-oxopyridin-1(2H)-yl)-1,5-dimethyl-2,3-dihydro-1H-imidazole-4-carboxylic acid;
N-benzyl-4-methyl-2-(2-oxo-5-(trifluoromethyl)pyridin-1(2H)-yl)thiazole-5-carboxamide;
N-benzyl-4-methyl-2-(2-oxo-4-(trifluoromethyl)pyridin-1(2H)-yl)thiazole-5-carboxamide;
N-benzyl-4-methyl-2-(2-oxo-4-((5-(trifluoromethyl)furan-2-yl)methoxy)pyridin-1(2H)-yl)thiazole-5-carboxamide;
N-benzyl-2-(4-(4-fluorobenzyloxy)-2-oxopyridin-1(2H)-yl)-4-methylthiazole-5-carboxamide;
2-(4-(benzyloxy)-2-oxopyridin-1(2H)-yl)-4-methyl-N-(pyridin-3-ylmethyl)thiazole-5-carboxamide;
N-benzyl-4-methyl-2-(2-oxo-4-(4-(trifluoromethyl)benzyloxy)pyridin-1(2H)-yl)thiazole-5-carboxamide;
2-(4-hydroxy-2-oxopyridin-1(2H)-yl)-4-methyl-N-(pyridin-3-ylmethyl)thiazole-5-carboxamide;
N-(3-fluorobenzyl)-2-(4-hydroxy-2-oxopyridin-1(2H)-yl)-4-methylthiazole-5-carboxamide;
N-(cyclopropylmethyl)-2-(4-hydroxy-2-oxopyridin-1(2H)-yl)-4-methylthiazole-5-carboxamide;
4-methyl-2-(2-oxopyridin-1(2H)-yl)-N-(pyridin-3-ylmethyl)thiazole-5-carboxamide;
N-(2-cyclopropylethyl)-2-(4-hydroxy-2-oxopyridin-1(2H)-yl)-4-methylthiazole-5-carboxamide;
N-(4-fluorophenethyl)-2-(4-hydroxy-2-oxopyridin-1(2H)-yl)-4-methylthiazole-5-carboxamide;
N-benzyl-4-methyl-2-(2-oxo-4-phenethylpyridine-1(2H)-yl)thiazole-5-carboxamide;
N-benzyl-4-methyl-2-(2-oxo-4-phenoxypyridin-1(2H)-yl)thiazole-5-carboxamide;
4-methyl-2-(2-oxo-4-(trifluoromethyl)pyridin-1(2H)-yl)-N-(pyridin-3-ylmethyl)thiazole-5-carboxamide;
N-(3,4-difluorobenzyl)-2-(4-hydroxy-2-oxopyridin-1(2H)-yl)-4-methylthiazole-5-carboxamide;
N-benzyl-4-methyl-2-(2-oxo-4-(2-oxoimidazolidin-1-yl)pyridin-1(2H)-yl)thiazole-5-carboxamide;
2-(4-hydroxy-2-oxopyridin-1(2H)-yl)-4-methyl-N-(pyridin-4-ylmethyl)thiazole-5-carboxamide;
2-(4-(4-(difluoromethoxy)benzyloxy)-2-oxopyridin-1(2H)-yl)-N-(4-fluorobenzyl)-4-methylthiazole-5-carboxamide;
2-(4-methoxy-2-oxopyridin-1(2H)-yl)-4-methyl-N-(pyridin-3-ylmethyl)thiazole-5-carboxamide;
4-methyl-2-(2-oxo-4-((5-(trifluoromethyl)furan-2-yl)methoxy)pyridin-1(2H)-yl)-N-(pyridin-3-ylmethyl)thiazole-5-carboxamide;
2-(4-(4-fluorobenzyloxy)-2-oxopyridin-1(2H)-yl)-4-methyl-N-(pyridin-3-ylmethyl)thiazole-5-carboxamide;
N-(4-fluorobenzyl)-2-(4-(4-fluorobenzyloxy)-2-oxopyridin-1(2H)-yl)-4-methylthiazole-5-carboxamide;
N-benzyl-2-(4-(cyclopentylmethoxy)-2-oxopyridin-1(2H)-yl)-4-methylthiazole-5-carboxamide;
N-(3,4-difluorobenzyl)-2-(4-methoxy-2-oxopyridin-1(2H)-yl)-4-methylthiazole-5-carboxamide;
N-benzyl-4-methyl-2-(2-oxo-4-(phenoxymethyl)pyridin-1(2H)-yl)thiazole-5-carboxamide;
2-(4-(benzyloxy)-2-oxopyridin-1(2H)-yl)-N-(3,4-difluorobenzyl)-4-methylthiazole-5-carboxamide;
N-benzyl-4-methyl-2-(2-oxo-4-((tetrahydrofuran-2-yl)methoxy)pyridin-1(2H)-yl)thiazole-5-carboxamide;
3-((2-(4-methoxy-2-oxopyridin-1(2H)-yl)-4-methylthiazole-5-carboxamido)methyl)pyridine 1-oxide;
N-benzyl-4-methyl-2-(2-oxo-4-((5-phenyl-1,3,4-oxadiazol-2-yl)methoxy)pyridin-1(2H)-yl)thiazole-5-carboxamide;
N-benzyl-2-(4-((5-(4-chlorophenyl)-1,3,4-oxadiazol-2-yl)methoxy)-2-oxopyridin-1(2H)-yl)-4-methylthiazole-5-carboxamide;
N-benzyl-2-(4-((4-chloro-2-(trifluoromethyl)quinolin-6-yl)methoxy)-2-oxopyridin-1(2H)-yl)-4-methylthiazole-5-carboxamide;
N-benzyl-4-methyl-2-(2-oxo-4-((6-(trifluoromethyl)pyridin-3-yl)methoxy)pyridin-1(2H)-yl)thiazole-5-carboxamide;
N-benzyl-4-methyl-2-(2-oxo-4-(thiazol-4-ylmethoxy)pyridin-1(2H)-yl)thiazole-5-carboxamide;
N-benzyl-4-methyl-2-(2-oxo-4-((tetrahydro-2H-pyran-2-yl)methoxy)pyridin-1(2H)-yl)thiazole-5-carboxamide;

N-(benzo[b]thiophen-2-ylmethyl)-2-(4-(benzyloxy)-2-oxopyridin-1(2H)-yl)-4-methylthiazole-5-carboxamide;
2-(4-(benzyloxy)-2-oxopyridin-1(2H)-yl)-4-methyl-N-((3-methylthiophen-2-yl)methyl)thiazole-5-carboxamide;
2-(4-(benzyloxy)-2-oxopyridin-1(2H)-yl)-N-(2,3-dihydro-1H-inden-2-yl)-4-methylthiazole-5-carboxamide;
2-(4-(benzyloxy)-2-oxopyridin-1(2H)-yl)-4-methyl-N-((5-methylpyrazin-2-yl)methyl)thiazole-5-carboxamide;
2-(4-(benzyloxy)-2-oxopyridin-1(2H)-yl)-4-methyl-N-(oxazol-2-ylmethyl)thiazole-5-carboxamide;
2-(4-(benzyloxy)-2-oxopyridin-1(2H)-yl)-4-methyl-N-((5-methyl-2-(trifluoromethyl)furan-3-yl)methyl)thiazole-5-carboxamide;
2-(4-(benzyloxy)-2-oxopyridin-1(2H)-yl)-4-methyl-N-(thiazol-2-ylmethyl)thiazole-5-carboxamide;
2-(4-(benzyloxy)-2-oxopyridin-1(2H)-yl)-4-methyl-N-((5-methylthiophen-2-yl)methyl)thiazole-5-carboxamide;
2-(4-(benzyloxy)-2-oxopyridin-1(2H)-yl)-4-methyl-N-((4-methylthiophen-2-yl)methyl)thiazole-5-carboxamide;
2-(4-(benzyloxy)-2-oxopyridin-1(2H)-yl)-N-((1,5-dimethyl-1H-pyrrol-2-yl)methyl)-4-methylthiazole-5-carboxamide;
2-(4-(benzyloxy)-2-oxopyridin-1(2H)-yl)-4-methyl-N-((1-methyl-1H-imidazol-5-yl)methyl)thiazole-5-carboxamide;
2-(4-(benzyloxy)-2-oxopyridin-1(2H)-yl)-4-methyl-N-((1-methyl-1H-pyrazol-4-yl)methyl)thiazole-5-carboxamide;
2-(4-(benzyloxy)-2-oxopyridin-1(2H)-yl)-4-methyl-N-((2-methylthiazol-4-yl)methyl)thiazole-5-carboxamide;
2-(4-(benzyloxy)-2-oxopyridin-1(2H)-yl)-N-((5-cyanofuran-2-yl)methyl)-4-methylthiazole-5-carboxamide;
N-(benzo[d]oxazol-2-ylmethyl)-2-(4-(benzyloxy)-2-oxopyridin-1(2H)-yl)-4-methylthiazole-5-carboxamide;
Ethyl-5-((2-(4-(benzyloxy)-2-oxopyridin-1(2H)-yl)-4-methylthiazole-5-carboxamido)methyl)furan-2-carboxylate;
N-((1H-indol-2-yl)methyl)-2-(4-(benzyloxy)-2-oxopyridin-1(2H)-yl)-4-methylthiazole-5-carboxamide;
N-(benzo[d]thiazol-2-ylmethyl)-2-(4-(benzyloxy)-2-oxopyridin-1(2H)-yl)-4-methylthiazole-5-carboxamide;
N-((1H-pyrazol-3-yl)methyl)-2-(4-(benzyloxy)-2-oxopyridin-1(2H)-yl)-4-methylthiazole-5-carboxamide;
2-(4-(benzyloxy)-2-oxopyridin-1(2H)-yl)-N-((6-chloropyridin-3-yl)methyl)-4-methylthiazole-5-carboxamide;
2-(4-(benzyloxy)-2-oxopyridin-1(2H)-yl)-4-methyl-N-((6-(trifluoromethyl)pyridin-3-yl)methyl)thiazole-5-carboxamide;
2-(4-(benzyloxy)-2-oxopyridin-1(2H)-yl)-4-methyl-N-((5-methylfuran-2-yl)methyl)thiazole-5-carboxamide;
N-benzyl-4-methyl-2-(4-((5-methylisoxazol-3-yl)methoxy)-2-oxopyridin-1(2H)-yl)thiazole-5-carboxamide;
N-benzyl-2-(4-((5-chlorothiophen-2-yl)methoxy)-2-oxopyridin-1(2H)-yl)-4-methylthiazole-5-carboxamide;
N-benzyl-2-(4-((5-chlorothiophen-2-yl)methoxy)-2-oxopyridin-1(2H)-yl)-4-methylthiazole-5-carboxamide;
N-benzyl-2-(4-((2-isopropylthiazol-4-yl)methoxy)-2-oxopyridin-1(2H)-yl)-4-methylthiazole-5-carboxamide;
N-benzyl-2-(4-((6-chloropyridin-3-yl)methoxy)-2-oxopyridin-1(2H)-yl)-4-methylthiazole-5-carboxamide;
N-benzyl-4-methyl-2-(4-((2-methylthiazol-4-yl)methoxy)-2-oxopyridin-1(2H)-yl)thiazole-5-carboxamide;
2-(4-((1,2,4-oxadiazol-3-yl)methoxy)-2-oxopyridin-1(2H)-yl)-N-benzyl-4-methylthiazole-5-carboxamide;
N-benzyl-2-(4-((3,5-dimethylisoxazol-4-yl)methoxy)-2-oxopyridin-1(2H)-yl)-4-methylthiazole-5-carboxamide;
2-(4-hydroxy-2-oxopyridin-1(2H)-yl)-4-methyl-N-((6-methylpyrazin-2-yl)methyl)thiazole-5-carboxamide;
2-(4-hydroxy-2-oxopyridin-1(2H)-yl)-4-methyl-N-(oxazol-2-ylmethyl)thiazole-5-carboxamide; and
N-benzyl-2-(4-cyclopropyl-2-oxopyridin-1(2H)-yl)-4-methylthiazole-5-carboxamide.

16. A pharmaceutical composition, comprising:
the compound of formula (I) according to claim 1 and a pharmaceutically acceptable excipient or carrier.

\* \* \* \* \*